US012396850B2

(12) United States Patent
Tyler, II et al.

(10) Patent No.: US 12,396,850 B2
(45) Date of Patent: Aug. 26, 2025

(54) CATHETERIZATION METHOD AND APPARATUS

(71) Applicant: Edwards Lifesciences Corporation, Irvine, CA (US)

(72) Inventors: Gregory Scott Tyler, II, Winston-Salem, NC (US); Thanh Huy Le, Oceanside, CA (US); Tam Van Nguyen, Westminster, CA (US); Daniel James Montoya, Redmond, WA (US); Grant Matthew Stearns, Tustin, CA (US); Eric Robert Dixon, Villa Park, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1034 days.

(21) Appl. No.: 17/315,187

(22) Filed: May 7, 2021

(65) Prior Publication Data

US 2021/0259835 A1    Aug. 26, 2021

Related U.S. Application Data

(63) Continuation of application No. PCT/US2019/062977, filed on Nov. 25, 2019.
(Continued)

(51) Int. Cl.
*A61F 2/24* (2006.01)
*A61B 5/00* (2006.01)
(Continued)

(52) U.S. Cl.
CPC .......... *A61F 2/2427* (2013.01); *A61B 5/0215* (2013.01); *A61B 5/6852* (2013.01);
(Continued)

(58) Field of Classification Search
CPC .... A61F 2/2427; A61F 2/2466; A61B 5/0215; A61B 5/6852; A61M 2025/0002; A61M 2025/0034
See application file for complete search history.

(56) References Cited

U.S. PATENT DOCUMENTS 3,874,388 A    4/1975  King et al.
4,011,947 A    3/1977  Sawyer
(Continued)

FOREIGN PATENT DOCUMENTS

CA    2682474 A1    7/2008
CN    1142351 A     2/1997
(Continued)

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.
(Continued)

*Primary Examiner* — Dung T Ulsh
(74) *Attorney, Agent, or Firm* — Anya Adams

(57) ABSTRACT

Catheterization methods and apparatuses allow sensing of pressures inside the heart and for removing air from catheters. A delivery system can use the same components that are used to deliver a valve repair or replacement device to measure the pressure in the atrium or other heart chamber. A pressure sensor can be included in one of the catheters of the delivery system or pressure can be sensed through the same port that is used to flush a catheter. The delivery system can be inserted into the heart, delivering the valve repair or replacement device to the native valve, such as the mitral valve, the tricuspid valve, the aortic valve, or the pulmonary valve.

21 Claims, 47 Drawing Sheets

Related U.S. Application Data

(60) Provisional application No. 62/772,735, filed on Nov. 29, 2018.

(51) Int. Cl.
  *A61B 5/0215* (2006.01)
  *A61B 17/00* (2006.01)
  *A61M 25/00* (2006.01)

(52) U.S. Cl.
  CPC ...... *A61B 17/00234* (2013.01); *A61F 2/2466* (2013.01); *A61B 2017/00243* (2013.01); *A61B 2017/00561* (2013.01); *A61M 2025/0002* (2013.01); *A61M 2025/0034* (2013.01); *A61M 2230/04* (2013.01)

(56) References Cited

U.S. PATENT DOCUMENTS

| | | |
|---|---|---|
| 4,340,091 A | 7/1982 | Skelton et al. |
| 4,506,669 A | 3/1985 | Blake, III |
| 4,590,937 A | 5/1986 | Deniega |
| 4,645,496 A * | 2/1987 | Oscarsson ............ A61B 5/0215 251/117 |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Galser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Ellasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |
| 9,198,757 B2 | 12/2015 | Schroeder et al. |

(56) References Cited

U.S. PATENT DOCUMENTS

| | | |
|---|---|---|
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0128611 A1 | 9/2002 | Kandalaft |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251177 A1 | 11/2005 | Saadat et al. |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Ellasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Ellasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0024818 A1* | 2/2010 | Stenzler ............ A61M 16/0066 604/533 |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022507 A1 | 1/2012 | Najafi et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |

(56) References Cited

U.S. PATENT DOCUMENTS

| | | |
|---|---|---|
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2013/0331692 A1 | 12/2013 | Mouri |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277403 A1 | 9/2014 | Peter |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351645 A1 | 12/2015 | Hiltner |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wel |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0346084 A1 | 12/2016 | Taylor et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0071487 A1 | 3/2018 | Khuu et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0116843 A1* | 5/2018 | Schreck ............... A61F 2/07 |
| 2018/0126095 A1* | 5/2018 | von Oepen ........... A61B 90/70 |
| 2018/0126119 A1 | 5/2018 | McNiven et al. |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0214664 A1 | 8/2018 | Kim et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0344490 A1 | 12/2018 | Fox et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |

(56) References Cited

U.S. PATENT DOCUMENTS

| | | |
|---|---|---|
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0323668 A1 | 10/2020 | Diedering et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |

FOREIGN PATENT DOCUMENTS

| | | |
|---|---|---|
| CN | 101636611 A | 1/2010 |
| CN | 106175845 A | 12/2016 |
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| JP | 2001046509 A | 2/2001 |
| JP | 2017522933 A | 8/2017 |
| WO | 2007047488 A2 | 4/2007 |
| WO | 2014064694 A2 | 5/2014 |
| WO | 2017015632 A1 | 1/2017 |
| WO | 2018013856 A1 | 1/2018 |
| WO | 2018022919 A1 | 2/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Pavcnik et al., "Development and Initial Experimental Evaluation of a Prosthetic Aortic Valve for Transcatheter Placement," Radiology, vol. 183, No. 1, pp. 151-154, Apr. 1, 1992. Elsevier, United States.

Praz et al., "Compassionate use of the PASCAL transcatheter mitral valve repair system for patients with severe mitral regurgitation: a multicentre, prospective, observational, first-in-man study," The Lancet, vol. 390, Issue 10096, pp. 773-780, Aug. 19, 2017, Lancet, United States.

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi: 10.21037/jtd.2017.10.156, AME Publishing Company, Hong Kong, China.

Al Zaibag et al., "Percutaneous Balloon Valvotomy in Tricuspid Stenosis", British Heart Journal, vol. 57, No. 1, Jan. 1987.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

(56) References Cited

OTHER PUBLICATIONS

Batista RJ et al., "Partial left ventriculectomy to treat end-stage heart disease", Ann Thorac Surg., vol. 64, Issue-3, pp. 634-638, Sep. 1997.
Beall AC Jr. et al., "Clinical experience with a dacron velour-covered teflon-disc mitral-valve prosthesis", Ann Thorac Surg., vol. 5, Issue 5, pp. 402-410, May 1968.
Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.
Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.
Fucci et al., "Improved results with mitral valve repair using new surgical techniques", Eur J Cardiothorac Surg. 1995;Issue 9, vol. 11, pp. 621-626.
Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faill . . .
Lawrence, Jr., et al., "Percutaneous Endovascular Graft: Experimental Evaluation", Cardiovascular Radiology 163, pp. 357-360, May 1987.
Maisano F et al., 'The edge-to-edge technique: a simplified method to correct mitral insufficiency', Eur J Cardiothorac Surg., vol. 13, Issue-3, pp. 240-245, Mar. 1998.
Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.
Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.
Reul RM et al., "Mitral valve reconstruction for mitral insufficiency", Prog Cardiovasc Dis., vol. 39, Issue-6, May-Jun. 1997.
Rösch et al., "The Birth, Early Years and Future of Interventional Radiology," Journal of Vascular and Interventional Radiology, vol. 14, No. 7, pp. 841-853, Jul. 1, 2003, Elsevier, United States.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.
Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.
Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.
Uchida et al., "Modifications of Gianturco Expandable Wire Stents", Technical Note, American Roentgen Ray Society, pp. 1185-1187, May 1988.
Umaña JP et al., Bow-tie' mitral valve repair: an adjuvant technique for ischemic mitral regurgitation, Ann Thorac Surg., vol. 66, Issue-6, pp. 1640-1646, Nov. 1998.
Urban, Philip Md, "Coronary Artery Stenting", pp. 5-47, © 1991, ISBN: 2-88049-054-5, Editions Medecine et Hygiene, Geneva, Switzerland.
Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.
Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

\* cited by examiner

CATHETERIZATION METHOD AND APPARATUS

RELATED APPLICATION

The present application is a continuation application of International Application No. PCT/US2019/062977, filed on Nov. 25, 2019 and published as WO 2020/112622, which claims the benefit of U.S. Provisional Patent Application Ser. No. 62/772,735, filed on Nov. 29, 2018, titled "Method for Measuring Atrial Pressures Intraoperatively Without Requiring A Separate Catheter," which are incorporated herein by reference in their entireties for all purposes.

BACKGROUND

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium. Being able to take pressure measurements from one or more surrounding chambers of the heart might provide information indicative of whether the implant is effective.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present. Monitoring pressures in one or more chambers might provide helpful information during procedures to address valve issues.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

Catheterization methods and apparatuses are described herein. Some of the methods and apparatuses relate to catheter flushing and couplers for catheter flushing. Some of the methods and apparatuses relate to cardiac pressure measurement and catheter assemblies for cardiac pressure measurement. The treatment methods and steps shown and/or discussed herein can be performed on a living animal or on a simulation, such as on a cadaver, cadaver heart, simulator (e.g. with the body parts, heart, tissue, etc. being simulated), etc.

In one example embodiment, a catheter coupler, flush section, or flush port includes a housing, a cap, and one or more seals. The housing has a catheter connection lumen, a plurality of passages, and an outer circumferential channel. The plurality of passages each connect the catheter connection lumen to the outer circumferential channel. The cap is rotatably coupled to the housing. The cap has an outlet port in fluid communication with the outer circumferential passage. The one or more seals provide seals between the housing and the cap that direct fluid flow from the outer circumferential passage to the outlet port. The cap is rotatable to position the outlet port a vertical orientation without rotating the housing.

In one example embodiment, a method of flushing a catheter coupler comprises rotating a cap while keeping the position of a housing stationary. The cap rotates an outlet port to a top-dead-center position. A vacuum is applied to the outlet port to flush the catheter coupler.

In one example embodiment, a delivery system includes a first catheter coupler, a second catheter coupler, a first catheter connected to the first catheter coupler, and a second catheter connected to the second catheter coupler. Each of the first and second catheter couplers have a housing, a cap, and one or more seals. In some implementations, the housings each have a catheter connection lumen, a plurality of passages, and an outer circumferential channel. The plurality of passages each connect the catheter connection lumen to the outer circumferential channel. The caps are each rotatably coupled to the housing. The cap has an outlet port in fluid communication with the outer circumferential passage. The one or more seals provide seals between the housing and the cap that direct fluid flow from the outer circumferential passage to the outlet port. Each cap is rotatable to position the outlet port in a vertical orientation without rotating the housing or the connected catheter. The second catheter extends through the first catheter coupler and the first catheter.

In one example embodiment, a method of measuring a fluid pressure includes inserting a first catheter through a second catheter. A radially inwardly extending projection on an inside surface of the second catheter maintains a flow space between the first catheter and the second catheter. A pressure of the fluid in the flow space is measured.

In one example embodiment, a catheter coupler, flush section, or flush port includes a catheter connection lumen, an outer circumferential passage, a plurality of connecting passages, and an outlet port. Each of the connecting passages connect the catheter connection lumen to the outer circumferential passage. The outlet port is in fluid communication with the outer circumferential passage. The outer circumferential passage and the plurality of connecting passages are sized such that when: 1) the outlet port is oriented in direction not vertically upwardly facing (e.g., a downwardly facing direction, etc.); 2) upper ones of the connecting passages contain air; and 3) lower ones of the connecting passages contain liquid, the air is drawn out of the outlet port.

In one example embodiment, a delivery system includes a first catheter coupler, a second catheter coupler, a first catheter connected to the first catheter coupler, and a second catheter connected to the second catheter coupler. Each of the catheter couplers includes a catheter connection lumen, an outer circumferential passage, a plurality of connecting passages, and an outlet port. Each of the connecting passages of the couplers connect the catheter connection lumen to the outer circumferential passage. The outlet ports are each in fluid communication with the corresponding outer circumferential passage of the coupler. The outer circumferential passage and the plurality of connecting passages of each coupler are sized such that when: 1) the outlet port is oriented in a direction not vertically upwardly facing (e.g., a downwardly facing direction, etc.); 2) upper ones of the connecting passages contain air; and 3) lower ones of the connecting passages contain liquid, the air is drawn out of the outlet port. The second catheter extends through the first catheter coupler and the first catheter.

In one example embodiment, a method of measuring pressure in a heart chamber, includes inserting a valve implant or repair device delivery system into a left atrium. The valve implant or repair device delivery system includes a catheter, a pusher element, and a pressure sensor. The first catheter has a delivery lumen. The pusher element is positioned within the delivery lumen of the first catheter. The valve implant or repair device is detachably connected to the pusher element. The pressure sensor lumen is in at least one of the catheter and the pusher element. The pressure sensor and a fluid are disposed in the pressure sensor lumen. An open distal end of the pressure sensor lumen is exposed to the left atrium. A first blood pressure measurement is taken within the left atrium with the pressure sensor at a designated time during a cardiac cycle. This method can be performed on a living animal or on a simulation, such as on a cadaver, cadaver heart, simulator (e.g. with the body parts, heart, tissue, etc. being simulated), etc.

In one example embodiment, a device for measuring pressure in a heart chamber using a valve implant or repair device delivery system includes a catheter, a pusher element, a pressure sensor lumen, and a pressure sensor. The catheter has a delivery lumen. The pusher element is positioned within the delivery lumen of the first catheter. The valve implant or repair device is detachably connected to the pusher element. The pressure sensor lumen is in at least one of the first catheter and the pusher element. The pressure sensor and a fluid are disposed in the pressure sensor lumen. The pressure sensor lumen comprises an open distal end.

Other examples from the rest of this disclosure can also be used and features from any described examples can be incorporated into the examples above mutatis mutandis.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

Figure 1:
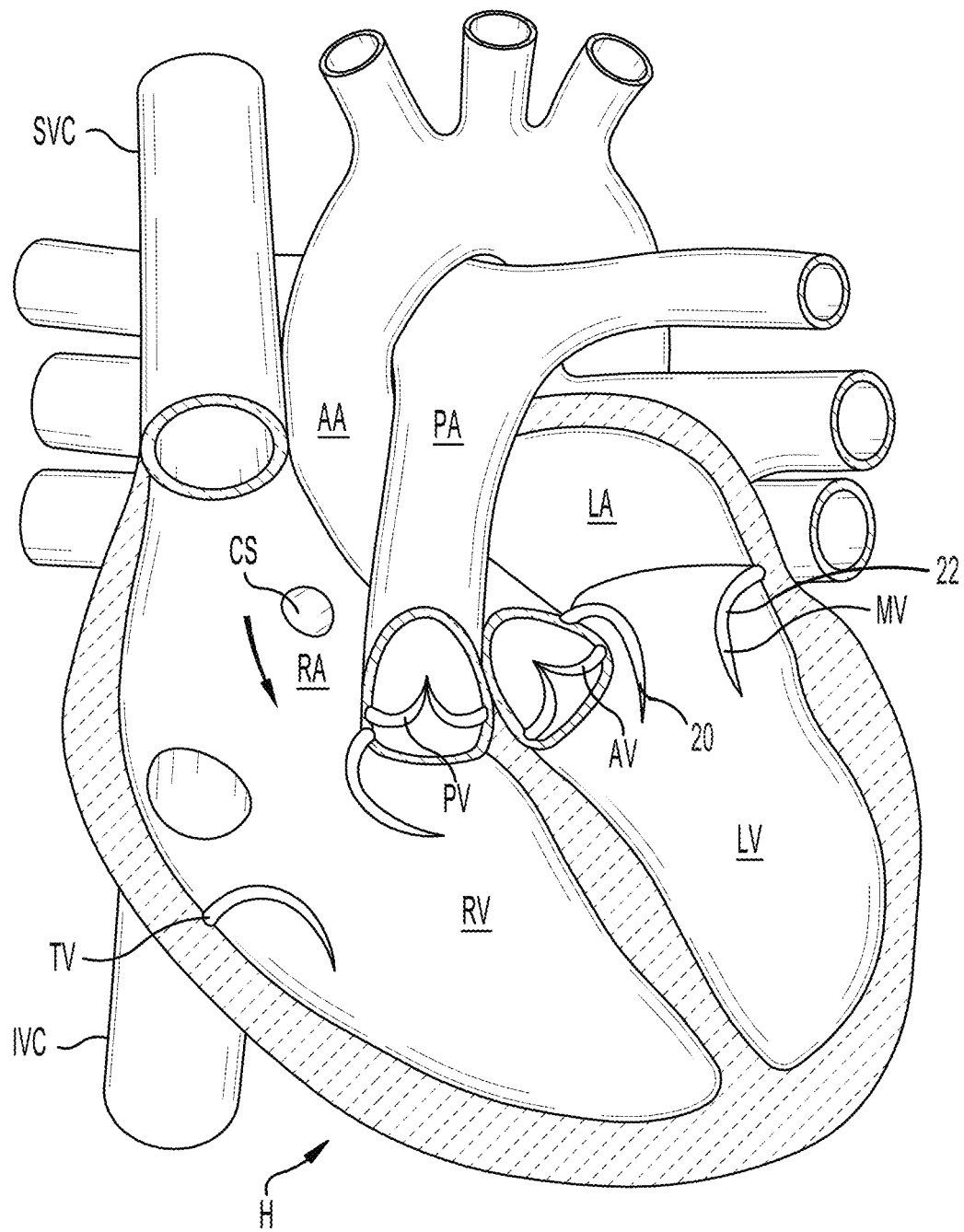
FIG. 1 illustrates a cutaway view of the human heart in a diastolic phase.

The following description refers to the accompanying drawings, which illustrate specific embodiments of the present disclosure. Other embodiments having different structures and operation do not depart from the scope of the present disclosure.

Delivery systems, apparatuses, devices, and methods for measuring atrial pressures during transcatheter valve repair and/or replacement procedures are described. The delivery system uses the same components that are used to deliver the valve repair and/or replacement device to measure the pressure in the atrium (or other heart chamber). The delivery device and method can use a pressure sensor within and/or delivered through a catheter and/or pusher rod or tube system that is used to administer a heart valve therapy. The method includes inserting the delivery system into an atria of the heart, delivering the valve repair and/or replacement device to the native valve (such as the mitral valve, the tricuspid valve, the aortic valve, or the pulmonary valve) with the delivery system, and measuring the pressure with the pressure sensor through an opening in one of the catheters and/or pushers of the delivery system. In an example embodiment, the delivery system and method eliminates the need to introduce a separate catheter into the heart. For example, a lower atrial pressure in the left atrium at the position of the delivery device during ventricular systole indicates less regurgitation through the mitral valve.

This lower pressure can indicate an effectively delivered mitral valve repair device (e.g. leaflet repair or modification device, annulus modification device, or chordae modification or replacement device) or replacement mitral valve implant.

The disclosed delivery system and method does not require re-catheterization or other access of the left atrium to measure pressures. The disclosed delivery system and method also reduces the reliance on echo and other imaging to determine whether the valve therapy is effective.

It should be noted that various embodiments of methods for measuring the atrial pressure in a heart during systole and/or diastole, before, during, and/or after the administration of a valve repair therapy are disclosed herein, and any combination of these options can be made unless specifically excluded. In other words, individual components of the disclosed devices and methods can be combined unless mutually exclusive or otherwise physically impossible. Further, these methods can be performed on a living animal or on a simulation, such as on a cadaver, cadaver heart, simulator (e.g. with the body parts, heart, tissue, etc. being simulated), etc.

The example embodiments described herein rely on existing space and/or structure within catheters and/or pusher rods or tubes used to deliver a valve repair or replacement device to more reliably measure atrial pressures during and/or after procedures for heart valve repair or replacement, including the mitral valve and the tricuspid valve. In some example embodiments, the delivery device for a replacement aortic valve can include the disclosed pressure measurement features. The valve repair therapy can be a replacement valve implant or a valve repair device. The atrial pressure can be in the right atrium or the left atrium. In some example embodiments, the delivery device can be configured to measure the pressure in a ventricle when the delivery device is positioned in the ventricle. The space can be within a catheter sheath, steering catheter, device delivery catheter, and/or pusher rod or tube. The space within catheters and/or pusher rod or tube can be within the main lumen of the catheter or pusher or can be within the wall of the catheter or pusher. The lumen can be reinforced with a pressure sensor catheter. The pressure sensor catheter can be a reinforcing sheath having its own lumen. Pressure can be measured with a pressure sensor. The pressure sensor can be an electric pressure sensor within a fluid-filled lumen or in fluid communication with the lumen. The fluid can be saline or another biocompatible fluid. In one example embodiment, a pressure sensor is placed in an optionally reinforced lumen or a port is provided for an off-the-shelf catheter to enter the body without having to re-catheterize the heart. The integration of the pressure sensor reduces movement and/or vibration of the pressure sensor to provide a more accurate pressure measurement. This more accurate measurement provides valuable data to the operator to determine efficacy of the device implanted. By providing a lumen for an off-the-shelf pressure sensor within the main body of the delivery catheter (for example, a steerable catheter), the noise or vibration sensed by the pressure sensor that occurs in the heart chamber due to the flow of blood and the beating of the heart is reduced and a better indication of therapy efficacy can be obtained.

In an example embodiment, the lumen for the pressure sensor can have an exit opening at the tip of the outer catheter, where the implant catheter exits. In another example embodiment, the lumen for the pressure sensor can exit at the tip of the steering catheter. In an example embodiment, the lumen can exit in a flexible section of a catheter that is positioned in the atrium when the catheter is in the heart and positioned towards a valve. A steerable catheter can be used in any of the example embodiments described herein. Other existing catheters can also be used. The pressure sensor can be connected to a monitoring system through either the flush port on the handle or a separate port on the handle designed for the introduction of a pressure sensor, and/or direct attachment of a pressure sensor. During use, the pressure sensor can optionally be positioned external to the delivery device, such that it extends distally therefrom. In an example embodiment, the pressure sensor can be positioned so that a portion of the pressure sensor extends distally from an opening. In an example embodiment, the pressure sensor can be positioned within a lumen of the delivery device.

The pressure monitoring device can be selected to accommodate normal positioning of a catheter, which typically includes but is not limited to, deflection, advancement, retraction, and/or rotation of the catheter.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

Figure 2:
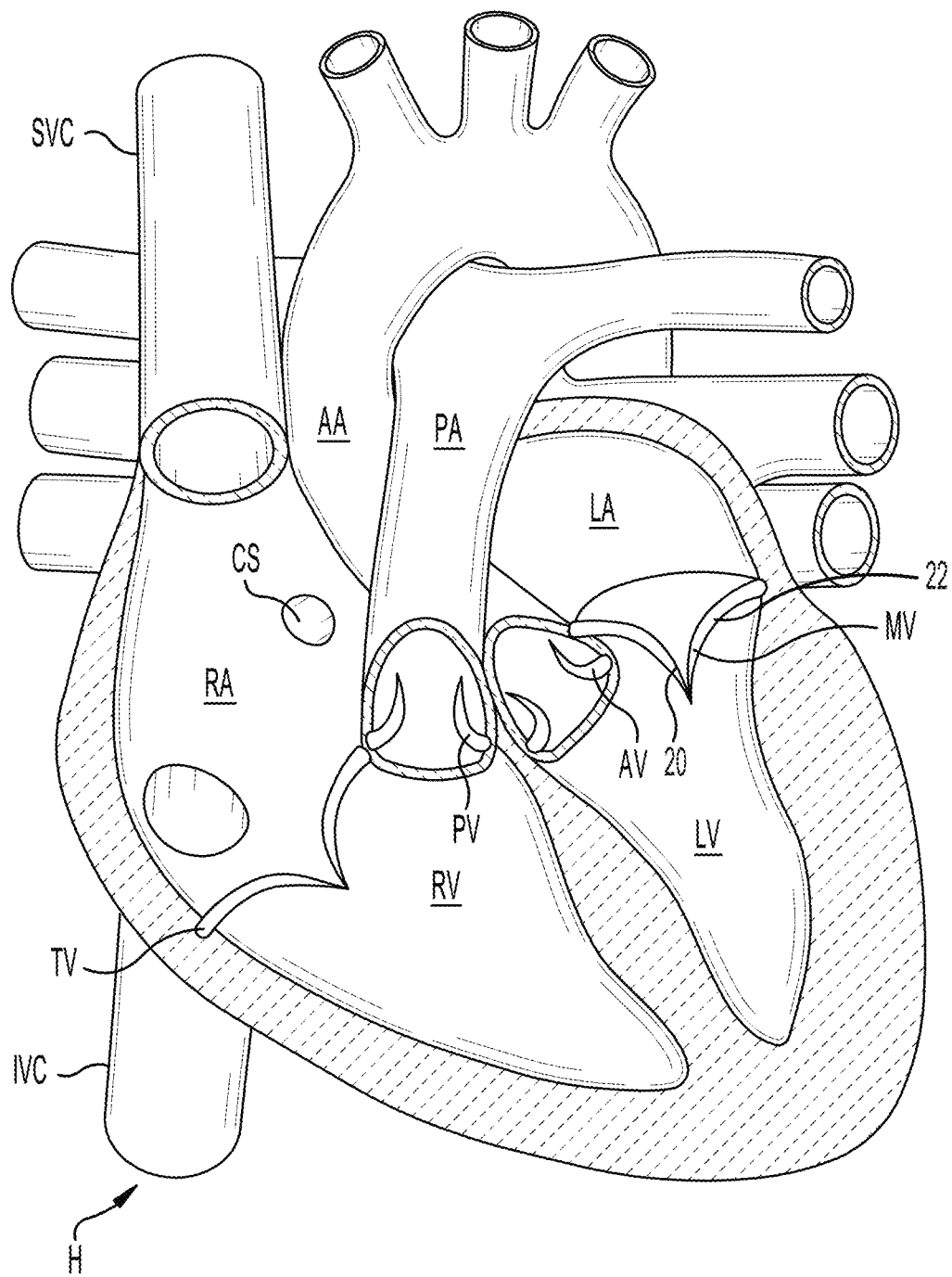
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flowstream to form the one-way, fluid-occluding surfaces. The methods, systems, devices, apparatuses, etc. herein are described primarily with respect to the mitral valve MV. Therefore, anatomical structures of the left atrium LA and left ventricle LV will be explained in greater detail. It should be understood that the methods and apparatuses described herein can also be used in repairing other native valves, e.g., the devices can be used in repairing the tricuspid valve TV, the aortic valve AV, and the pulmonary valve PV. Therefore, pressures in the right atrium RA and/or right ventricle RV can be measured in the same or a similar manner as the left atrium LA and/or the left ventricle LV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein PV. In one example embodiment, the devices described by the present application are used to repair the function of a defective mitral valve MV. That is, the devices are configured to help close the leaflets of the mitral valve to prevent blood from regurgitating from the left ventricle LV and back into the left atrium LA.

Figure 3:
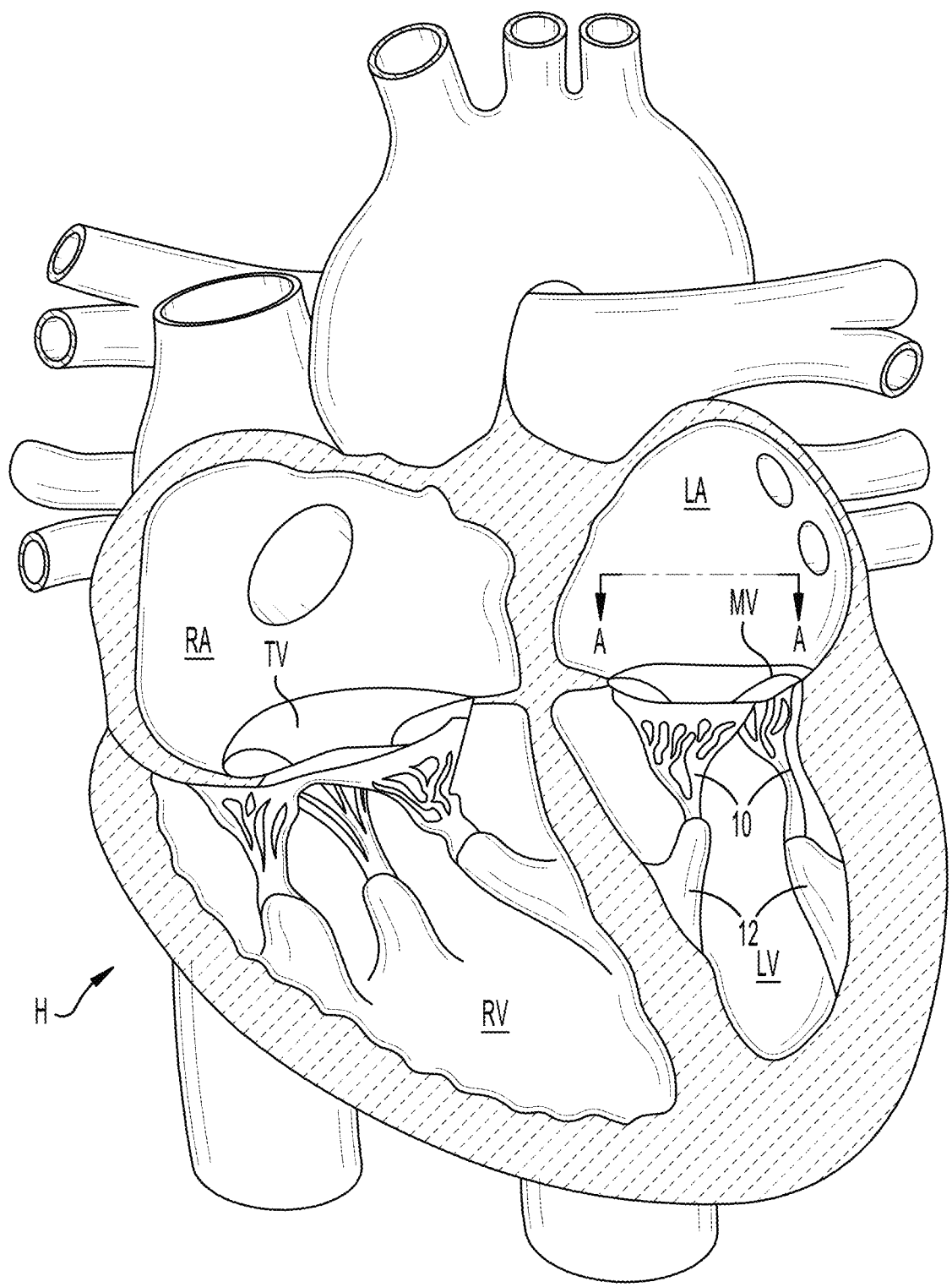
FIG. 3 illustrates a cutaway view of the human heart in a diastolic phase, in which the chordae tendineae are shown attaching the leaflets of the mitral and tricuspid valves to ventricle walls.

Referring now to FIGS. 1-6, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three main mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (IIIb).

Figure 4:
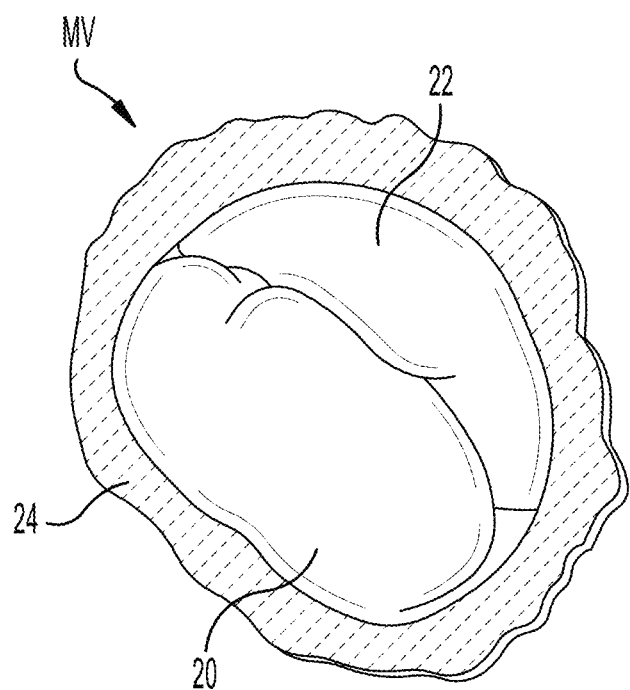
FIG. 4 illustrates a healthy mitral valve with the leaflets closed as viewed from an atrial side of the mitral valve.
Figure 5:
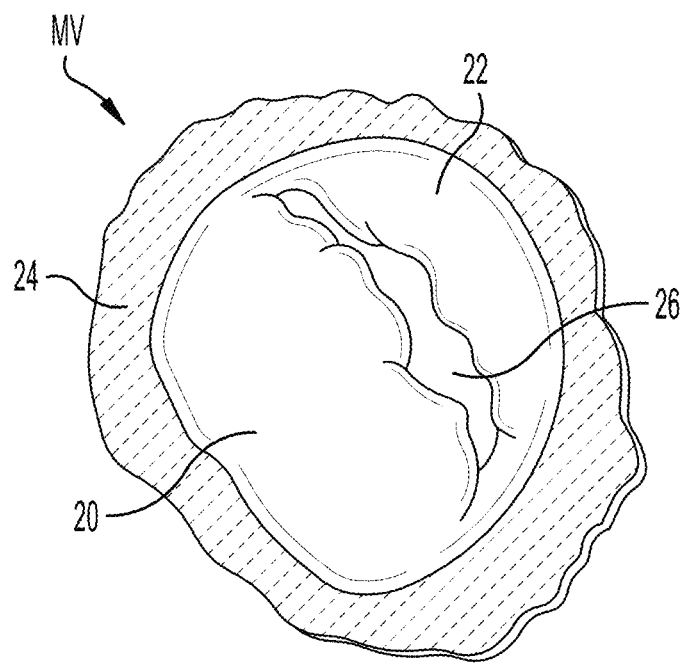
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
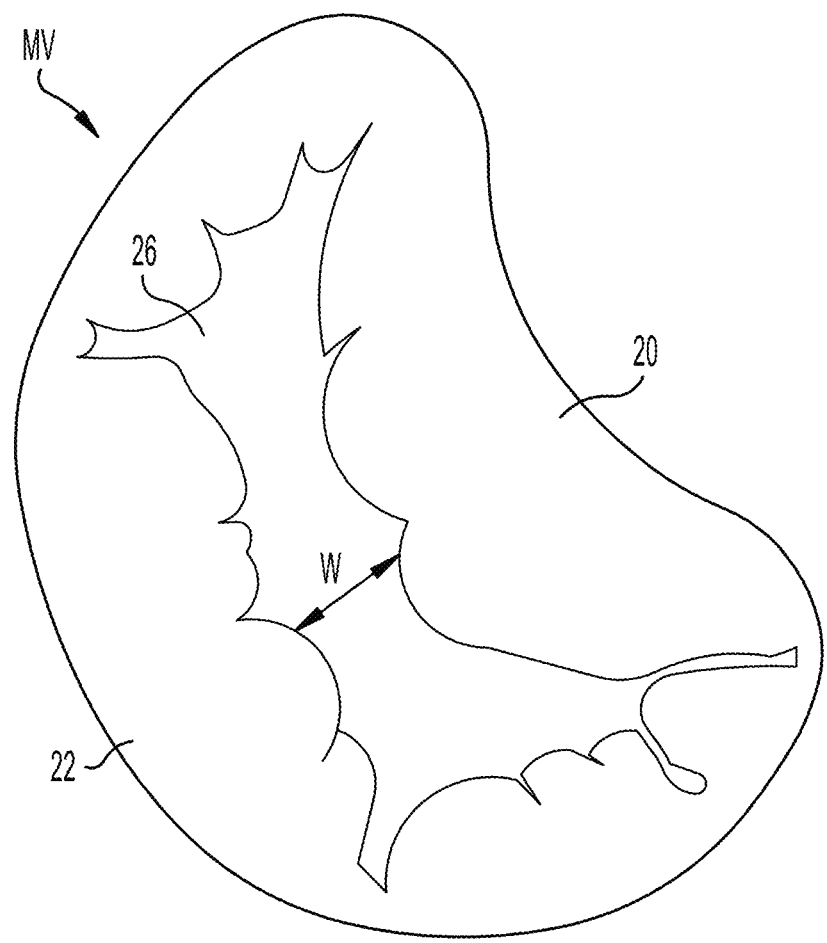
FIG. 6 illustrates a mitral valve having a wide gap between the posterior leaflet and the anterior leaflet.
Figure 7:
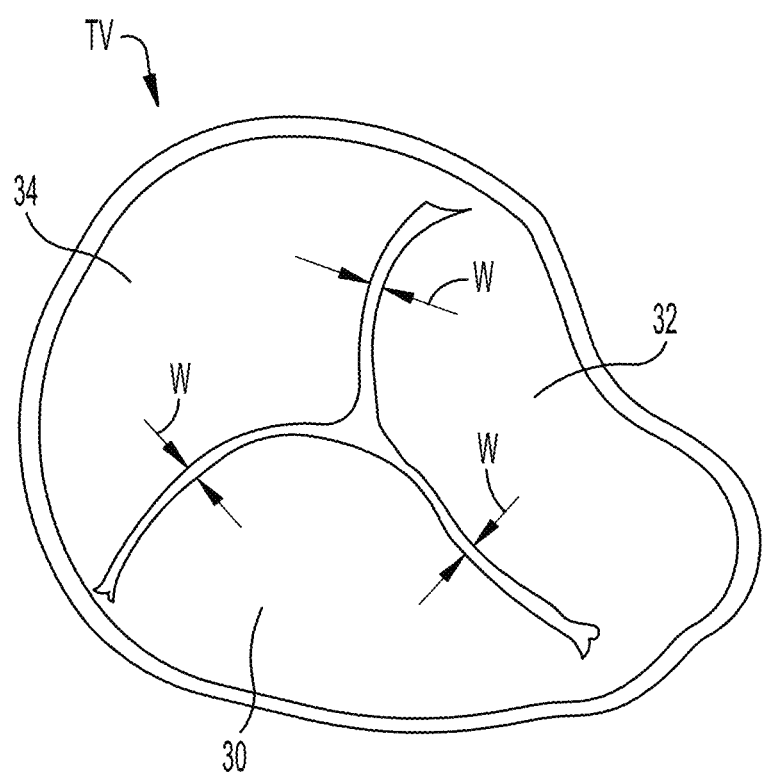
FIG. 7 illustrates a tricuspid valve viewed from an atrial side of the tricuspid valve.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

When mitral valve regurgitation occurs, blood enters the left atrium from the left ventricle during systole. In a healthy heart, blood should only enter the left atrium from the pulmonary veins, not the left ventricle. The left atrial pressure then increases above the pressure it should be. For example, normal left atrial pressure can range from about 5 to about 15 mmHg. But when mitral valve regurgitation occurs, left atrial pressure could increase to a higher pressure, for example, 25 mmHg. With mitral valve regurgitation, the left atrial pressure is increased overall throughout the cardiac cycle and is most noticeable at the end of systole.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve.

Referring now to FIGS. 8-14, a schematically illustrated implantable prosthetic device 100 is shown in various stages of deployment. The prosthetic device 100 and associated systems, methods, etc. are described in more detail in International Application Nos. PCT/US2018/028189 and PCT/US2019/055320, the disclosures of which are incorporated herein by reference in their entirety. The device 100 can include any other features for an implantable prosthetic device discussed in the present application, and the device 100 can be positioned to engage valve tissue (e.g., leaflets 20, 22) as part of any suitable valve repair system (e.g., any valve repair system disclosed in the present application).

The device 100 is deployed and can include a coaptation portion or coaption portion 140 and an anchor portion 106. The device 100 can be deployed from a delivery sheath and/or can be deployed by a pusher tube or rod 81. The coaption portion 140 of the device 100 includes a coaption element 110 that is adapted to be implanted between the leaflets of the native valve (e.g., native mitral valve, native tricuspid valve, etc.) and is slidably attached to an actuation member or actuation element 112 (e.g., a wire, shaft, rod, line, suture, tether, etc.). The anchor portion 106 is actuatable between open and closed conditions and can take a wide variety of forms, such as, for example, paddles, gripping elements, or the like. Actuation of the actuation element 112 opens and closes the anchor portion 106 of the device 100 to grasp the native valve leaflets during implantation. The actuation element 112 can take a wide variety of different forms. For example, the actuation element can be threaded such that rotation of the actuation element moves the anchor portion 106 relative to the coaption portion 140. Or, the actuation element may be unthreaded, such that pushing or pulling the actuation element 112 moves the anchor portion 106 relative to the coaption portion 140.

The anchor portion 106 of the device 100 includes outer paddles 120 and inner paddles 122 that are connected between a cap 114 and the coaption element 110 by portions 124, 126, 128. The portions 124, 126, 128 can be jointed and/or flexible to move between all of the positions described below. The interconnection of the outer paddles 120, the inner paddles 122, the coaption element 110, and the cap 114 by the portions 124, 126, and 128 can constrain the device to the positions and movements illustrated herein.

The actuation member or actuation element 112 extends through the delivery sheath and/or the pusher tube/rod and the coaption element 110 to the cap 114 at the distal connection of the anchor portion 106. Extending and retracting the actuation element 112 increases and decreases the spacing between the coaption element 110 and the cap 114, respectively. A collar 115 removably attaches the coaption element 110 to the pusher tube or rod 81 so that the actuation element 112 slides through the collar 115 and coaption element 110 during actuation to open and close the paddles 120, 122 of the anchor portion 106. After the device 100 is connected to valve tissue, if the device 100 needs to be removed from the valve tissue, a retrieval device can be used to connect to the collar 115 such that the actuation wire can extend through the collar 115 and the coaption element 110 to engage the anchor portion 106 to open the paddles 120, 122 and remove the device 100 from the valve tissue. Examples of retrieval devices that could be used are shown in PCT Application No. PCT/US2019/062391 filed Nov. 20, 2019, which is incorporated herein by reference in its entirety.

Figure 8:
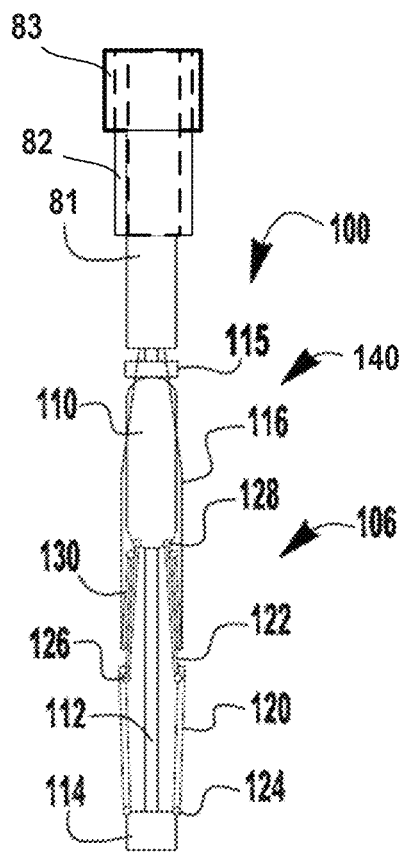
FIGS. 8-14 illustrate an example embodiment of an implantable prosthetic device, in various stages of deployment.

Referring now to FIG. 8, the device 100 is shown in an elongated or fully open condition for deployment from the delivery sheath. The device 100 is loaded in the delivery sheath in the fully open position, because the fully open position takes up the least space and allows the smallest catheter to be used (or the largest implantable device 100 to be used for a given catheter size). In the elongated condition the cap 114 is spaced apart from the coaption element 110 such that the paddles 120, 122 of the anchor portion 106 are fully extended. In some embodiments, an angle formed between the interior of the outer and inner paddles 120, 122 is approximately 180 degrees. The barbed clasps 130 are kept in a closed condition during deployment through the delivery sheath 83 so that the barbs 136 (FIGS. 9 and 11) do not catch or damage the sheath or tissue in the patient's heart.

Figure 9:
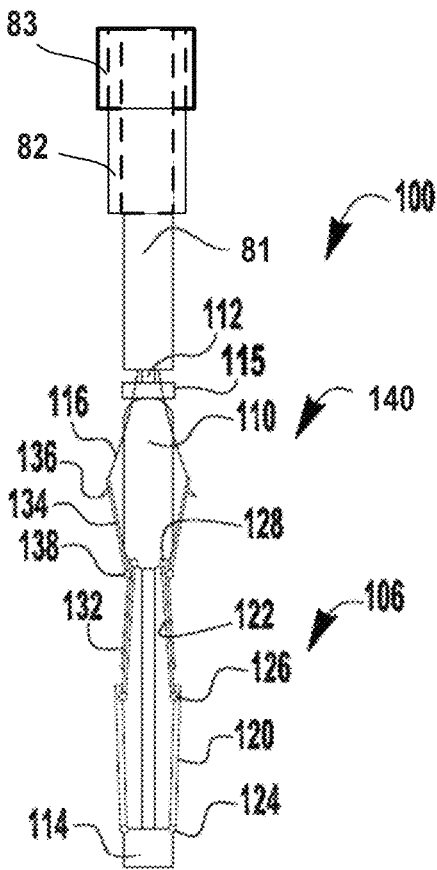

Referring now to FIG. 9, the device 100 is shown in an elongated detangling condition, similar to FIG. 8, but with the barbed clasps 130 in a fully open position, ranging from about 140 degrees to about 200 degrees, such as about 170 degrees to about 190 degrees, or about 180 degrees between fixed and moveable portions of the barbed clasps 130. Fully opening the paddles 120, 122 and the clasps 130 has been found to improve ease of detanglement from anatomy of the patient during implantation of the device 100.

Figure 10:
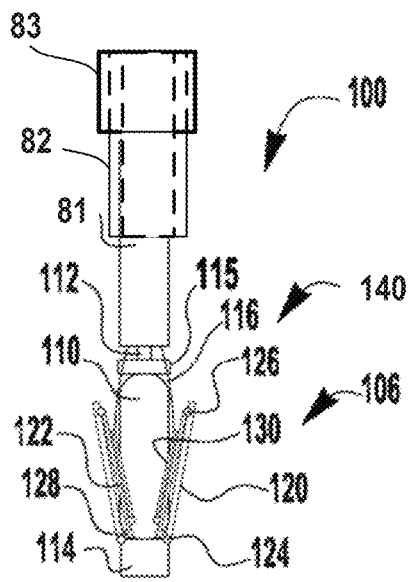

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the actuation member or actuation element 112 is retracted to pull the cap 114 towards the coaption element 110. The joints or flexible connections 126 between the outer paddle 120 and inner paddle 122 are constrained in movement such that compression forces acting on the outer paddle 120 from the cap 114 being retracted towards the coaption element 110 cause the paddles 120, 122 or gripping elements to move radially outward. During movement from the open to closed position, the outer paddles 120 maintain an acute angle with the actuation element 112. The outer paddles 120 can optionally be biased toward a closed position. The inner paddles 122 during the same motion move through a considerably larger angle as they are oriented away from the coaption element 110 in the open condition and collapse along the sides of the coaption element 110 in the closed condition. In some embodiments, the inner paddles 122 are thinner and/or narrower than the outer paddles 120, and the joint or flexible portions 126, 128 connected to the inner paddles 122 can be thinner and/or more flexible. For example, this increased flexibility can allow more movement than the joint or flexible portion 124 connecting the outer paddle 124 to the cap 114. In some embodiments, the outer paddles 120 are narrower than the inner paddles 122. The joint or flexible portions 126, 128 connected to the inner paddles 122 can be more flexible, for example, to allow more movement than the joint or flexible portion 124 connecting the outer paddle 124 to the cap 114. In some embodiments, the inner paddles 122 can be the same width or substantially the same width as the outer paddles.

Figure 11:
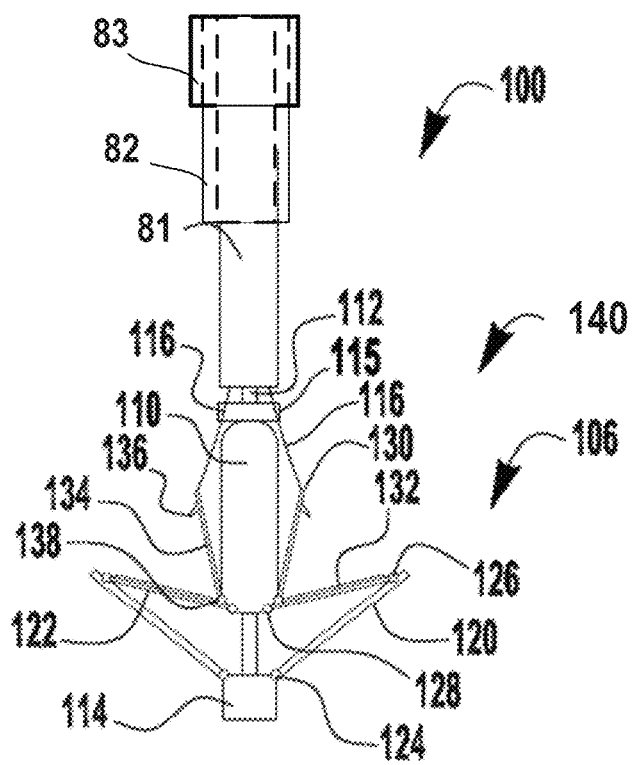
Figure 12:
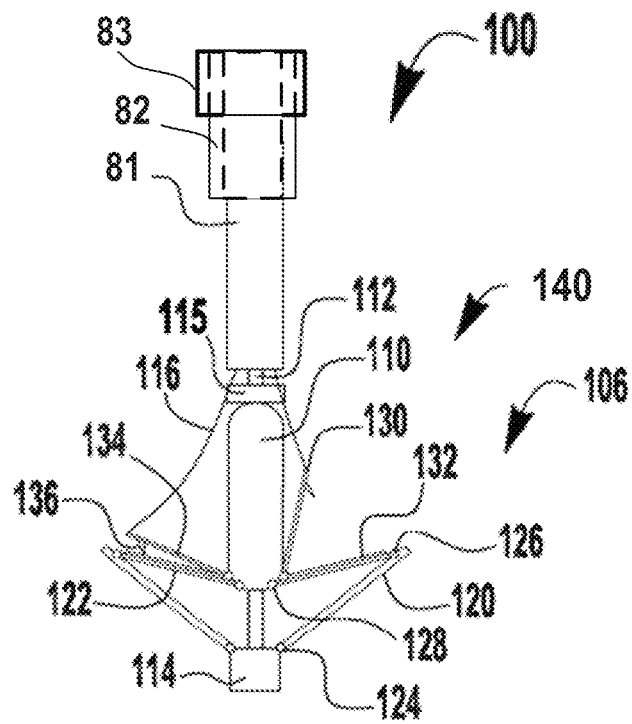
Figure 13:
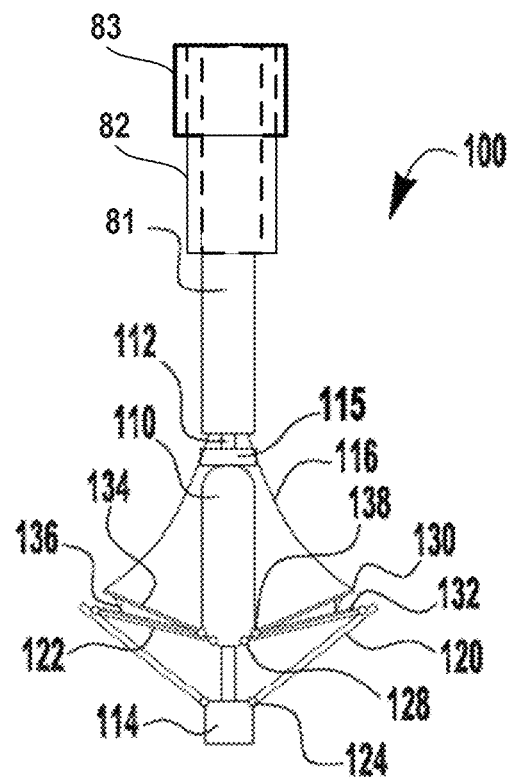

Referring now to FIGS. 11-13, the device 100 is shown in a partially open, grasp-ready condition. To transition from the fully closed to the partially open condition, the actuation member or actuation element 112 (e.g., an actuation wire, actuation shaft, etc.) is extended to push the cap 114 away from the coaption element 110, thereby pulling on the outer paddles 120, which in turn pulls on the inner paddles 122, causing the anchor portion 106 to partially unfold. The actuation lines 116 are also retracted to open the clasps 130 so that the leaflets can be grasped. In the example illustrated by FIG. 11, the pair of inner and outer paddles 122, 120 are moved in unison, rather than independently, by a single actuation element 112. Also, the positions of the clasps 130 are dependent on the positions of the paddles 122, 120. For example, referring to FIG. 10 closing the paddles 122, 120 also closes the clasps. In certain embodiments, the paddles 120, 122 can be independently controllable. For example, the device 100 can have two actuation elements and two independent caps, such that one independent wire and cap are used to control one paddle, and the other independent wire and cap are used to control the other paddle.

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 may be repeatedly actuated to repeatedly open and close the barbed clasps 130.

Figure 14:
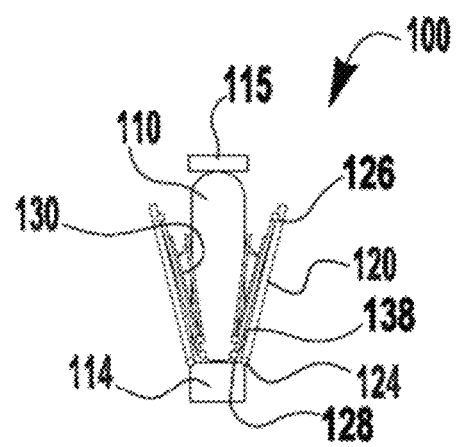

Referring now to FIG. 14, the device 100 is shown in a fully closed and deployed condition. The pusher tube or rod 81 and actuation element 112 are retracted and the paddles 120, 122 and clasps 130 remain in a fully closed position. Once deployed, the device 100 can be maintained in the fully closed position with a mechanical latch or can be biased to remain closed through the use of spring materials, such as steel, other metals, plastics, composites, etc. or shape-memory alloys such as Nitinol. For example, the jointed or flexible portions 124, 126, 128, 138, and/or the inner and outer paddles 122, and/or an additional biasing component can be formed of metals such as steel or shape-memory alloy, such as Nitinol—produced in a wire, sheet, tubing, or laser sintered powder—and are biased to hold the outer paddles 120 closed around the coaption element 110 and the barbed clasps 130 pinched around native leaflets. Similarly, the fixed and moveable arms 132, 134 of the barbed clasps 130 are biased to pinch the leaflets. In some embodiments, the joint portions 124, 126, 128, 138, and/or the inner and outer paddles 122, and/or an additional biasing component can be formed of any other suitably elastic material, such as a metal or polymer material, to maintain the device in the closed condition after implantation.

Figure 15:
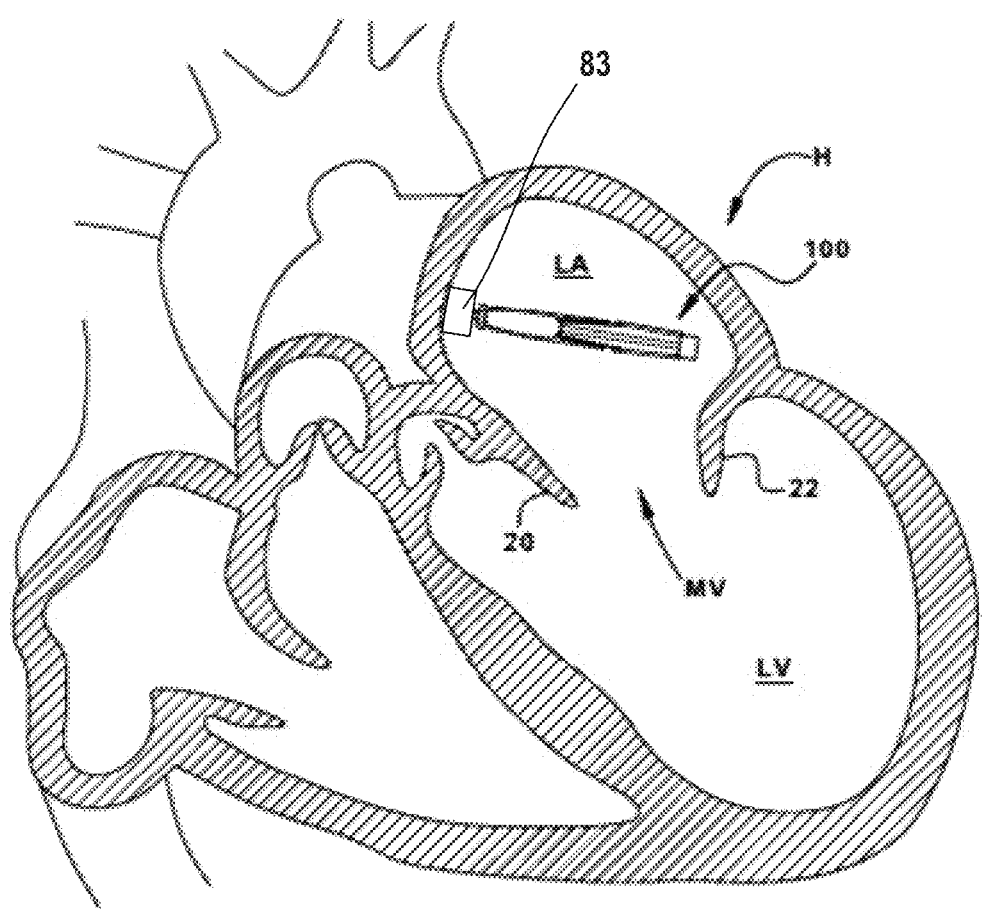
FIGS. 15-20 illustrate the example implantable prosthetic device of FIGS. 8-14 being delivered and implanted within a native valve.
Figure 16:
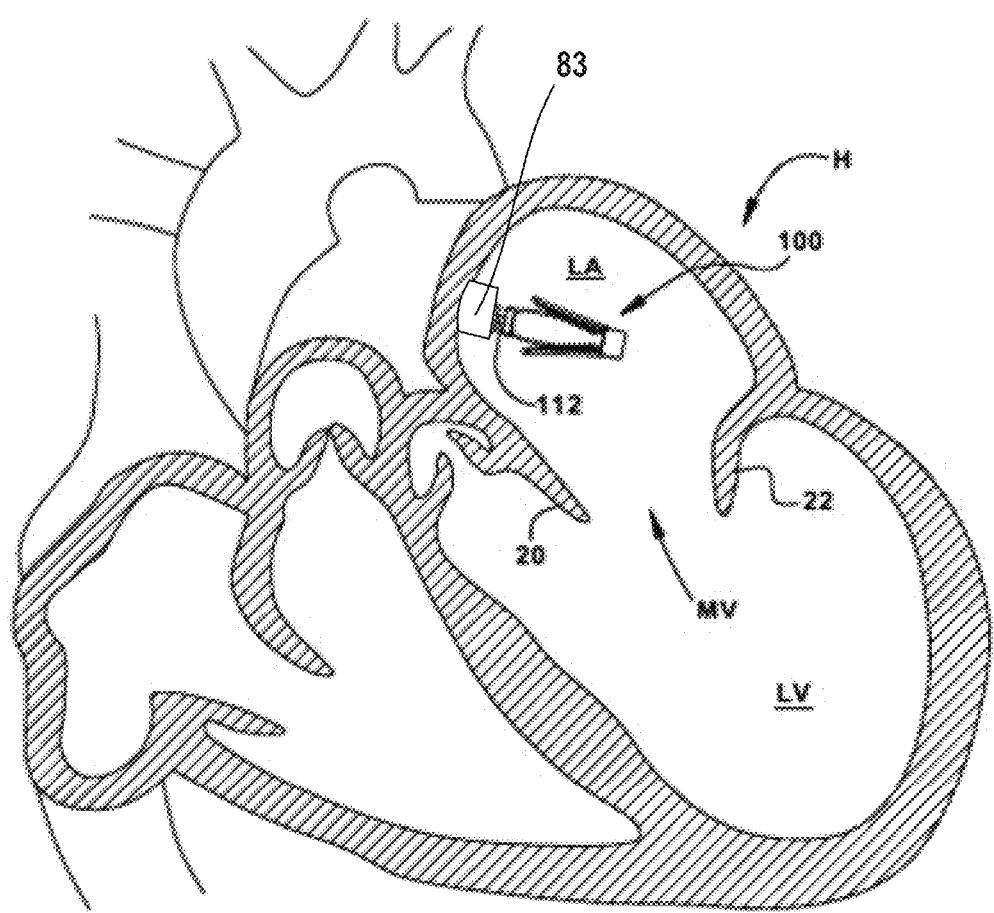
Figure 17:
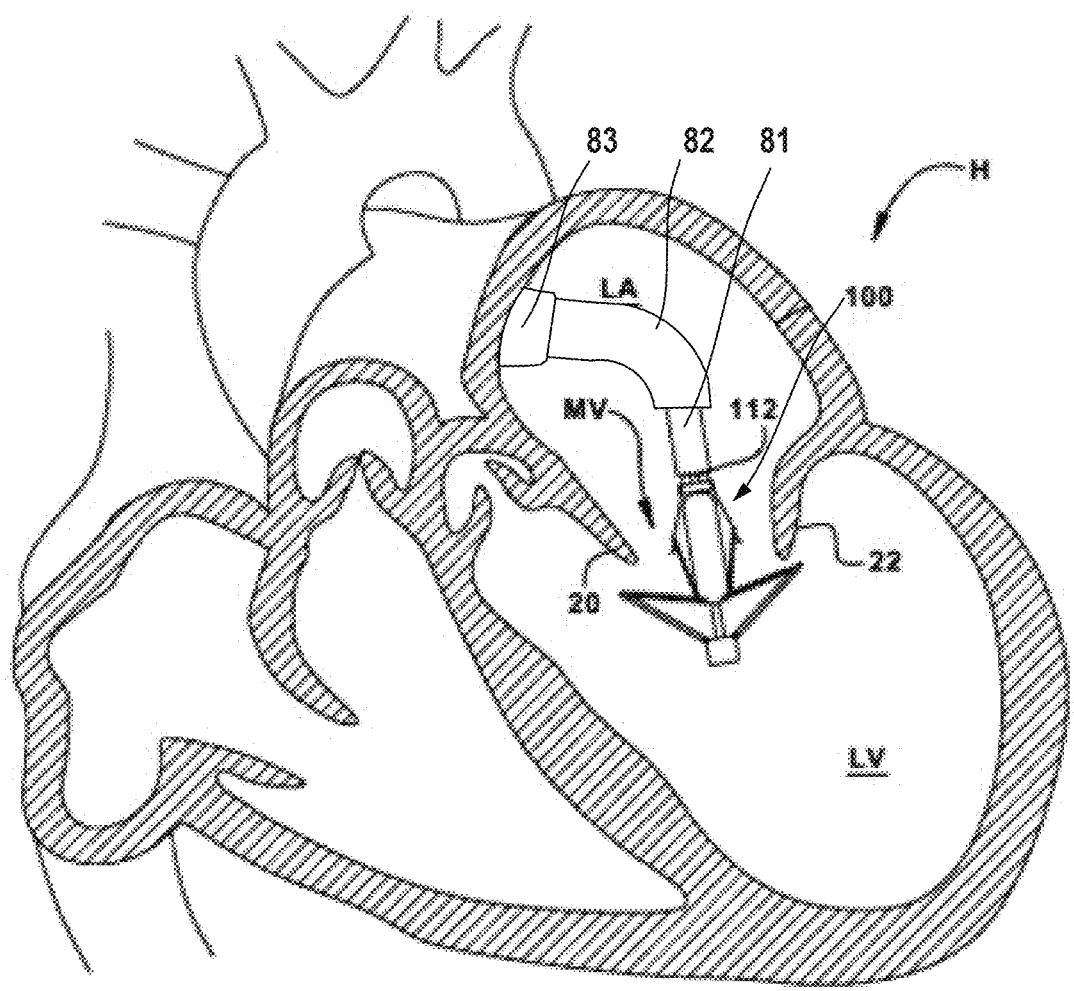
Figure 18:
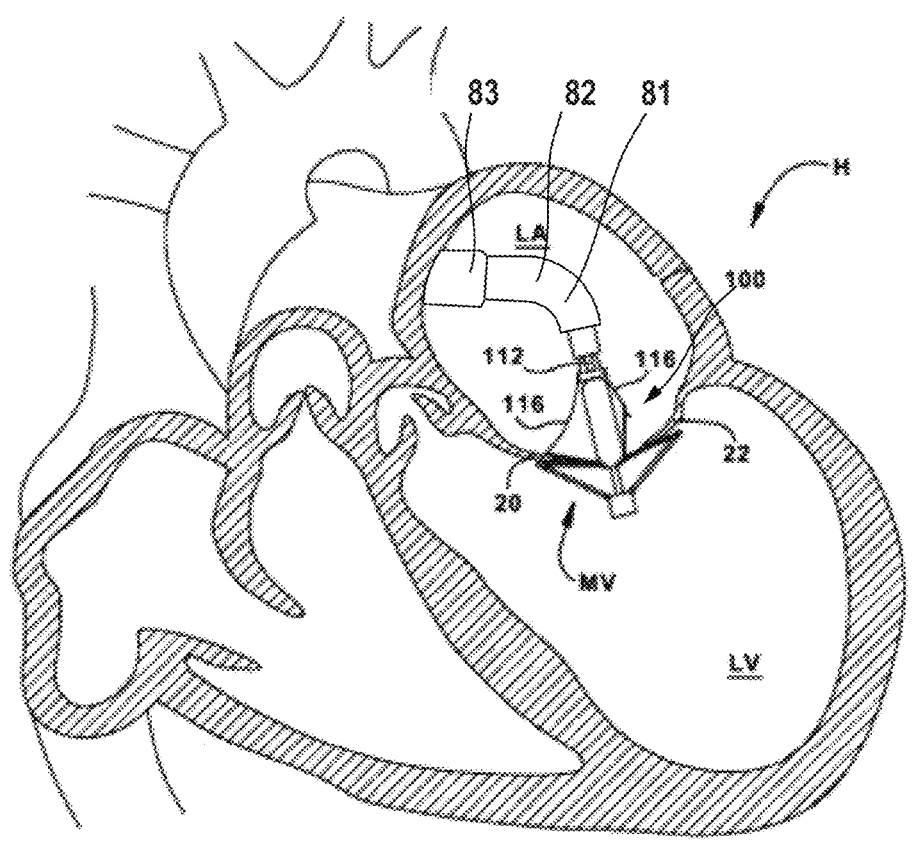
Figure 19:
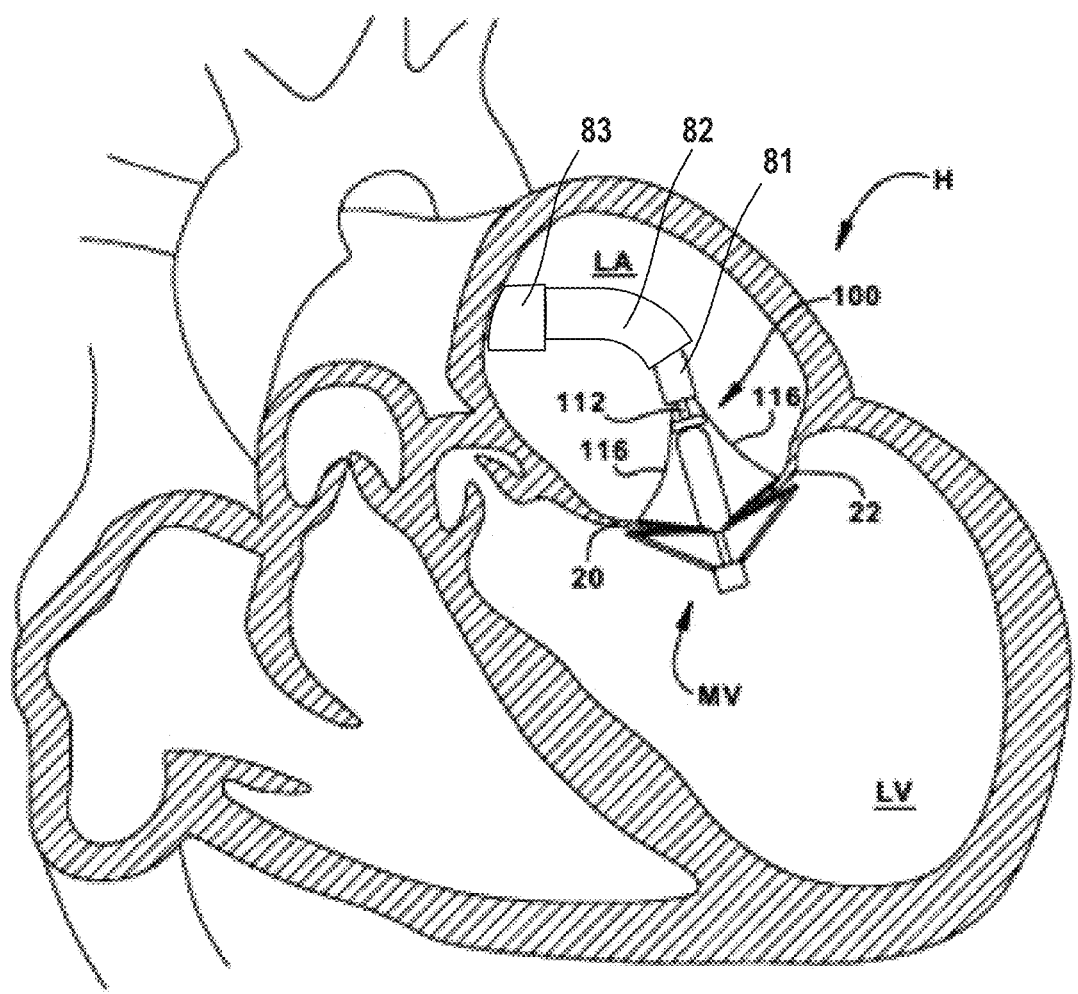
Figure 20:
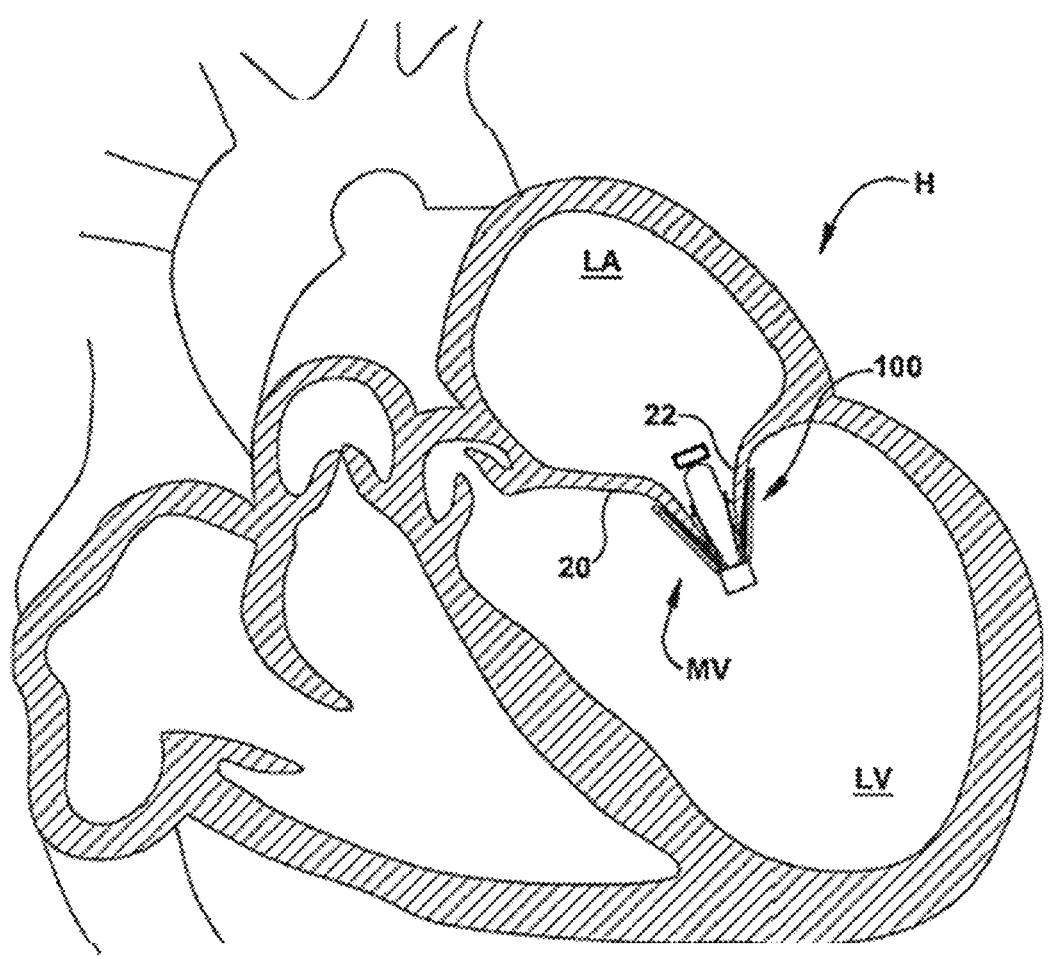

Referring now to FIGS. 15-20, the implantable device 100 of FIGS. 8-14 is shown being delivered and implanted within the native mitral valve MV of the heart H. Referring now to FIG. 15, the outer catheter or sheath 83 is inserted into the left atrium LA through the septum and the device 100 is deployed from the outer catheter in the fully open condition. The actuation element 112 is then retracted to move the device 100 into the fully closed condition shown in FIG. 16. As can be seen in FIG. 17, the device 100 is moved into position within the mitral valve MV into the ventricle LV and partially opened so that the leaflets 20, 22 can be grasped. The steerable catheter 82 is extended out past the distal end of the outer catheter 83, and the pusher tube or rod 81 is extended out past the distal end of the steerable catheter. Referring now to FIG. 18, an actuation line 116 is extended to close one of the clasps 130, capturing a leaflet 20. FIG. 19 shows the other actuation line 116 being then extended to close the other clasp 130, capturing the remaining leaflet 22. Lastly, as can be seen in FIG. 20, the pusher tube or rod 81 and actuation element 112 and actuation lines 116 are then retracted and the device 100 is fully closed and deployed in the native mitral valve MV.

Figure 21A:
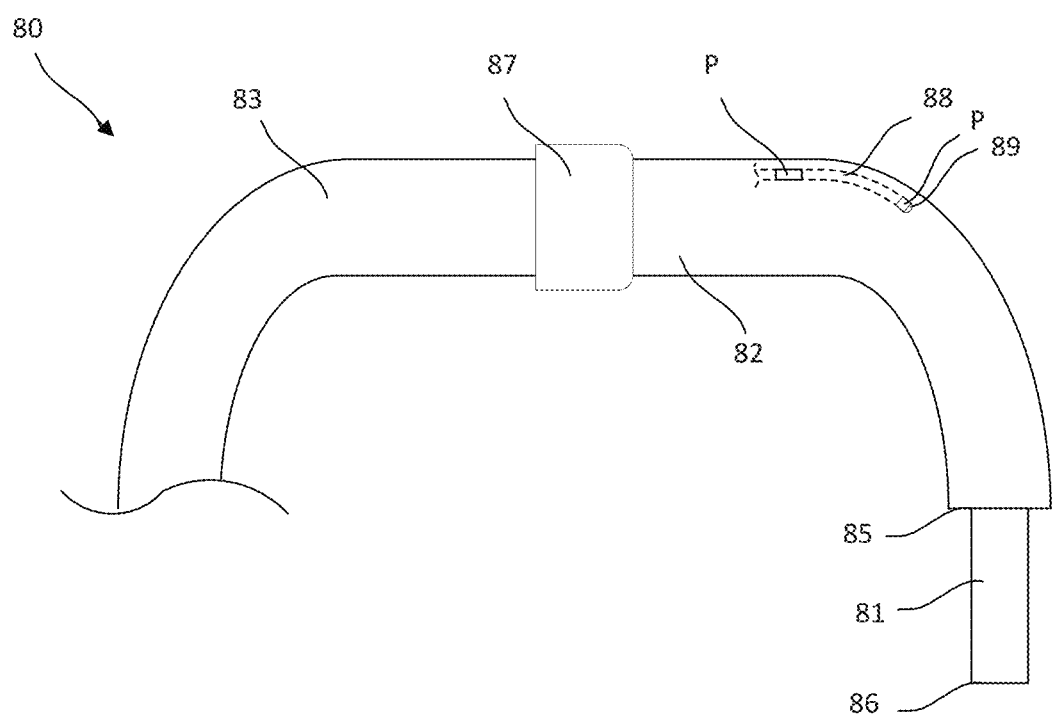
FIG. 21A illustrates a schematic of an example embodiment of a catheter for delivering an implant into the heart, configured with a pressure sensor.

Referring now to FIGS. 21A-21D, schematics of various example embodiments of a delivery system 80 for delivering an implant into the heart are illustrated. The steerable catheter 82 and the outer catheter 83 each have a central lumen which can be considered a delivery lumen. Referring now to FIG. 21A, a schematic of an example embodiment of a delivery system 80 for delivering an implant into the heart, is illustrated. This example embodiment is configured to have a pressure sensor within one of the delivery device's catheters or pusher. The delivery system 80 can include an implant delivering pusher tube or rod 81, a steerable catheter 82, and an outer catheter or sleeve 83. The steerable catheter 82 can extend out from the outer catheter's distal end 87, and the pusher tube or rod can extend outward from the steerable catheter's distal end 85. In one example embodiment, a valve implant, valve repair device, or other therapy is pushed out an end 85 of the steerable catheter 82 by a distal end 86 of the pusher tube or rod 81. In another example embodiment, the valve repair device or other therapy is initially positioned distally from the end 85 of the steerable catheter, inside the outer catheter 83 (i.e. not inside the steerable catheter). This allows the device to have a larger size, because it does not need to fit inside the steerable catheter 82. A pressure sensor P can be disposed in a lumen within the wall of any of the steerable catheter 82, the outer sleeve or catheter 83, the pusher tube or rod 81, the actuation rod 112, or in a separate catheter disposed in a space between any two of the steerable catheter 82, the outer sleeve or catheter 83, the pusher tube or rod 81, and the actuation rod 112.

In the example embodiment of FIG. 21A, a pressure sensor lumen 88 can run along the length of the steerable catheter 82. The pressure sensor lumen 88 can be formed in the steerable catheter or can be a lumen of a separate catheter disposed in the steerable catheter. In the embodiment illustrated in FIG. 21A, the open distal end 89 of the lumen 88 can be along the length of the steerable catheter (i.e. not at the end 85 of the steerable catheter). The pressure sensor P can be at the port 89 to directly measure pressure of the blood. Reference character P' represents another example embodiment where the pressure sensor P' is upstream of the port 89, such that the pressure of the blood in the heart is measured indirectly through fluid in the pressure sensor lumen 88. The pressure sensor port 89 can be anywhere along the catheter in a location that is typically positioned in an atrium of the heart during a valve treatment procedure.

Figure 21B:
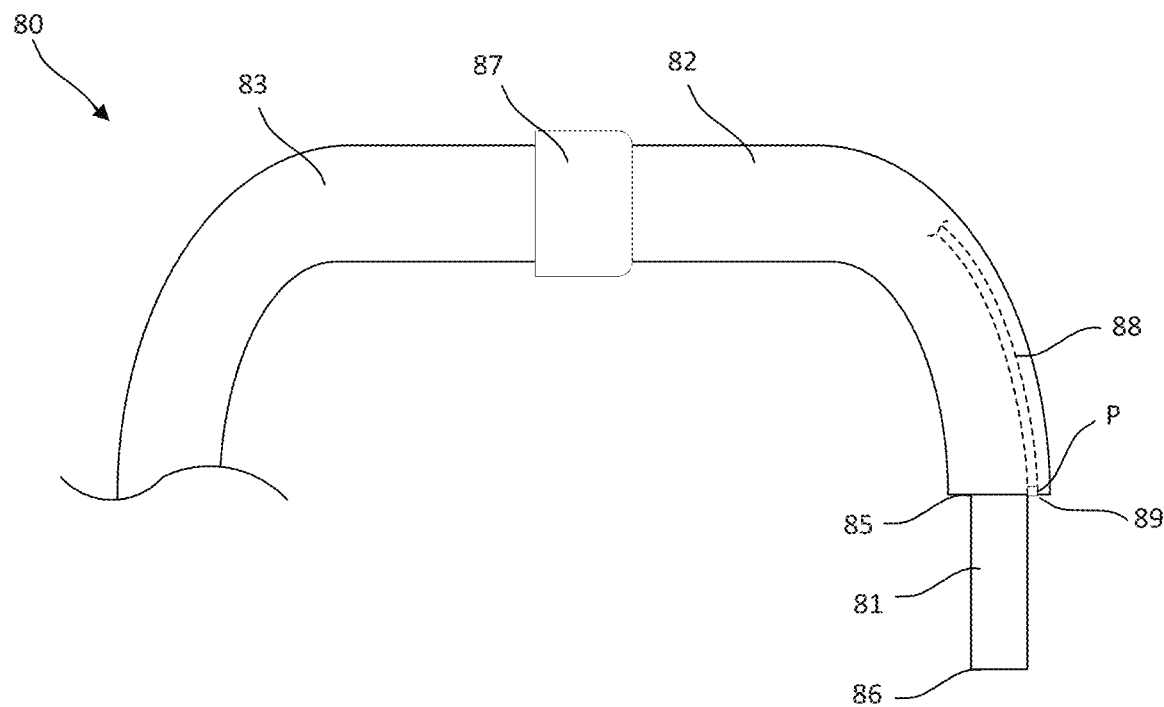
FIG. 21B illustrates a schematic of an example embodiment of a catheter for delivering an implant into the heart, configured with a pressure sensor.

Referring now to FIG. 21B, another example embodiment of a delivery system 80 for measuring intra-atrial pressure during delivery of a heart valve implant or repair without requiring a separately introduced catheter is depicted. The example embodiment of FIG. 21B is similar to FIG. 21A, except that the open distal end or pressure port 89 for the pressure monitoring lumen 88 is at the distal end 85 of the steerable catheter 82. In the embodiment illustrated by FIG. 21B, the pressure sensor P is positioned at the port 89 to directly measure the pressure of the blood.

Figure 21C:
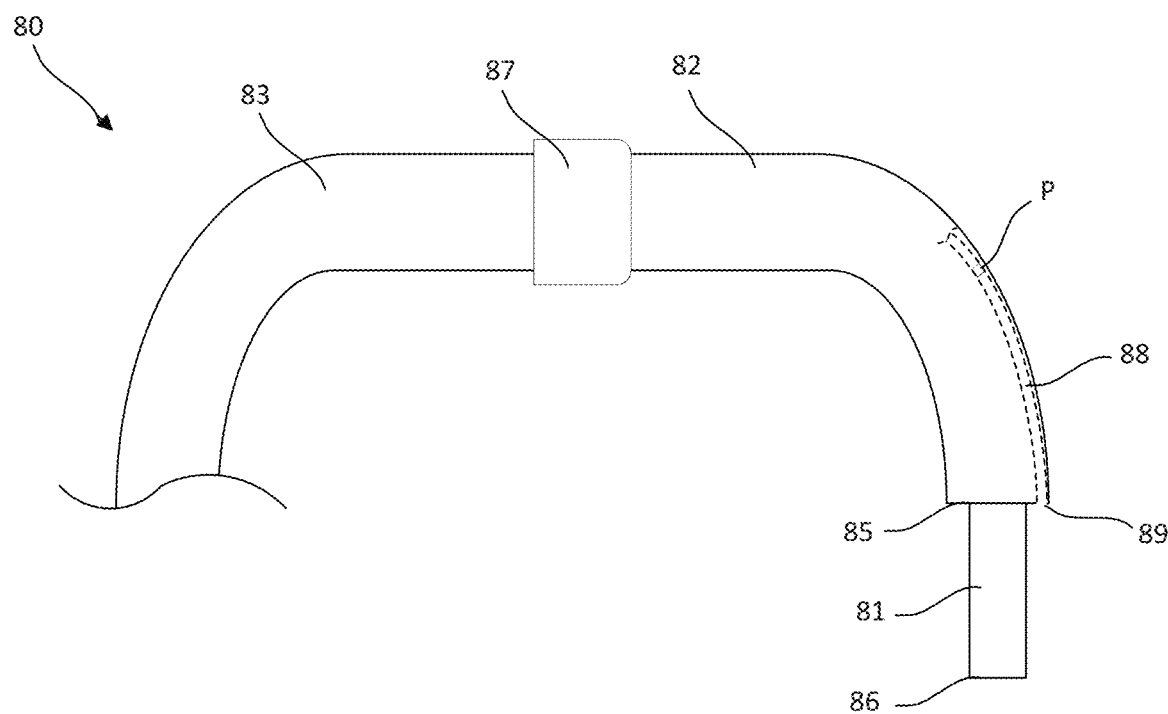
FIG. 21C illustrates a schematic of an example embodiment of a catheter for delivering an implant into the heart, configured with a pressure sensor.

Referring now to FIG. 21C, another example embodiment of a delivery system 80 for measuring intra-atrial pressure during delivery of a heart valve implant or repair without requiring a separately introduced catheter is depicted. In this example embodiment, the pressure sensor lumen 88 is optionally embedded in the wall of the steerable catheter 82. In the illustrated embodiment, the pressure sensor P is located proximal to the port 89 of the pressure sensor lumen.

However, the pressure sensor can be at the port 89 of the steerable catheter as mentioned above.

Figure 21D:
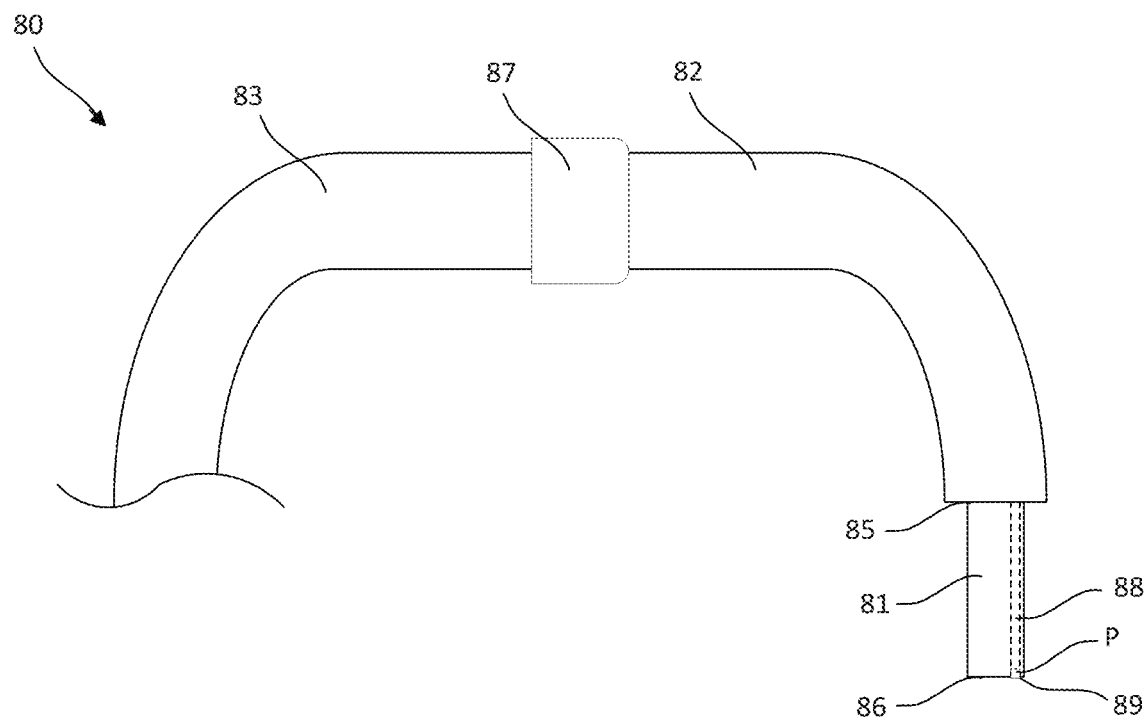
FIG. 21D illustrates a schematic of an example embodiment of a catheter for delivering an implant into the heart, configured with a pressure sensor.

Referring now to FIG. 21D, the pressure sensor lumen 88 can be embedded in the wall or disposed inside of the pusher rod or tube 81 and can have an open distal end or port 89 at the distal end of the pusher tube or rod. In some embodiments the opening or port 89 can be at any location along the pusher tube or rod 81 that extends from the steerable catheter 82. In example embodiments, the pressure sensor lumen can be fully embedded within a wall of the steerable catheter or pusher tube or rod, or it can be partially embedded in the wall and protrude toward a center of the catheter's lumen. In some embodiments, the lumens described herein can be defined by another catheter, which can be a pressure monitoring catheter, extending inside a lumen in the pusher 81. In some embodiments, a pressure measuring catheter with a lumen is in the space between the steerable catheter and pusher tube 81. In this embodiment, the pressure measuring catheter can optionally be fixed to the interior wall of the steerable catheter. In the example illustrated by FIG. 21D, the pressure sensor is positioned at the port 89. However, in some example embodiments, the pressure sensor P is positioned upstream of the port.

Figure 22A:
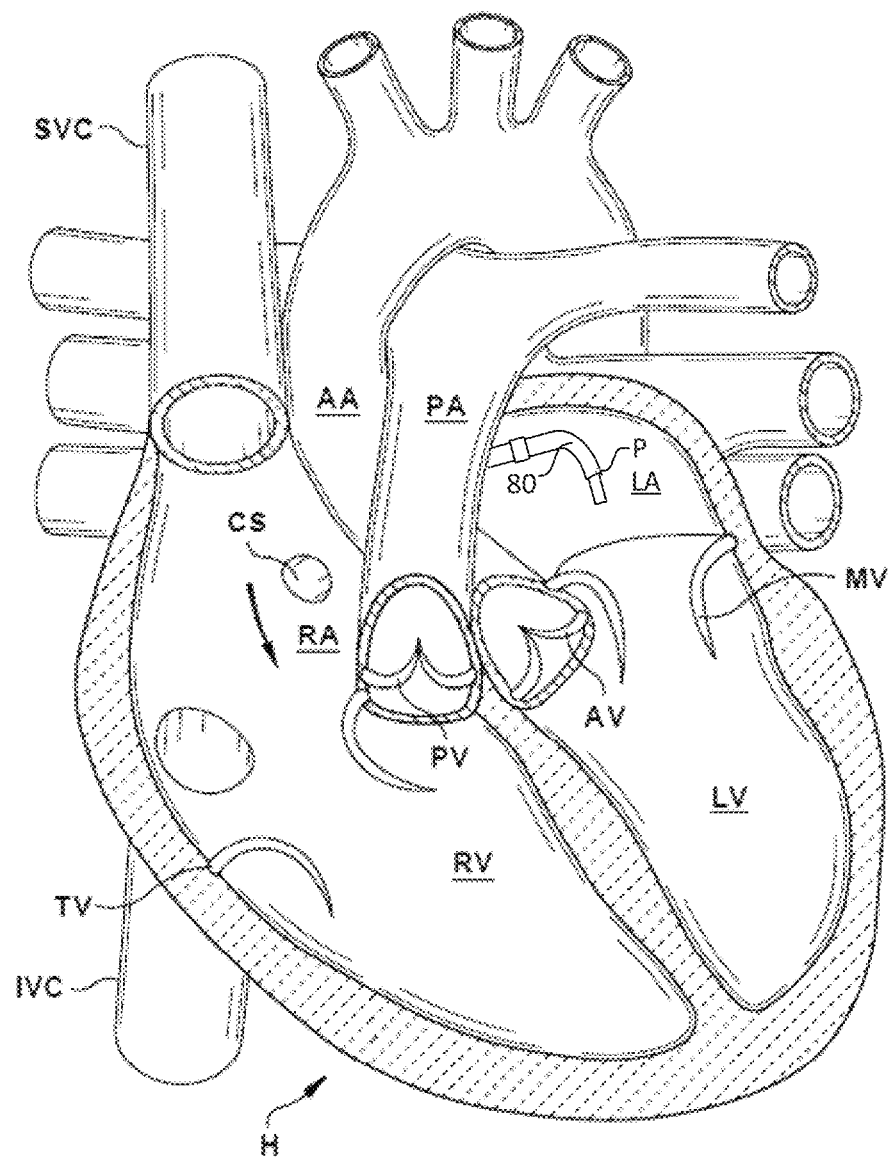
FIG. 22A illustrates a cutaway view of the human heart in a diastolic phase, having a delivery device of a replacement valve or valve repair device with a pressure sensor positioned within the left atrium.
Figure 22B:
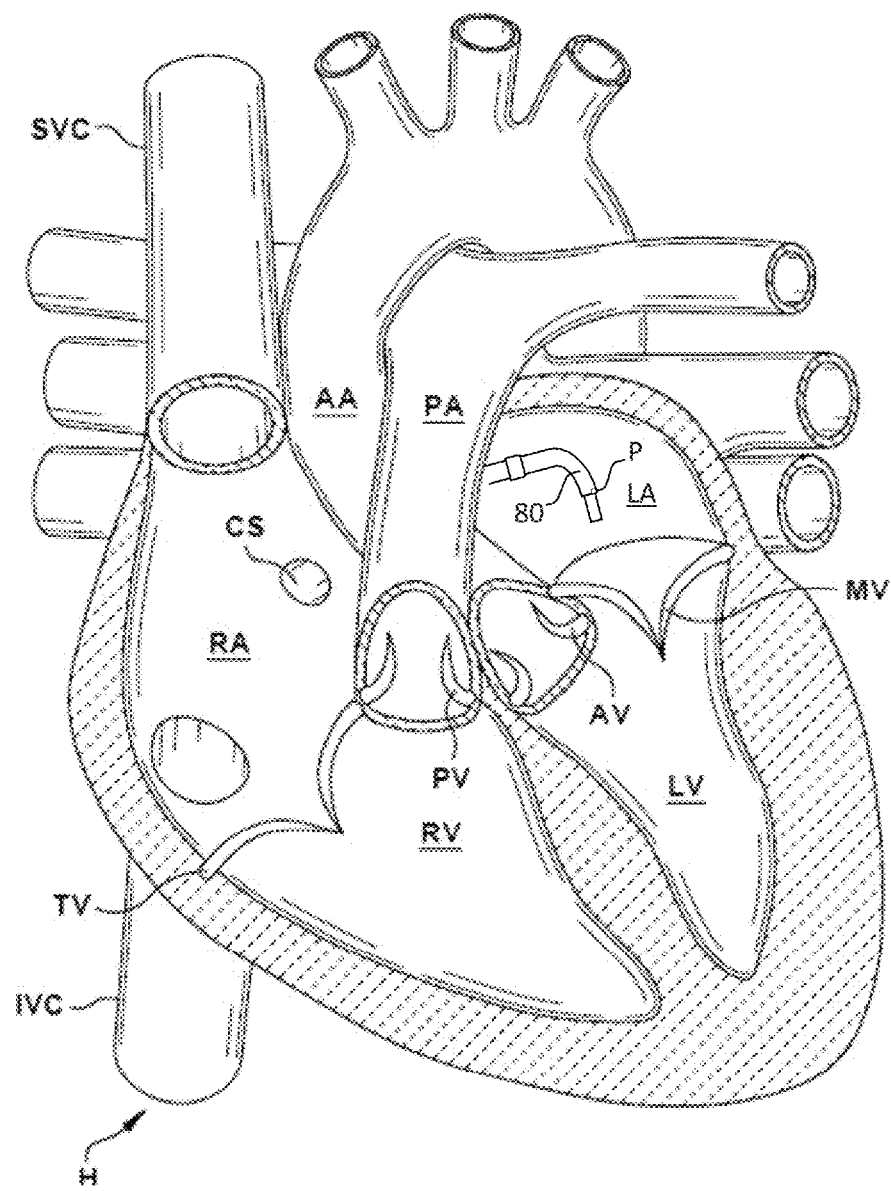
FIG. 22B illustrates a cutaway view of the human heart in a systolic phase, having a delivery device of a replacement valve or valve repair device with a pressure sensor positioned within the left atrium.

Referring now to FIGS. 22A and 22B, a cutaway view of the human heart H is illustrated in diastole and systole, respectively. In the left atrium LA is a delivery system 80 with a pressure sensor P within it. The pressure sensor can record a pressure in the left atrium during diastole, and another pressure in the left atrium during systole. The pressure sensor is not limited to measuring pressure in the left atrium and can also be used in the right atrium or one of the ventricles. FIGS. 8-20 illustrate an example of one of the many different types of valve therapies that can be delivered by the delivery system 80. The valve therapy is not shown in FIGS. 22A and 22B to simplify these two figures. A typical valve therapy comprises positioning and/or deploying a valve implant or valve repair device (see FIGS. 8-20) in the native valve of the heart, which can be the mitral valve or the tricuspid valve. However, the valve therapy is not limited to a replacement valve or a valve repair device; it can also be a docking coil with a valve implant, sutures or chordae replacement devices, annuloplasty devices, and/or other implants used to correct the function of a heart native valve. The delivery system can use a transvascular technique such as a trans-septal technique, but is not limited thereto; the delivery system can be delivered to an atria of the heart by any presently known and future-developed technique. When the valve implant or repair is in place, the pressure can be measured again to determine if a therapeutic effect has occurred, i.e., if a regurgitation or other heart valve defect has been repaired and/or improved.

Figure 23A:
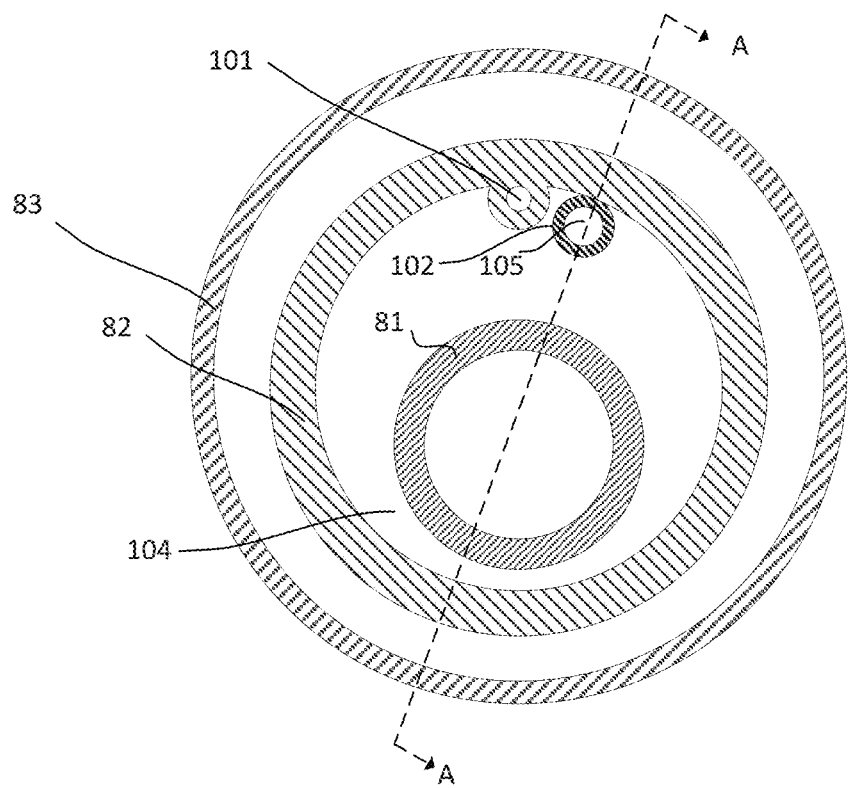
FIG. 23A illustrates a schematic sectional view of an example delivery system configured to include a pressure sensor in accordance with an example embodiment.
Figure 23B:
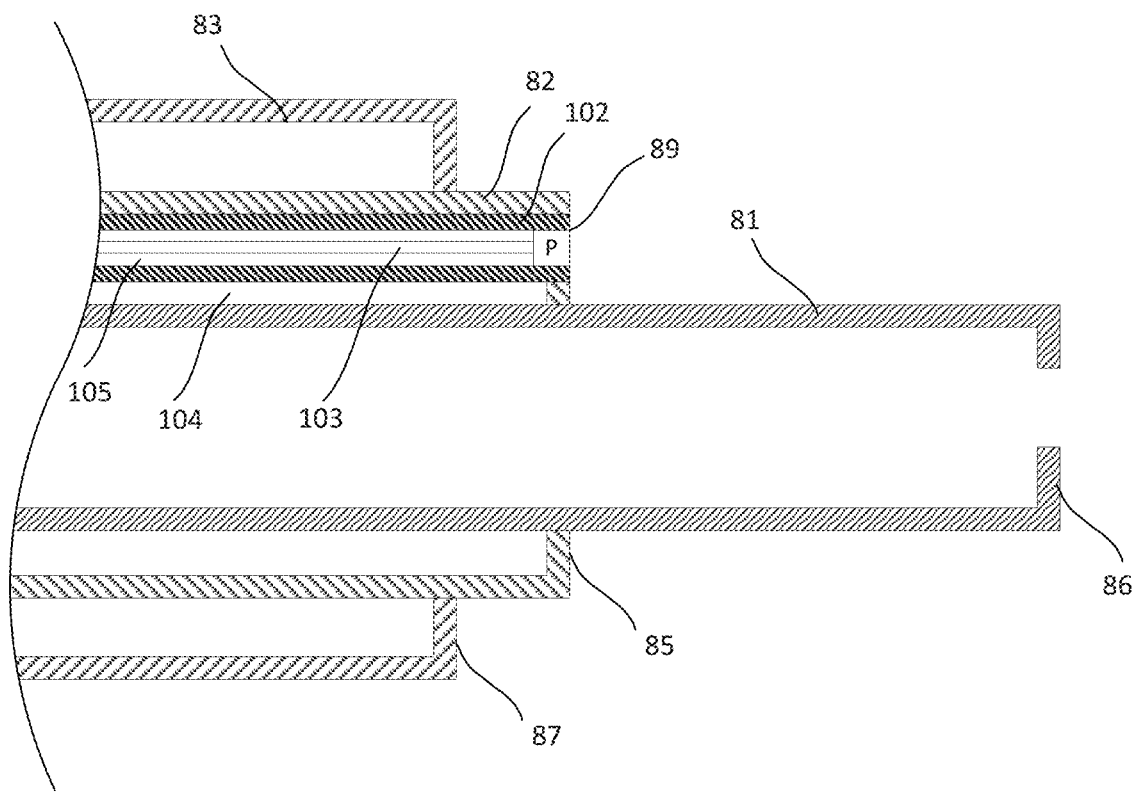
FIG. 23B illustrates a schematic cross section of the delivery system of FIG. 23A, taken along line A-A, and having a pressure sensor in accordance with an example embodiment.
Figure 23C:
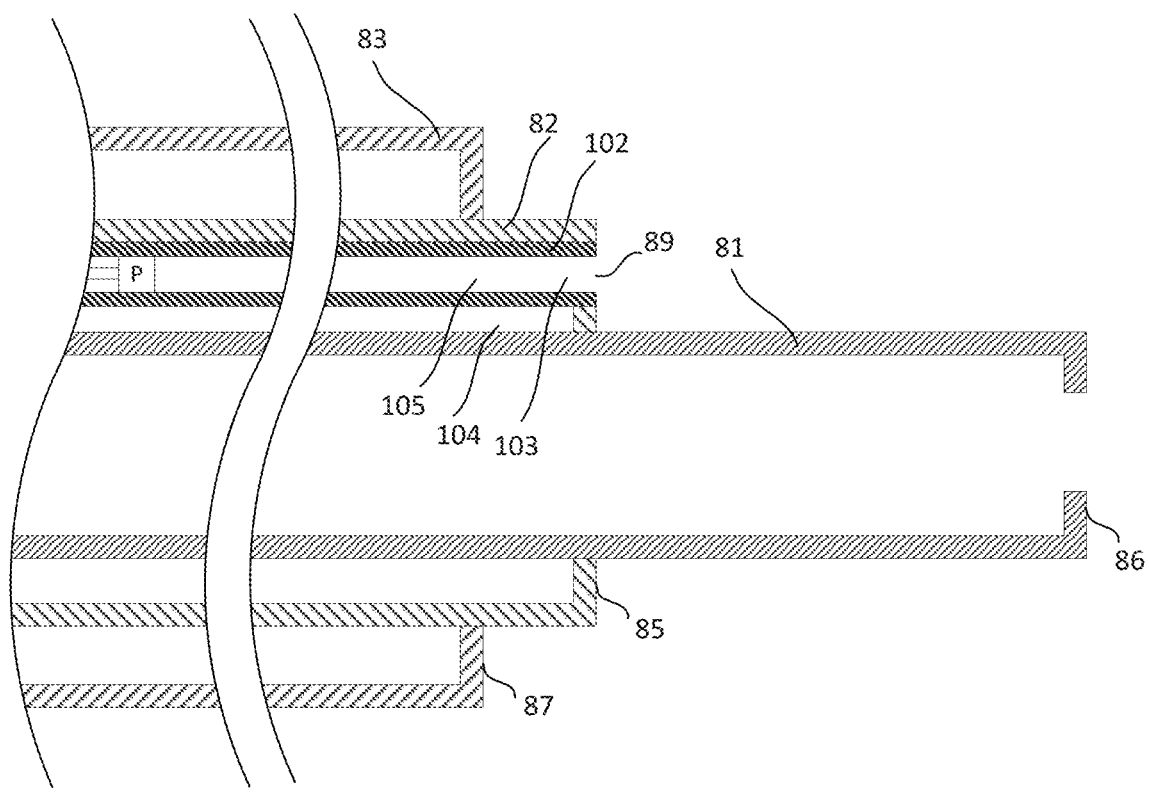
FIG. 23C illustrates a schematic cross section of the delivery system of FIG. 23A, taken along line A-A, and having a pressure sensor in accordance with an example embodiment.
Figure 23D:
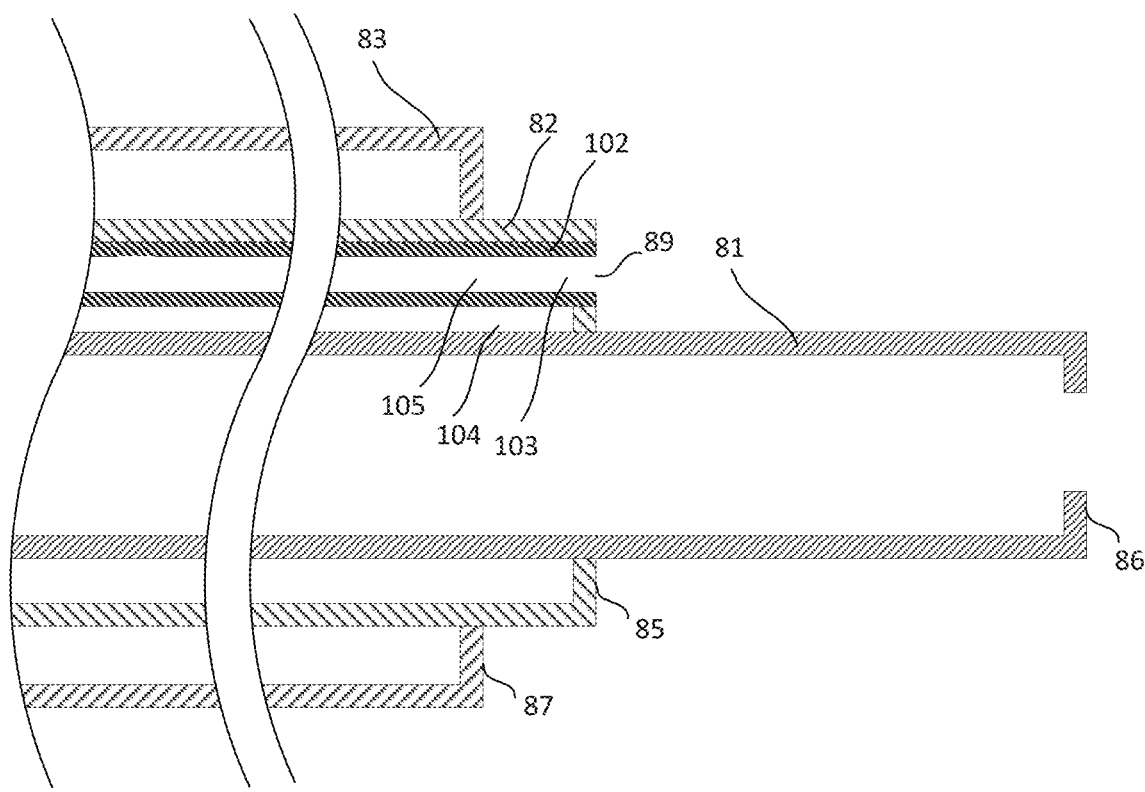
FIG. 23D illustrates a schematic cross section of the delivery system of FIG. 23A, taken along line A-A, and having a fluid filled lumen for measuring pressure in accordance with an example embodiment.

Referring now to FIGS. 23A-23C, schematics of example embodiments of a delivery system for the delivery of a valve implant or repair are illustrated. FIG. 23A illustrates an end view, having an implant pusher or catheter 81, a steerable catheter 82, and an outer sheath 83. The steerable catheter can have an integrated lumen, typically used for steering cables (not shown) that extend along at least a length of the steerable catheter. In some embodiments, an additional pressure sensor catheter 102 is positioned in the lumen 104 of the steerable catheter, adjacent to the interior surface of the steerable catheter wall. The pressure sensor catheter can have a lumen 105. The pressure sensor catheter 105 can have a pressure sensor in it (FIGS. 23B-C) or can be filled with a biocompatible fluid to measure the pressure (FIG. 23D). The pressure sensor catheter shown here is not limited to this location but can be positioned anywhere in the space between the pusher tube and the steerable catheter, such that sufficient flexibility of the steerable catheter 82 and delivery system 80 as a whole can still be achieved so that the valve implant or repair device can be implanted in a desired location.

FIG. 23B illustrates a cross section of the delivery system 80 taken along line A-A. In FIG. 23B the opening at the end 86 of the pusher tube 81 for the actuation rod 112 (See FIG. 10) is not shown, because the opening is offset from the cross-section plane A-A. In FIG. 23B, a pressure sensor P is positioned inside a distal end of the pressure sensor catheter lumen 105 and connected to a communication link 103, such as a wire or pair of wires. The communication link 103 can extend out a proximal end (not shown, outside the patient) to allow the pressure sensed at the pressure sensor P to be monitored outside the patient by monitoring equipment.

The pressure sensor P can be one of any of various pressure sensors. For example, the pressure sensor can be a piezo-electric sensor, a pressure-sensing probe, or a barometric pressure sensor. In the example embodiments described herein, the pressure sensor can be an electric pressure sensor that measures the pressure of fluid, which can be the blood in the left atrium of the heart or can be the pressure of the fluid, which can be a saline solution, in the pressure sensor lumen. The pressure sensor can be positioned to extend distally out of the end of the pressure sensor lumen 105 or the pressure sensor can be fully within the pressure lumen. The pressure sensor P can be positioned at any position along the length of the pressure sensor lumen 105. For example, the pressure sensor P can be flush or substantially flush with the port 89 or the pressure sensor P can be spaced proximally away from the port inside the pressure sensor lumen. In the illustrated example of FIG. 23B, the pressure sensor lumen distal end or port 89 is flush with the distal end of the steerable catheter. In some embodiments, the port 89 is spaced apart from the end of the steerable catheter. In some embodiments, the pressure sensor can be embedded in the wall of the catheter having the pressure sensor lumen or pressure sensor catheter lumen.

The pressure sensor catheter 102 can be fixedly connected to the interior wall of the steerable catheter by any means to secure catheter tubing together. The steerable catheter extends distally beyond the outer catheter 83. The pusher tube or rod extends even farther distally from the distal end of the steerable catheter. As the pusher tube or rod is what delivers a valve implant or repair device to the valve, it can be extendable from the end of the steerable catheter. The pusher tube or rod can extend past the distal end of the steerable catheter so that it can reach through the mitral valve (or tricuspid valve) towards the left ventricle to allow an operator to properly position the valve implant or repair device during its deployment. The pressure sensor can provide accurate measurements of pressure in the atrium when the delivery system is inserted such that the steerable catheter is still in the atrium, and not at the valve annulus or below, in the ventricle. In the example embodiment illustrated in FIG. 23B, the pressure sensor P is located at the distal end of the lumen and can detect the pressure of the fluid within the lumen at the distal end of the lumen. Because the distal end of the lumen can be open, the pressure exerted by the fluid in the lumen on the sensor will be the same as the pressure of the blood in the left atrium, because the pressure of the blood in the left atrium will push on the fluid in the lumen.

By having the pressure sensor in a pressure sensor lumen that fits within existing space in the steerable catheter main lumen, the number of catheterizations of the heart needed to implant a valve device and record pressures to measure its efficacy is reduced, thereby reducing noise that could affect pressure measurements.

Referring to FIG. 23C, a schematic of a cross section taken along line A-A of FIG. 23A, of an example embodiment of a delivery system 80 with a pressure sensor is illustrated. In FIG. 23C the opening at the end 86 of the pusher tube 81 for the actuation rod 112 (See FIG. 10) is not shown, because the opening is offset from the cross-section plane A-A. In FIG. 23C, the pressure sensor is in accordance with an example embodiment. In this embodiment, the pressure sensor is a fluid filled pressure sensor P located more proximal than that of FIG. 23A. In FIG. 23C, the pressure sensor catheter within the lumen of the steerable catheter is filled with a fluid. The fluid can be saline or another biocompatible fluid. Because this pressure sensor catheter is within a delivery system that is already inserted in the heart, an additional catheter is not required to be inserted to take a pressure measurement. The noise in the atrium is reduced by the separate lumen 102 and the pressure measurement can provide better feedback to the operator regarding the efficacy of the valve implant or repair being administered. Noise reduced is that which could otherwise be caused by movement, increased pressure, and additional disturbances to the blood flow in the left atrium, that could be caused by, for example, another catheter in the left atrium.

Referring now to FIG. 23D, a schematic of a cross-section taken along line A-A of FIG. 23A, of another example embodiment of a delivery system 80 for measuring pressure in a heart chamber is illustrated. In FIG. 23DF the opening at the end 86 of the pusher tube 81 for the actuation rod 112 (See FIG. 10) is not shown, because the opening is offset from the cross-section plane A-A. In FIG. 23D, the pressure sensor catheter lumen 105 is filled with a fluid, which can be saline, and the pressure of the fluid is measured by a monitoring system. The monitoring system can be connected to the lumen 105 and/or fluid therein through either the flush port on the handle or a separate port on the handle designed for the introduction of a pressure sensor, as with the other example embodiments described herein. In this embodiment, there is no pressure sensor P positioned within the lumen 105 to measure the pressure, electronically or otherwise. Instead, the pressure of the fluid in the lumen 105 is measured with the monitoring system. The pressure of the fluid in the lumen remains consistent throughout the lumen, and because the distal end of the lumen is open to the left atrium, the pressure exerted by the fluid in the lumen will be the same as the pressure of the blood in the left atrium.

The pressure can be measured using fluid instead of a pressure sensor P in any of the example embodiments described herein. This includes the embodiments having a pressure sensor lumen 88 embedded within a wall of a catheter, and also includes some embodiments having a pressure sensor catheter lumen 105. The pressure can be measured in the same way as it is measured with regard to the embodiment of FIG. 23D.

An example embodiment can be to have the pressure sensor P embedded in the wall of any catheter that surrounds a fluid filled lumen. The catheter wall can be that of the pusher tube or rod 81, the steerable catheter 82, the pressure sensor catheter 102, and/or the actuation rod 112 (See FIG. 10). The fluid filled lumen can be the pressure catheter lumen 105 or the pressure sensor lumen 88.

Figure 24A:
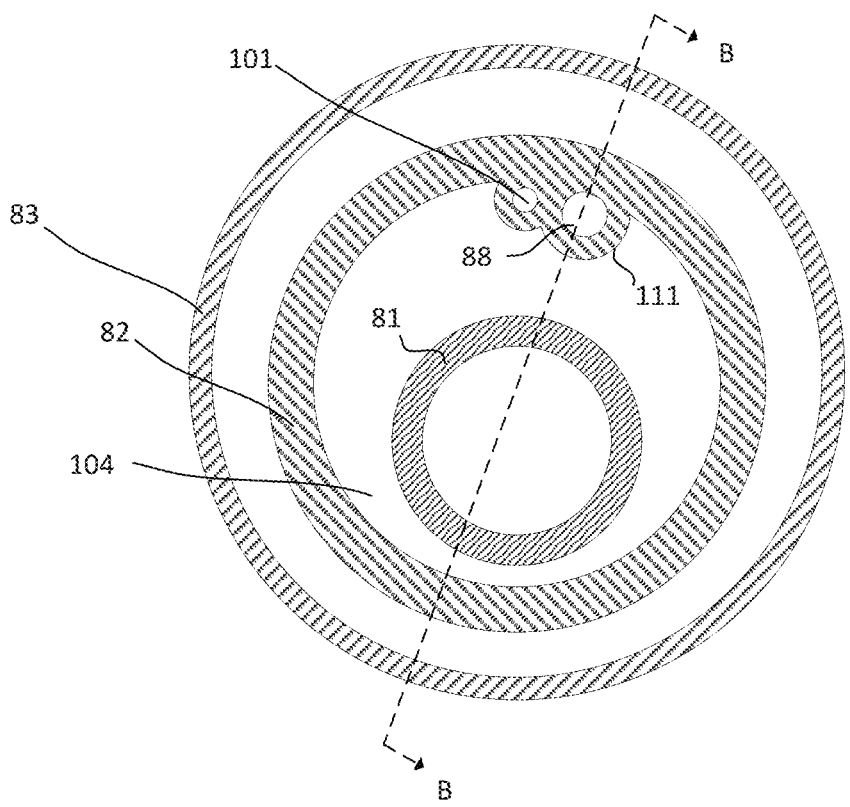
FIG. 24A illustrates a schematic sectional view of an example delivery system configured to include a pressure sensor in accordance with an example embodiment.
Figure 24B:
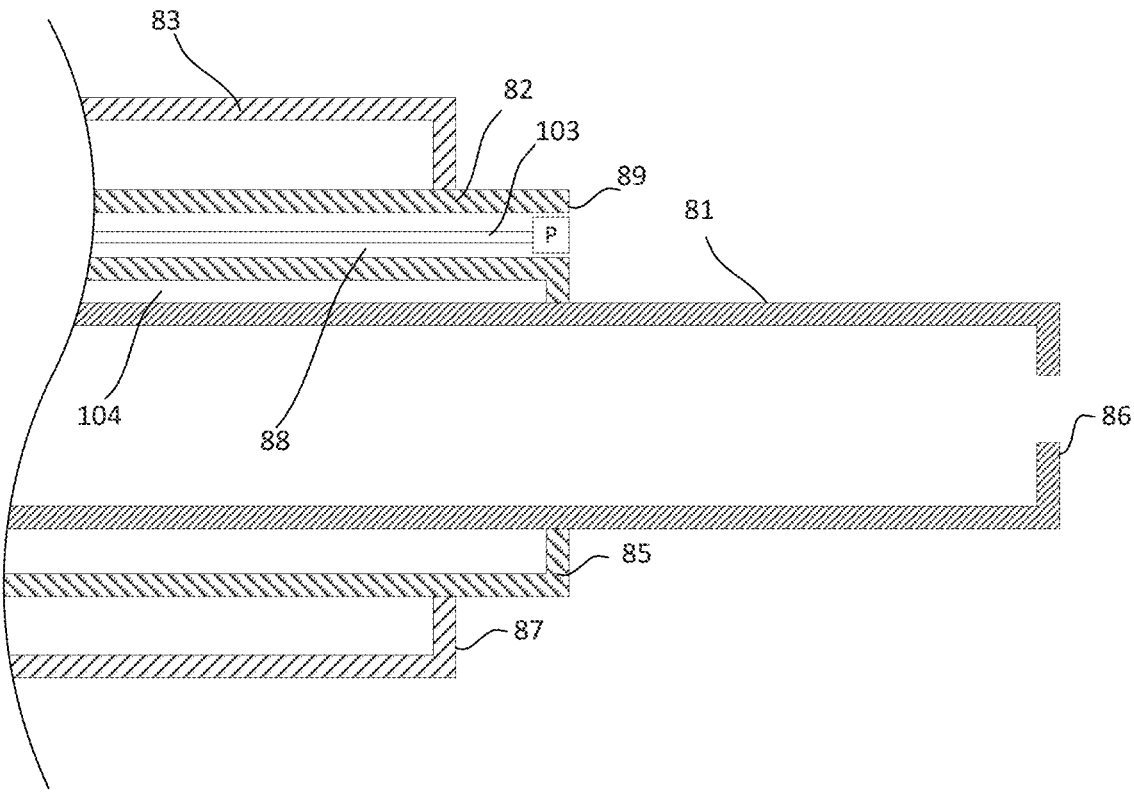
FIG. 24B illustrates a schematic cross section of the delivery system of FIG. 24A, taken along line B-B, and having a pressure sensor in accordance with an example embodiment.
Figure 24C:
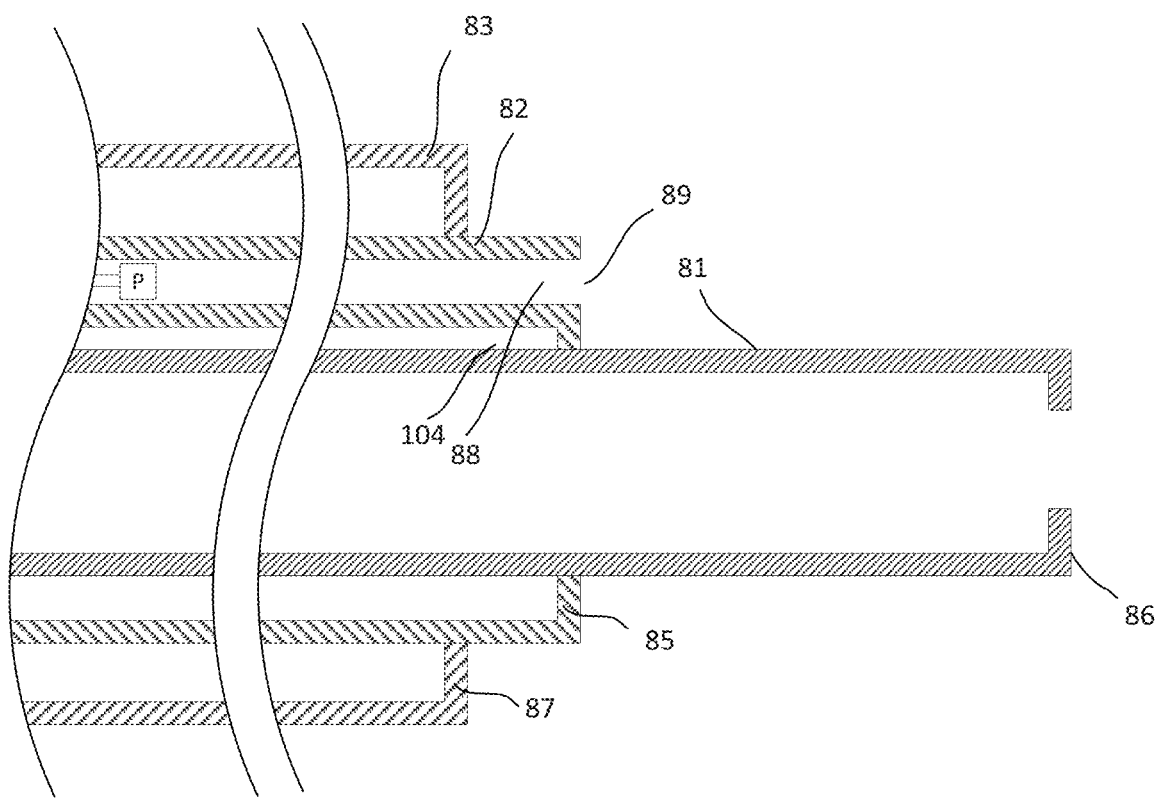
FIG. 24C illustrates a schematic cross section of the delivery system of FIG. 24A, taken along line B-B, and having a pressure sensor in accordance with an example embodiment.

Referring now to FIGS. 24A-24C, a schematic of an example embodiment of a delivery system for the delivery of a valve device is illustrated. FIG. 24A illustrates an end view, having a pusher tube or rod 81, a steerable catheter 82, and an outer sheath 83. In this embodiment, an additional pressure sensor lumen 88 is integrated in the wall of the steerable catheter. The pressure sensor lumen can bump out into the central lumen 104 of the steerable catheter as shown in FIG. 24A, or it can be flush within the wall of the steerable catheter. The integrated pressure sensor lumen can be adjacent to the integrated steerable catheter lumen as illustrated in FIG. 24A, or it can be spaced apart from it.

FIG. 24B illustrates a cross section of the delivery system 80 taken along line B-B. In FIG. 24B the opening at the end 86 of the pusher tube 81 for the actuation rod 112 (See FIG. 10) is not shown, because the opening is offset from the cross-section plane B-B. In FIG. 24B, a pressure sensor P is positioned inside a distal end of the pressure sensor lumen 88 of the steerable catheter 82 and is held in place at least by a connecting link 103. As with the example embodiment described herein with respect to FIGS. 23A-23B, the pressure sensor can be an electric pressure sensor (or other type of pressure sensor). The pressure sensor can be positioned to extend distally out of the end of the pressure sensor lumen 88 or it can be fully within the pressure lumen. The pressure sensor lumen distal end 89 can be flush with the distal end of the steerable catheter in this example embodiment but is not limited to such a length. The steerable catheter extends distally beyond the outer catheter 83. The pusher tube or rod extends even farther distally from the distal end of the steerable catheter. As the pusher tube or rod is what delivers a valve implant or repair device to the valve, it can be extendable from the end of the steerable catheter. The pusher tube or rod can extend past the distal end of the steerable catheter so that it can reach through the mitral valve (or tricuspid valve) towards the left ventricle to allow an operator to properly position the valve implant or valve repair device during its deployment. The pressure sensor can provide accurate measurements in the atrium when the delivery system is inserted such that the steerable catheter is still in the atrium, and not at the valve annulus or in the ventricle.

Referring to FIG. 24C, a schematic of a cross section taken along line B-B of FIG. 24A, of another example embodiment of a delivery system 80 with a pressure sensor is illustrated. In FIG. 24C the opening at the end 86 of the pusher tube 81 for the actuation rod 112 (See FIG. 10) is not shown, because the opening is offset from the cross-section plane B-B. In FIG. 24C, the pressure sensor is in accordance with another example embodiment. In this embodiment, the pressure sensor is a fluid filled pressure sensor lumen, having a pressure sensor P at a more proximal location within the pressure sensor lumen, which is described in greater detail above. In FIG. 24C, the lumen 104 of the steerable catheter is filled with a fluid, as described above. Because this example embodiment of a pressure sensor catheter is within a delivery system that is already implanted in the heart, an additional catheter is not required to be inserted to take a pressure measurement. Therefore, the noise in the atrium is reduced and the pressure measurement can provide better feedback to the operator regarding the efficacy of the valve implant or repair device being administered.

Figure 25A:
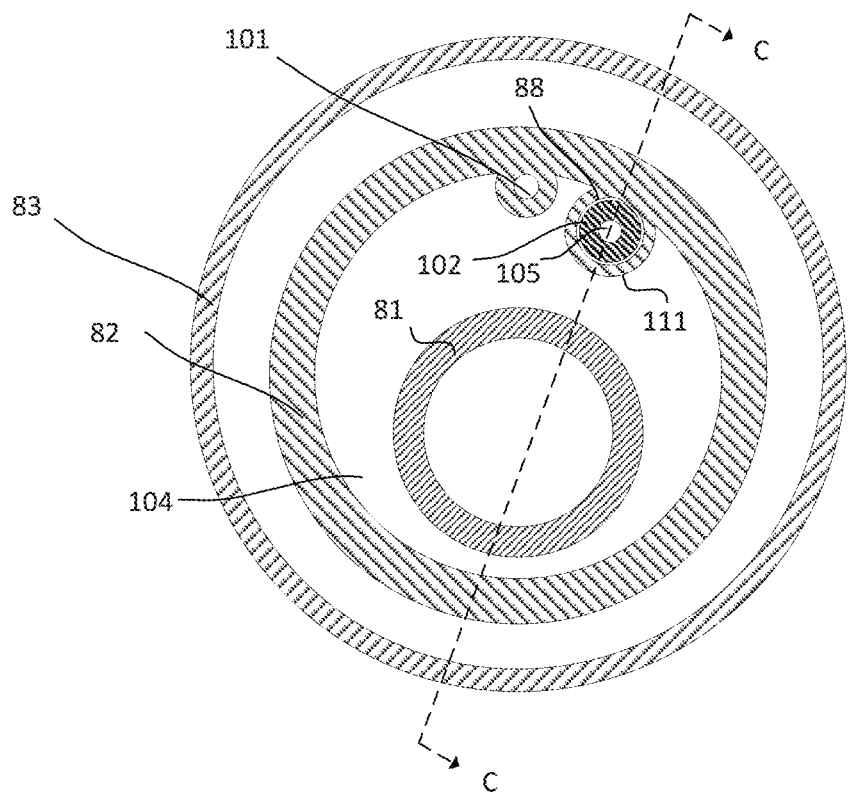
FIG. 25A illustrates a schematic end view of an example delivery system configured to include a pressure sensor in accordance with an example embodiment.
Figure 25B:
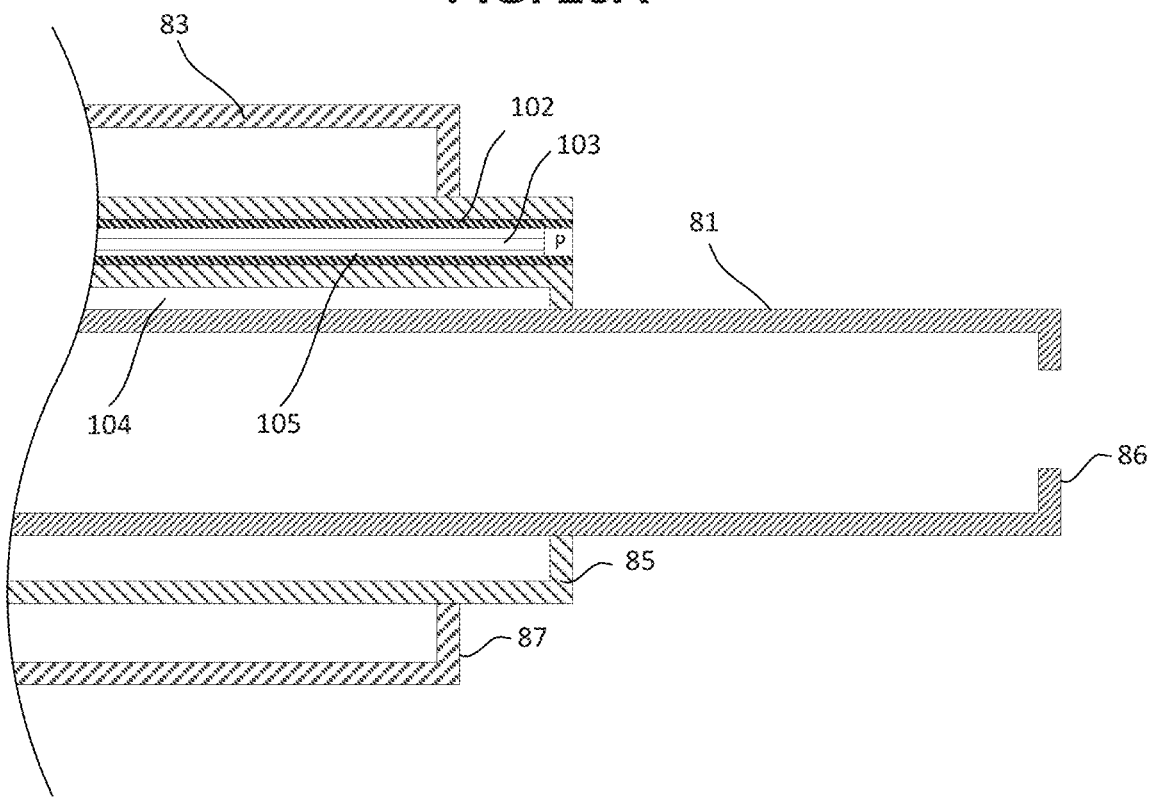
FIG. 25B illustrates a schematic cross section of the delivery system of FIG. 25A, taken along line C-C, and having a pressure sensor in accordance with an example embodiment.
Figure 25C:
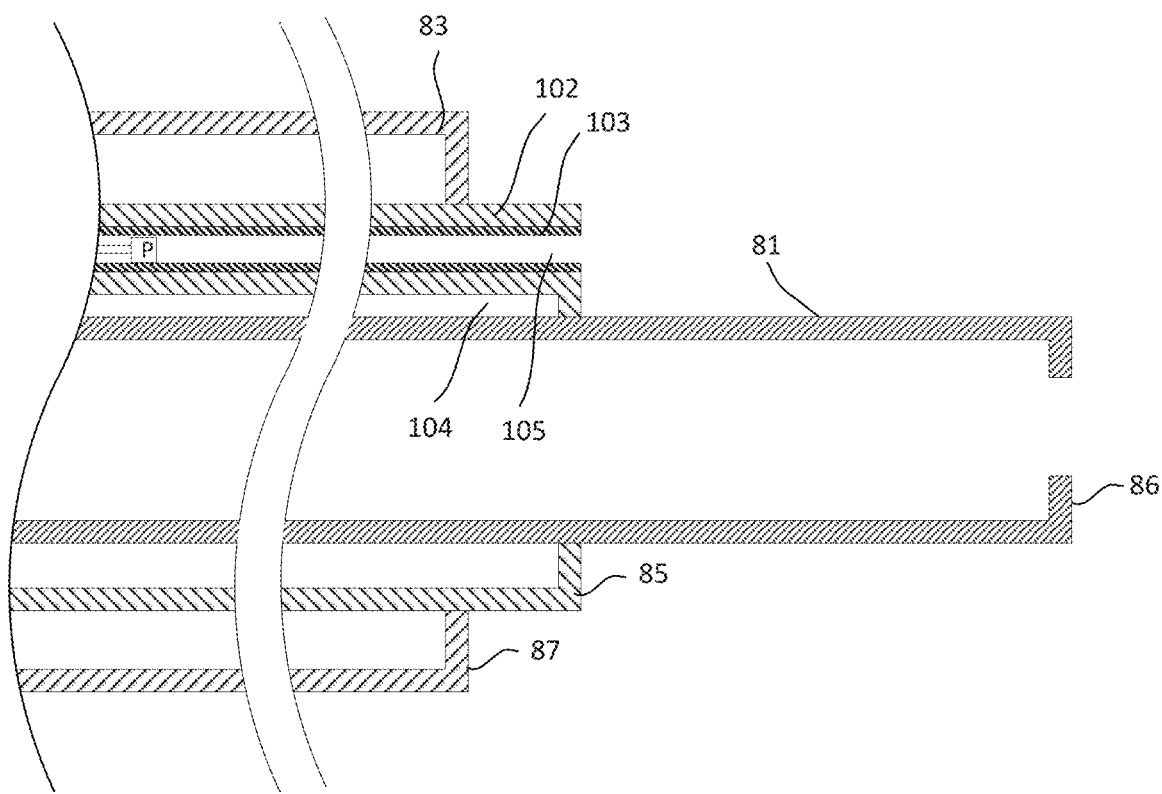
FIG. 25C illustrates a schematic cross section of the delivery system of FIG. 25A, taken along line C-C, and having a pressure sensor in accordance with an example embodiment.

Referring now to FIGS. 25A-25C, schematics of an example embodiment of a delivery system for the delivery of a valve implant or repair device are illustrated. FIG. 25A illustrates an end view, having a pusher tube or rod 81, a steerable catheter 82, and an outer sheath 83. The steerable catheter can have an integrated lumen as described above. The steerable catheter can have another integrated lumen 88. In this embodiment, an additional pressure sensor catheter 102 is positioned in the additional lumen 88 of the steerable catheter, adjacent to the interior surface of the steerable catheter wall. The pressure sensor catheter can have its own lumen 105. The pressure sensor lumen can bump out into the central lumen 104 of the steerable catheter as shown in FIG. 25A, or it can be flush within the wall of the steerable catheter. The integrated pressure sensor lumen can be adjacent to the integrated steerable catheter lumen as illustrated in FIG. 25A, or it can be spaced apart from it. The additional lumen within the steerable catheter shown in FIG. 25A is not limited to the locations described herein but can be positioned anywhere at least partially embedded in the wall of the steerable catheter, such that sufficient flexibility of the steerable catheter and delivery system as a whole can still be achieved so that the valve therapy can be implanted in a desired location.

FIG. 25B illustrates a cross section of the delivery system 80 taken along line C-C. In FIG. 25B the opening at the end 86 of the pusher tube 81 for the actuation rod 112 (See FIG. 10) is not shown, because the opening is offset from the cross-section plane C-C. In FIG. 25B, a pressure sensor P is positioned inside a distal end of the pressure sensor lumen 105 and can be held in place by an optional connecting link 103. The pressure sensor can be an electric pressure sensor or other sensor. The pressure sensor can be positioned to extend distally out of the end of the pressure sensor catheter lumen 105 or it can be fully within the pressure lumen. The pressure sensor catheter lumen distal end 89 is flush with the distal end of the steerable catheter in this example embodiment but is not limited to such a length. The pressure sensor catheter 102 can be fixedly connected to the interior wall of the steerable catheter lumen 104 by any means to secure catheter tubing together. In another embodiment, the pressure sensor catheter can be slidably positioned in the steerable catheter lumen 104. The steerable catheter extends distally beyond the outer catheter 83. The pusher tube or rod 86 extends even farther distally from the distal end of the steerable catheter. As the pusher tube or rod is what delivers a valve implant or repair to the valve, it can be extendable from the end of the steerable catheter. The pusher tube or rod can extend past the distal end of the steerable catheter so that it can reach through the mitral valve (towards the left ventricle) to allow an operator to properly position the valve implant or repair during its deployment. The pressure sensor can provide accurate measurements in the atrium when the delivery system is inserted such that the steerable catheter is still in the atrium, and not at the valve annulus or in the ventricle.

Referring to FIG. 25C, a schematic of a cross section taken along line C-C of FIG. 25A, of another example embodiment of a delivery system 80 with a pressure sensor is illustrated. In FIG. 25C the opening at the end 86 of the pusher tube 81 for the actuation rod 112 (See FIG. 10) is not shown, because the opening is offset from the cross-section plane C-C. In this example embodiment, the pressure sensor is a fluid filled pressure sensor lumen, having a pressure sensor P at a more proximal location within the pressure sensor lumen, which is described in greater detail above. Because this example embodiment of a pressure sensor catheter is within a delivery system that is already implanted in the heart, an additional catheter is not required to be inserted to take a pressure measurement. Therefore, the noise in the atrium is reduced and the pressure measurement can provide more reliable feedback to the operator regarding the efficacy of the valve implant or repair being administered.

Figure 26A:
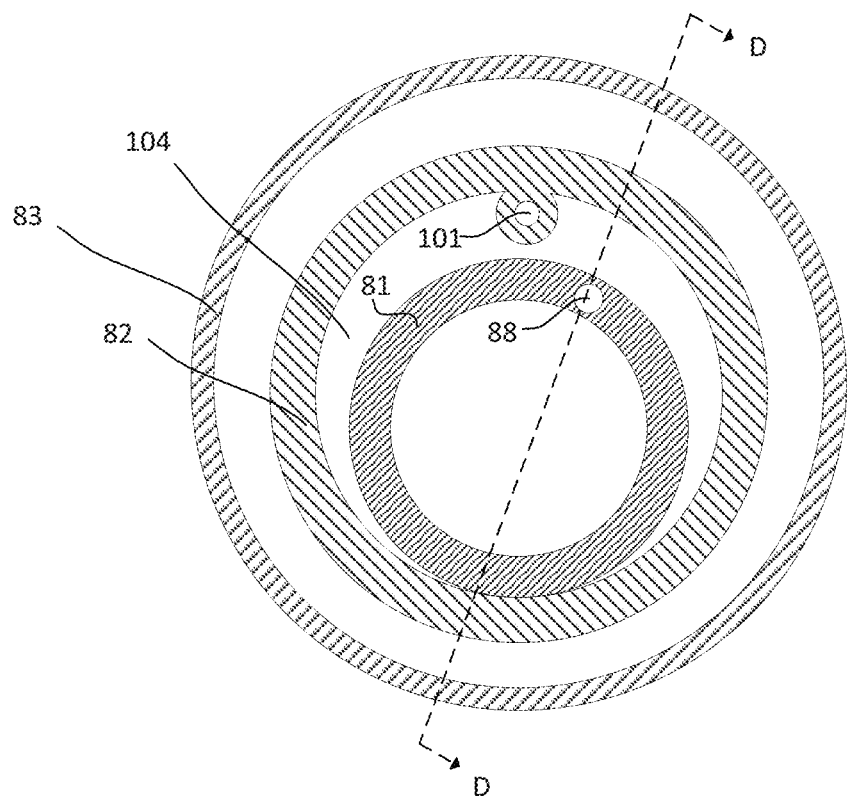
FIG. 26A illustrates a schematic sectional view of an example delivery system configured to include a pressure sensor in accordance with an example embodiment.
Figure 26B:
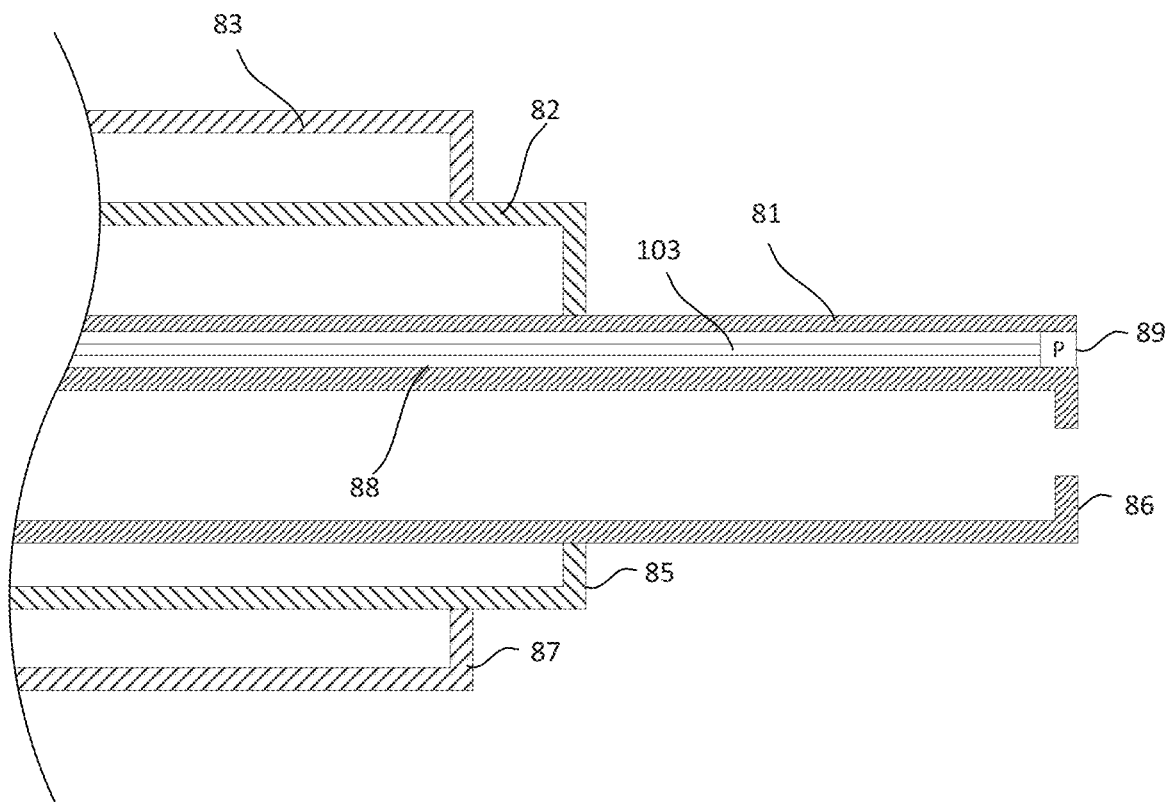
FIG. 26B illustrates a schematic cross section of the delivery system of FIG. 26A, taken along line D-D, and having a pressure sensor in accordance with an example embodiment.
Figure 26C:
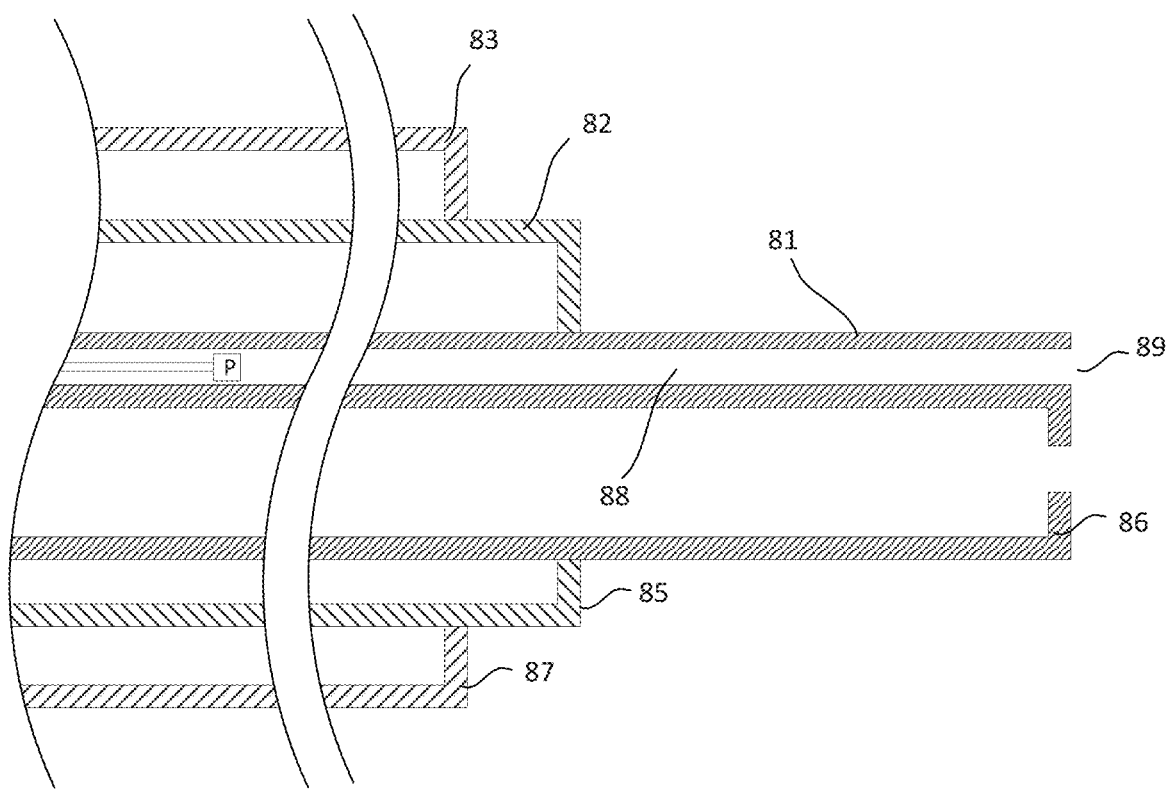
FIG. 26C illustrates a schematic cross section of the delivery system of FIG. 26A, taken along line D-D, and having a pressure sensor in accordance with an example embodiment.

Referring now to FIGS. 26A-26C, schematics of an example embodiment of a delivery system for the delivery of a valve implant or repair device are illustrated. FIG. 26A illustrates an end view, having a pusher rod or tube 81, a steerable catheter 82, and an outer sheath 83. In FIG. 26B the opening at the end 86 of the pusher tube 81 for the actuation rod 112 (See FIG. 10) is not shown, because the opening is offset from the cross-section plane C-C. In this embodiment, an additional pressure sensor lumen 88 is integrated in the wall of the pusher rod or tube 81. The pressure sensor lumen can be flush within the wall of the pusher rod or tube 81 as shown in FIG. 26A, or it can bump out into a central lumen of the pusher tube or rod 81.

FIG. 26B illustrates a cross section of the delivery system 80 taken along line D-D. In FIG. 24B, a pressure sensor P is positioned inside a distal end of the pressure sensor lumen 88 of the pusher rod or tube 81 and can be held in place at least by a connecting link 103. As with the example embodiment described herein with respect to FIGS. 23A-23B, the pressure sensor can be positioned extending distally out of the end of the pressure sensor lumen 88 or it can be fully within the pressure sensor lumen. The pressure sensor lumen can be filled with a biocompatible fluid such as saline. The pressure sensor lumen distal end 89 is flush with the distal end of the pusher rod or tube 81 in this example embodiment but is not limited to such a length. The steerable catheter extends distally beyond the outer catheter 83. The pusher tube or rod extends even farther distally from the distal end of the steerable catheter. As the pusher tube or rod is what delivers a valve implant or repair device to the valve, it can be extendable from the end of the steerable catheter. The pusher tube or rod can extend past the distal end of the steerable catheter so that it can reach through the mitral valve (or tricuspid valve) towards the left ventricle to allow an operator to properly position the valve implant or repair during its deployment. As with the other example embodiments described herein, the pressure sensor can measure an accurate atrial pressure when its opening to the exterior of the delivery system is located in the atrium. The pressure sensor can provide accurate measurements in the atrium when the delivery system is inserted such that the pusher tube or rod is still in the atrium, and not at the valve annulus or in the ventricle.

As with the other integrated lumen embodiments, having the pressure sensor in a pressure sensor lumen integrated within the pusher rod or tube 81, the number of catheterizations of the heart needed to implant a valve implant or repair and record pressures to measure its efficacy is reduced, thereby reducing noise that could affect pressure measurements.

Referring to FIG. 26C, a schematic of a cross section taken along line D-D of FIG. 26A, of another example embodiment of a delivery system 80 with a pressure sensor is illustrated. In FIG. 26C the opening at the end 86 of the pusher tube 81 for the actuation rod 112 (See FIG. 10) is not shown, because the opening is offset from the cross-section plane C-C. In FIG. 26C, the pressure sensor is in accordance with another example embodiment. In FIG. 26C, the pressure sensor is a fluid filled pressure sensor lumen, having a pressure sensor P at a more proximal location within the pressure sensor lumen, which is described in greater detail above. Because this pressure sensor catheter is within a delivery system that is already implanted in the heart, an additional catheter is not required to be inserted to take a pressure measurement. Therefore, the noise in the atrium is reduced and the pressure measurement can provide better feedback to the operator regarding the efficacy of the valve implant or repair device.

In an example embodiment having a pressure sensor catheter within a steerable catheter lumen as illustrated in FIGS. 23A-23C, the pressure can be measured according to the following method. In FIG. 23B, the pressure sensor can be an electric pressure sensor. The pressure sensor in FIG. 23B is accessible to the left atrium because it is positioned at the distal end of the pressure sensor catheter which can be flush with the distal end of the steerable catheter, and the distal end of at least the pressure sensor catheter is open to the atrium. In one embodiment, the pressure sensor can be connected to a monitoring system (not shown) through a flush port on the handle of the delivery system. In another embodiment, the pressure sensor can be connected to a monitoring system through a separate port on the handle, where the separate port is for the introduction of the pressure sensor catheter or direct attachment of the pressure monitor. As explained above, the pressure sensor in FIG. 23B can be positioned in other locations, too.

In the example embodiment of FIG. 23B, a baseline pressure measurement can be taken when the steerable catheter distal end 86 is in the left atrium, before the valve implant or repair device is delivered. The pressure of the fluid within the pressure sensor lumen can be electronically taken and can be recorded and/or displayed in the monitoring system. As explained above, this pressure is about the same or the same as the pressure in the left atrium of the heart. This baseline pressure measurement can be recorded during systole and/or diastole, and a measurement during and/or at the end of systole can be determinative of whether regurgitation is occurring. The valve implant or repair device can then be delivered, but before withdrawing the delivery system, the distal end of the steerable catheter can be positioned in the left atrium again, and another pressure measurement can be taken. This pressure measurement can determine whether the pressure has changed now that the valve implant or repair device has been positioned in the native valve. The pressure measurement should be taken at the same point(s) in the cardiac cycle (during systole and/or at the end of systole) as the baseline measurement. The pressure measurement taken(s) by the pressure sensor at this time should be lower than the baseline pressure measurement, due to correction of the regurgitation of blood back into the atrium. The pressure can be measured before the valve implant or repair device is disconnected from the delivery catheter, so that it can be repositioned if an operator so requires, to achieve effective placement. If a valve implant or repair is effectively implanted, the blood will flow from the left ventricle to the aorta instead of back through the mitral valve. The pressure can be measured as many times as needed. The pressure can also be measured continuously.

In some example embodiments of a method of measuring atrial pressure with a fluid-filled pressure sensor of FIG. 23C, the pressure sensor lumen can be filled with a fluid such as saline or other biocompatible fluid known by one of ordinary skill in the art to be used in fluid filled atrial pressure monitors. The pressure sensor P can be at a more proximal location along the length of the catheter delivery system. A baseline pressure measurement can be taken when the steerable catheter distal end 86 is in the left atrium, before the valve implant or repair device is delivered. This baseline pressure measurement can be recorded at any time, such as during or at the end of systole, as explained above. The valve implant or repair device can then be delivered, but before withdrawing the delivery system, the distal end of the steerable catheter can be positioned in the left atrium, and another pressure measurement can be taken. The pressure can be measured again to determine if it has changed now that the valve implant or repair device has been positioned in the native valve. The pressure measurement can be taken at the same point in the cardiac cycle as the baseline measurement. The pressure measurement taken by the pressure sensor at this time should be lower than the baseline pressure measurement, due to correction of the regurgitation of blood back into the atrium, which can cause a higher than normal pressure in the left atrium. Conversely, a higher pressure in the left atrium will result in a higher pressure in the fluid in the pressure sensor lumen. The pressure can be measured before the valve implant or repair device is disconnected from the pusher tube or rod, so that it can be repositioned to achieve effective placement. If a valve implant or repair device is effectively positioned, the blood will flow from the left ventricle to the aorta instead of back through the mitral valve. The pressure can be measured as many times as needed. This method can be performed on a living animal or on a simulation, such as on a cadaver, cadaver heart, simulator (e.g. with the body parts, heart, tissue, etc. being simulated), etc.

Regarding the embodiments having a pressure sensor P embedded in a wall, the left atrial pressure can be measured in the same way that the pressure is measured for the embodiments having a pressure sensor P positioned within a fluid filled lumen described herein, such as the example embodiment of FIG. 23C.

In some example embodiments of a method of measuring atrial pressure with a fluid-filled pressure sensor lumen 105 of FIG. 23D, the pressure sensor lumen can be filled with a fluid such as saline or other biocompatible fluid known by one of ordinary skill in the art to be used in fluid filled atrial pressure monitors. A baseline pressure measurement can be taken when the steerable catheter distal end 86 is in the left atrium, before the valve implant or repair device is delivered. This baseline pressure measurement can be recorded at any time by the monitoring system, such as during or at the end of systole, as explained above. The valve implant or repair device can then be delivered, but before withdrawing the delivery system, the distal end of the steerable catheter can be positioned in the left atrium, and another pressure measurement can be taken. The pressure can be measured again to determine if it has changed now that the valve implant or repair device has been positioned in the native valve. The pressure measurement can be taken at the same point in the cardiac cycle as the baseline measurement. The pressure measurement taken at this time should be lower than the baseline pressure measurement, due to correction of the regurgitation of blood back into the atrium, which can cause a higher than normal pressure in the left atrium. Conversely, a higher pressure in the left atrium will result in a higher pressure in the fluid in the pressure sensor lumen. The pressure can be measured before the valve implant or repair device is disconnected from the pusher tube or rod, so that it can be repositioned to achieve effective placement. If a valve implant or repair device is effectively positioned, the blood will flow from the left ventricle to the aorta instead of back through the mitral valve. The pressure can be measured as many times as needed. The left atrial pressure can be measured in this same way for any fluid-filled lumen embodiment without a pressure sensor P described herein. This method can be performed on a living animal or on a simulation, such as on a cadaver, cadaver heart, simulator (e.g. with the body parts, heart, tissue, etc. being simulated), etc.

In an example embodiment having a pressure sensor lumen integrated within a steerable catheter wall as illustrated in FIGS. 24A-24C, or in an example embodiment having a pressure sensor lumen integrated within the steerable catheter wall and a pressure sensor catheter within the integrated lumen as illustrated in FIGS. 25A-25C, a method of measuring pressure in the left atrium can have the same steps as that described above with respect to FIGS. 23A-23C. A method of measuring pressure using the embodiment of FIGS. 24B and 25B, with a pressure sensor that is an electronic pressure sensor, the method using the embodiment of FIG. 23B applies. The only difference is that in the embodiment of FIG. 24B, instead of having a separate pressure sensor catheter lumen 102, there is an integrated pressure sensor lumen 88 in the wall of the steerable catheter 82. FIG. 25B is similar to FIG. 24B but has a pressure sensor catheter 102 with its own lumen 105 that extends along the lumen 88 of the steerable catheter.

In an example embodiment having a pressure sensor lumen integrated in the wall of the valve implant or repair delivery catheter as illustrated in FIGS. 26A-26C, the method is similar to the example embodiments of the methods described above. In FIGS. 26A-26C, the open distal end 89 of the pressure sensor lumen of the valve delivery catheter should be positioned in the left atrium to obtain a left atrium pressure. Measuring the pressure using an electronic pressure sensor P, can use the following steps. The delivery system 80 is inserted through a trans-septal procedure, so that the delivery system 80 enters the left atrium. The method can include taking a baseline pressure measurement, in any of the ways described herein. Then the valve implant or repair device can be positioned, followed by another pressure measurement. In any of the example embodiments described herein, the pressure can be measured continuously, or it can be measured at discrete points in time. The valve implant or repair device can be repositioned, and the pressure of the left atrium can be measured as described above with respect to the embodiment of FIG. 23B. In the example embodiment of FIG. 26C, the pressure can be measured as described above with respect to the example embodiment of FIG. 23C.

The same method can be used in an example embodiment of measuring the right atrial pressure, without the step of puncturing the septum. The measurements would be taken while the distal end of the delivery system is positioned in the right side of the heart. These various methods can be performed on a living animal or on a simulation, such as on a cadaver, cadaver heart, simulator (e.g. with the body parts, heart, tissue, etc. being simulated), etc.

As described above, the delivery system for the delivery of a valve device can include at least one of the outer sheath 83, the steerable catheter 82, or the implant pusher or rod 81. The central lumen 104 of the steerable catheter 82 (FIG. 24A) and the lumen 90 of the outer sheath 83 (FIG. 36) can be filled with a biocompatible fluid such as saline. At various stages before, during, and after the delivery of a valve device, the fluid or the presence of air in the delivery system can be detected, flushed and/or removed in accordance with various embodiments described herein.

Figure 27:
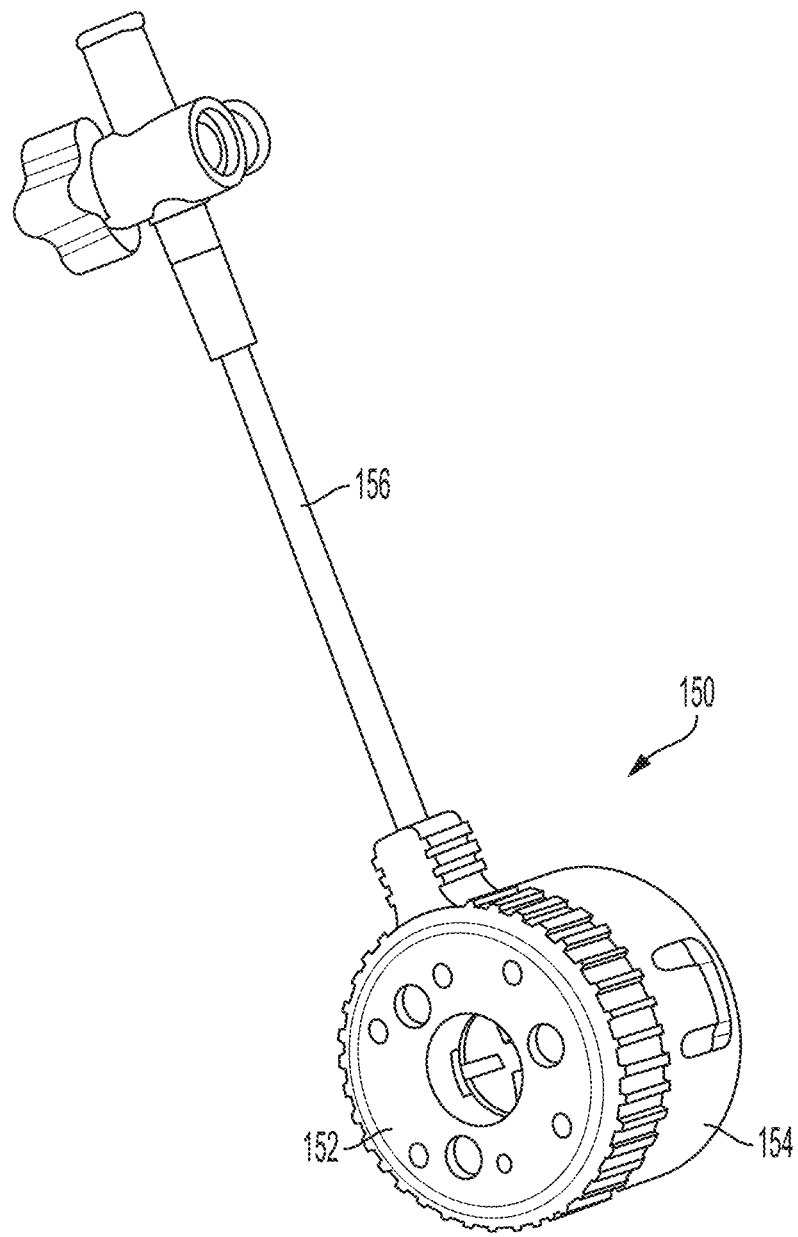
FIG. 27 is a perspective view of an example embodiment of a catheter coupler.

Referring now to FIG. 27, a schematic of an example embodiment of a rotatable flush port or catheter coupler 150 is illustrated. In various embodiments, the catheter coupler 150 can be coupled to at least one of the implant pusher or implant catheter 81, the steerable catheter 82, or the outer sheath 83. Each catheter coupler can be connected to a control handle (not shown) that controls operation/positioning of an attached implant catheter 81, steerable catheter 82, and outer sheath 83. The catheter coupler 150 can be used to sense or monitor fluid pressure in the catheter and/or can be used to flush the catheter, such that no air is present in the catheter.

The catheter coupler 150 coupler can take a wide variety of different forms. Also, while the term catheter coupler is generally used herein, this can also be called a flush port and can be positioned at various locations along a catheter and/or catheter handle. In the embodiments disclosed below, the catheter couplers are configured to allow flushing of the catheter, without rotating the catheter. This can be accomplished in a variety of different ways. The embodiments described below are two of the ways that catheter couplers can be configured to allow flushing of the catheter, without rotating the catheter.

Figure 28:
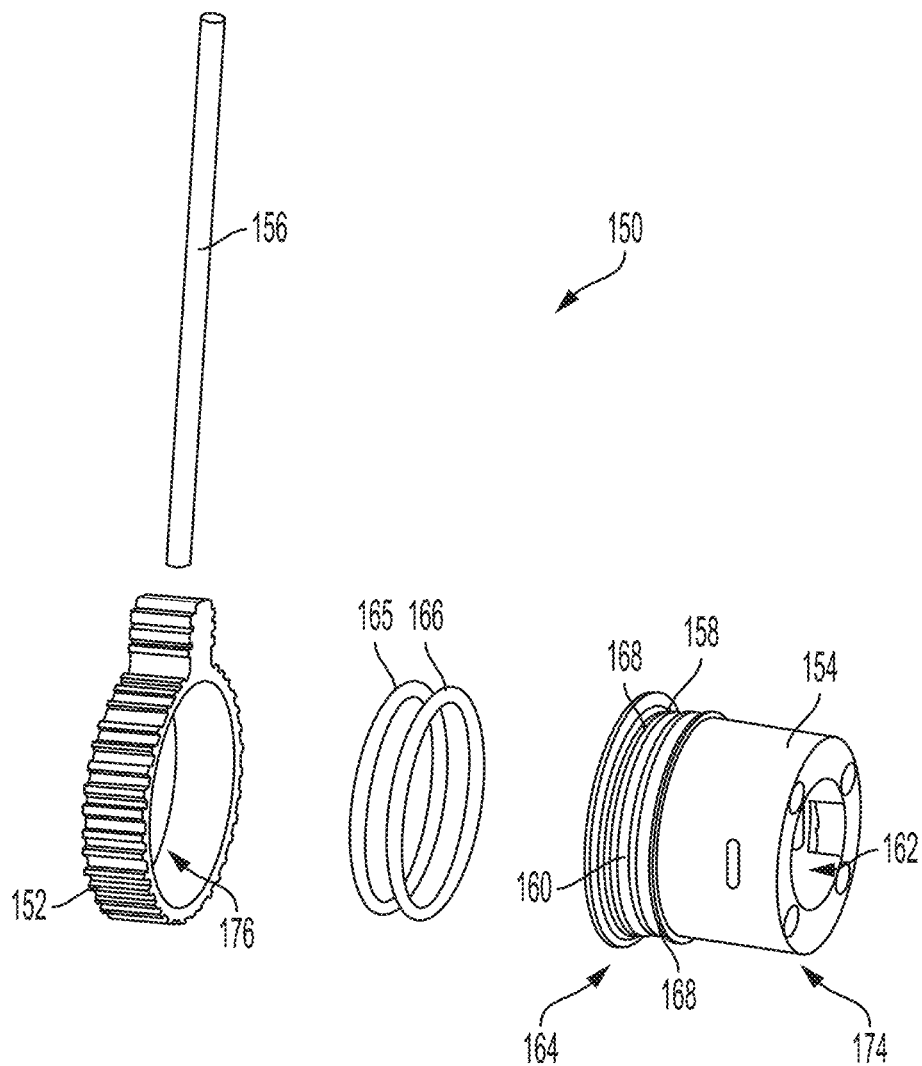
FIG. 28 is an exploded view of various components of the catheter coupler of FIG. 27.

With reference to FIGS. 27-28 an example embodiment of a catheter coupler 150. The illustrated coupler includes a cap 152 that is rotatably mounted to a housing 154. The cap 152 can be coupled to a tube 156. The tube 156 can be used for a variety of different purposes. For example, the tube 156 can be used to flush the catheter, measure pressure in the catheter, sample fluids from the catheter, deliver fluid through the catheter, etc.

Figure 29:
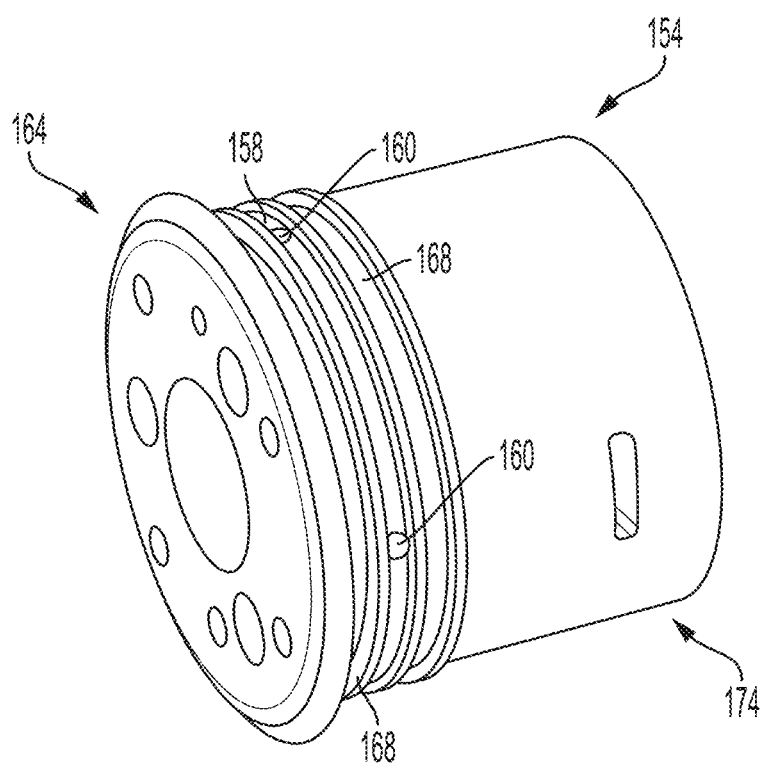
FIG. 29 is a perspective view of a catheter coupler housing of the catheter coupler of FIG. 27.

With reference to FIG. 28-29, the housing 154 can include a fluid channel 158 disposed circumferentially around the housing 154. The channel 158 is illustrated in the housing but can be defined or partially defined in the cap 152. The channel 158 is connected to at least one port 160. The port 160 connects the channel 158 to a lumen or central passage 162 of the housing 154. The lumen or central passage 162 extends between the first end 164 and the second end 174 of the housing of the housing 154.

The cap 152 is rotatably attached to the housing 154 at the first end 164 of the housing 154. The cap 152 is ring shaped with a central opening 176. A lumen or passage 177 extends from the central opening 176 of the cap 152 to the tube 156. As a result, fluid inside the central opening 176 can flow through the cap to the tube 156.

The cap 152 can fit over top the first end 164 of the housing 154 such that a seal is formed between the cap 152 and the housing 154 on both sides of the channel 158. The seals between the cap 152 and the housing 154 can be formed in a variety of ways. For example, with reference to FIG. 28, the catheter coupler 150 can include one or more sealing members. For example, catheter coupler 150 can include a first sealing member 165 and a second sealing member 166. The sealing members can be ring-shaped and fit between the housing 154 and the cap 152. The first sealing member 165 and a second sealing member 166 fit in grooves 168, which are set in the housing 154. The seals 165, 166 prevent any fluid in the channel 158 from escaping through the rotatable coupling between the cap 152 and the housing 154. As a result, fluid in the passage 162 can flow through the port 160, into the channel 158, through the passage 177, and through the tube 156 (or vice versa), without leakage between the cap 152 and the housing 154.

The cap 152 can rotate with respect to the housing 154. For example, in various embodiments, the cap 152 can rotate 160 degrees about the housing 154 and can rotate clockwise and/or counter clockwise with respect to the housing 154. The sealing members 165, 166 are configured to maintain seals between the housing 154 and the cap 152 while the cap rotates relative to the housing.

Figure 30:
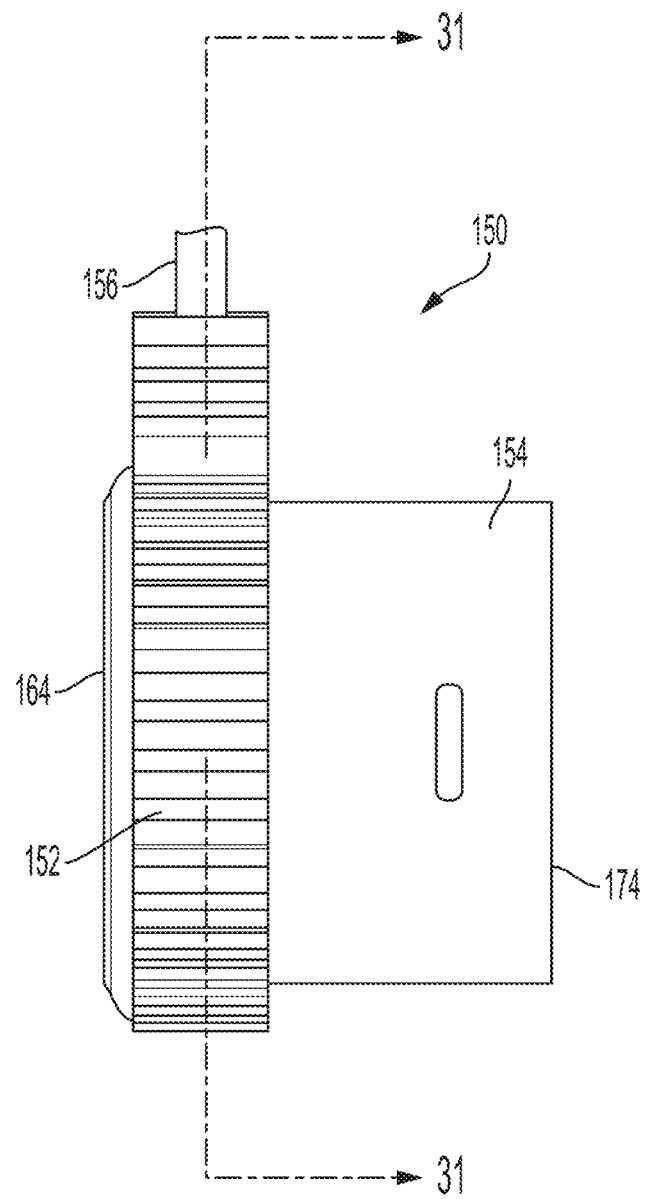
FIG. 30 is a side view of the catheter coupler of FIG. 27.
Figure 31A:
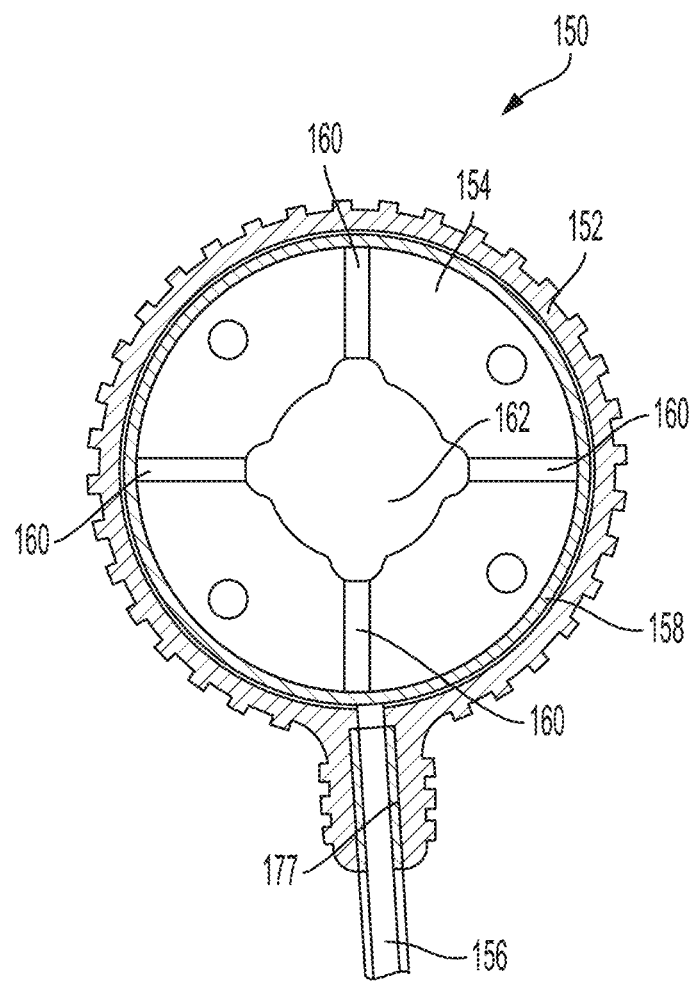
FIG. 31A-C are cross-sectional views taken along the plane indicated by lines 31-31 in FIG. 30 of the catheter coupler rotated to various positions.
Figure 31B:
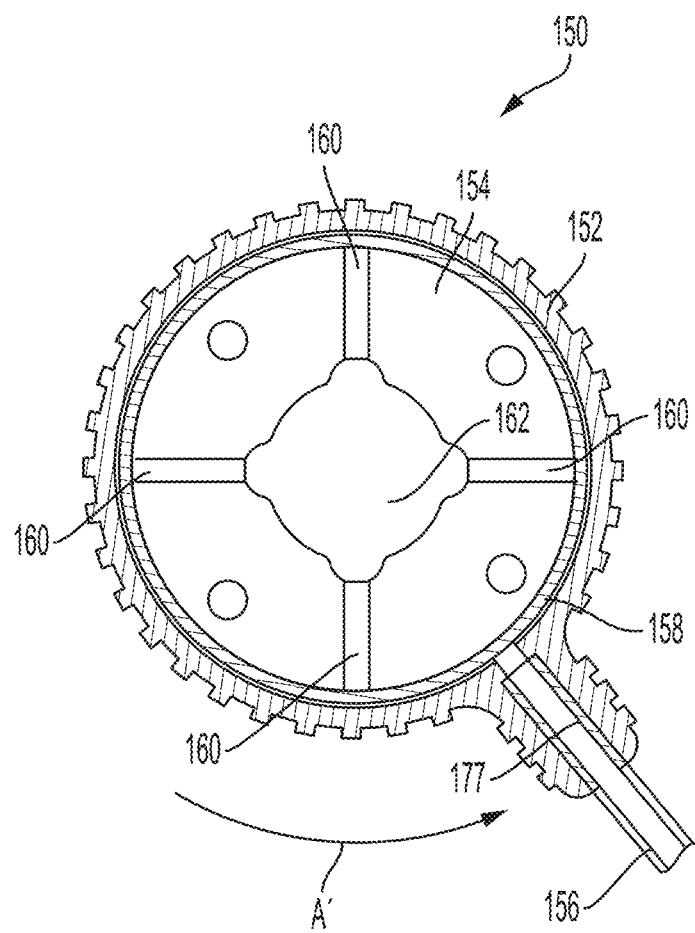
Figure 31C:
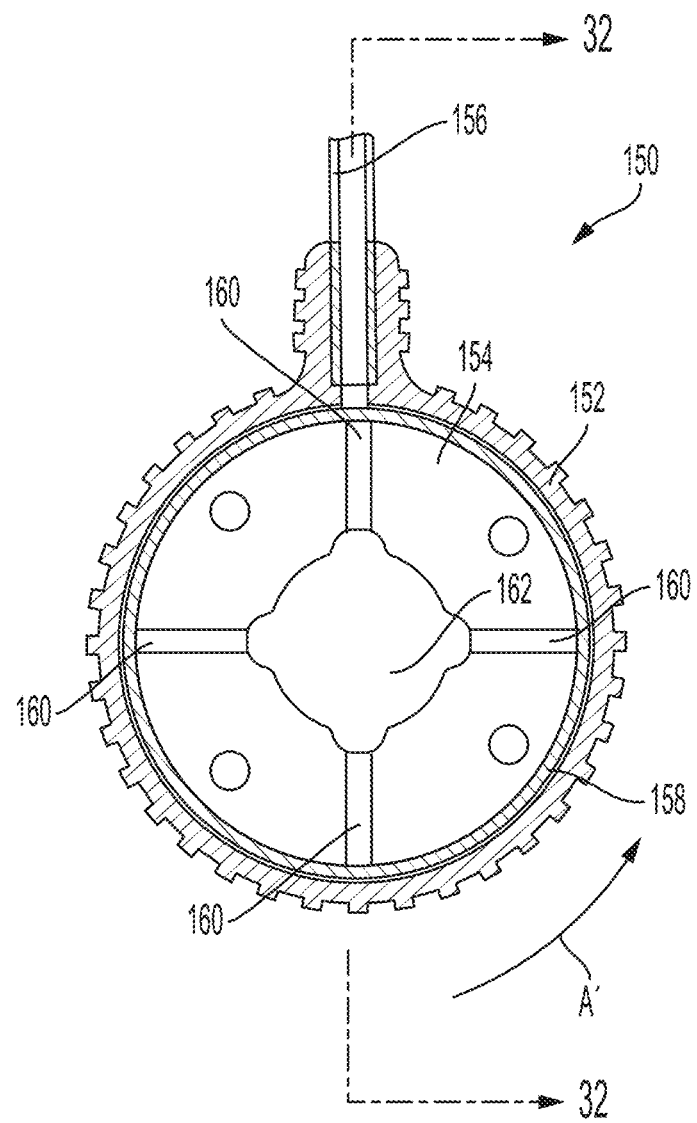

FIGS. 31A-C illustrate a cross section of a portion of the catheter coupler 150, taken along the plane indicated by lines 31-31 in FIG. 30. In the illustrated example, the housing 154 includes four passages 160 that connect the lumen or passage 162 to the circumferential channel 158. The housing 154 can have any number of passages 160 connecting the lumen or passage 162 to the channel or groove 158. For example, the housing 154 can have any number of passages between three and twenty. The tube 156 is in fluid communication with the channel 158, the passages 160, and the lumen or passage 162.

With reference to FIGS. 31B-C, with cap 152 is rotatable circumferentially around housing 154 in the A' direction. This allows the tube 156 to be rotated to the "top-dead-center" or vertically upright position illustrated by FIG. 31C. In this position, applying a vacuum to the tube 156 can remove all air from the tube 156, coupler 150, and attached catheter, leaving only fluid, such as saline solution and blood. The process of filling the open space in the lumens of the catheters with liquid and removing the air is referred to as flushing. Injecting liquid (e.g., a saline solution, etc.) through the port should fill the lumens with liquid. If any air remains, the air can be removed before the liquid when the tube 156 is in the upright position, because air is lighter than the liquids and moves in an upward direction.

Figure 32:
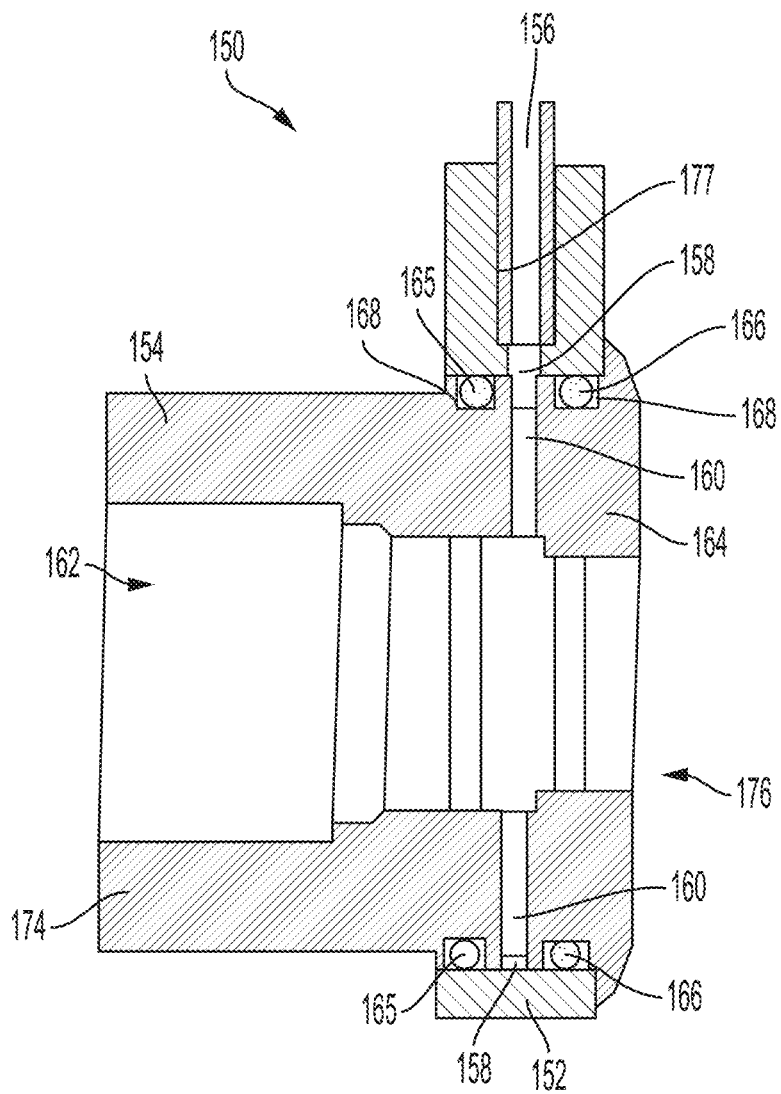
FIG. 32 is a cross-sectional view taken along the plane indicated by lines 32-32 in FIG. 31C.
Figure 33:
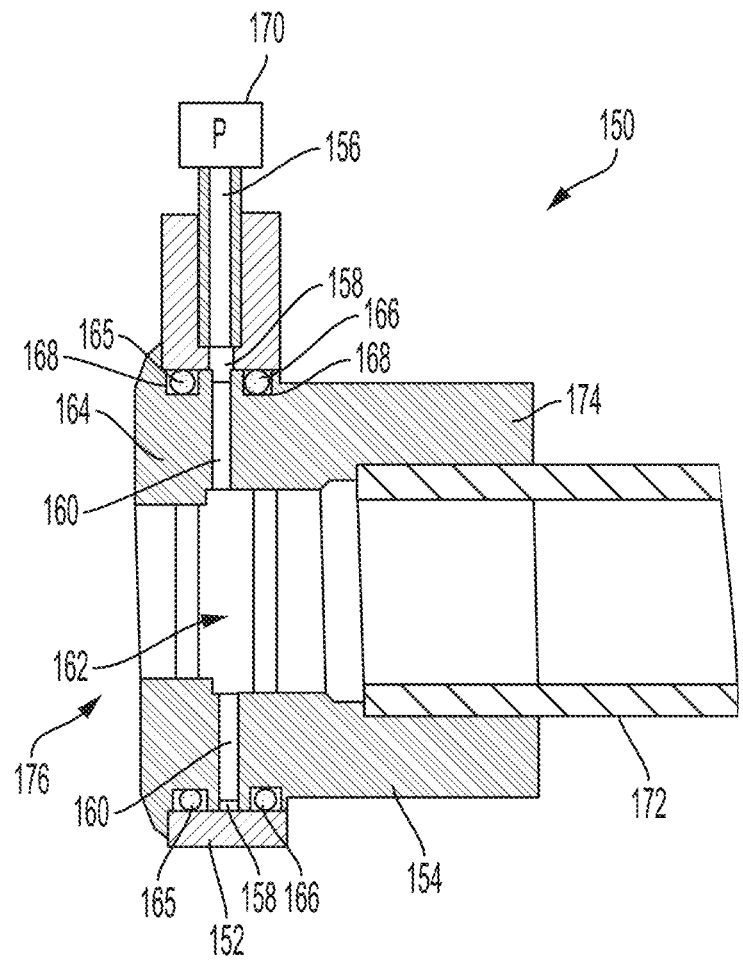
FIG. 33 illustrates a cross-sectional view of the catheter coupler shown in FIG. 32 coupled to a catheter and a pressure sensor.

With reference to FIG. 32-33, a cross sections of the catheter coupler 150 and a cross-section of a coupler 150 with a catheter 172 are illustrated. As described above, the first sealing member 165 and the second sealing member 166 are positioned circumferentially around the housing 154, between the housing 154 and the cap 152. The first sealing member 165 and the second sealing member 166 can be set at least partially within the grooves 168 of housing 154. Fluid can flow from the lumen or passage 162, through the passages 160, into the channel 158, through the passage 177, and through the tube 156.

With reference to FIG. 33, the catheter coupler 150 can be connected to a pressure sensor 170 via the tube 156. The housing 154 can be coupled to a catheter 172 at the second end 174 of housing 154. The catheter 172 can include at be the pusher tube or rod 81, the steerable catheter 82, or the outer catheter or sleeve 83. Different catheter couplers 150 can have different sized lumens or passages 162 to mate with the differently sized pusher tube or rod 81, steerable catheter 82, and/or the outer catheter or sleeve 83. The pressure sensor 170 can be used to measure pressure in the heart as described above, except the pressure is monitored through the main or primary lumen of the pusher tube or rod 81, steerable catheter 82, and/or the outer catheter or sleeve 83.

Figure 34:
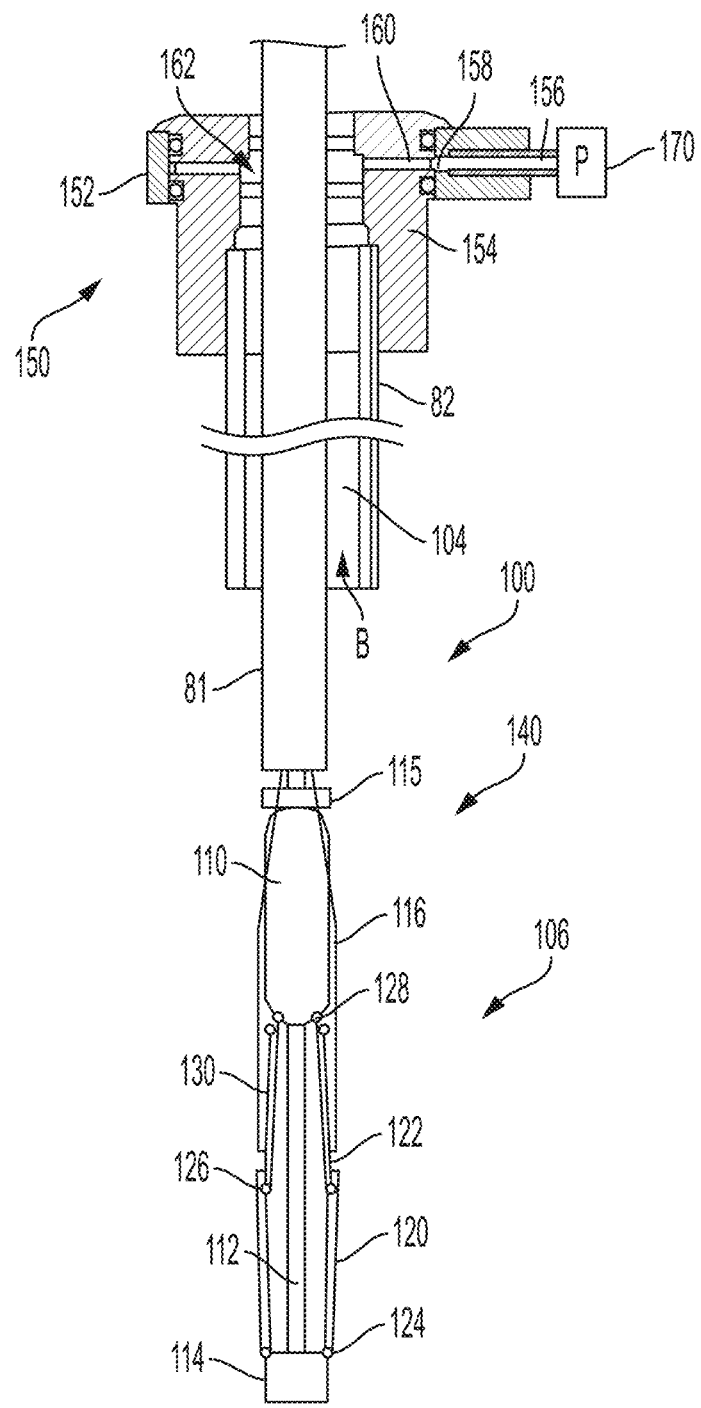
FIG. 34 illustrates a partial cross-sectional view of the catheter coupler attached to a guide sheath of a system for implanting an implantable prosthetic device.

With reference to FIG. 34, the catheter coupler 150 is illustrated on the proximal end of steerable catheter 82. Fluid, which can be the blood in the left atrium of the heart, can travel through the central lumen 104 of the steerable catheter 82, through flow-path B, and into the lumen 162 of the catheter coupler 150. This flow path B is the volume between the pusher or implant catheter 81 and the steerable catheter 82. In this example, the fluid that travels into the central lumen 104 of the steerable catheter 82 is in fluid communication with the lumen 162, the ports 160, the channel 158, the tube 156 and the pressure sensor 170.

The pressure sensor 170 can be a fluid-filled pressure sensor, and the pressure sensor lumen can be filled with a fluid such as saline or other biocompatible fluid known by one of ordinary skill in the art to be used in fluid filled atrial pressure monitors. The pressure sensor P can be at a more proximal location along the length of the catheter delivery system. A baseline pressure measurement can be taken when the steerable catheter 82 is in the left atrium, before the valve implant or repair device is delivered. This baseline pressure measurement can be recorded at any time, such as during or at the end of systole, as explained above. The valve implant or repair device can then be delivered, but before withdrawing the delivery system, the distal end of the steerable catheter 82 can be positioned in the left atrium, and another pressure measurement can be taken. The pressure can be measured again to determine if it has changed now that the valve implant or repair device has been positioned in the native valve. The pressure measurement can be taken at the same point in the cardiac cycle as the baseline measurement. The pressure measurement taken by the pressure sensor at this time should be lower than the baseline pressure measurement, due to correction of the regurgitation of blood back into the atrium, which can cause a higher than normal pressure in the left atrium. Conversely, a higher pressure in the left atrium will result in a higher pressure in the fluid in the pressure sensor lumen. The pressure can be measured before the valve implant or repair device is disconnected from the pusher tube or rod, so that it can be repositioned to achieve effective placement. If a valve implant or repair device is effectively positioned, the blood will flow from the left ventricle to the aorta instead of back through the mitral valve. The pressure can be measured as many times as needed.

With reference to FIG. 34, the catheter coupler 150 can be used to flush fluids through at least one of the implant pusher or rod 81, the steerable catheter 82, or the outer sheath 83 to ensure that there is no air in the delivery system. As described above, the catheter coupler 150 can be filled with saline or other biocompatible fluid when the catheter coupler 150 is placed in the heart. A user may "pull back" the fluid through the coupler catheter 150 proximally to ensure that the system is in proper working condition and that there are no pockets of air or other fluids in the system. Pulling back the fluid can pull blood through flow-path B and towards the proximal end of catheter coupler 150. Blood and/or flush fluid, such as saline can fill the lumen 162, the ports 160, the channel 158, and the tube 156 when a vacuum is applied to the tube. The fluid and/or blood can be collected through the tube 156 or fluid or medication can be introduced through the tube. Flushing of the catheter 82 can be performed through the tube 156 to remove any air in the catheter 82, coupler 150, and/or the tube 156. A pocket or pockets of air may be present in the lumen 162, the ports 160, the channel 158, and/or the tube 156. When the fluid is "pulled back" or drawn out with a vacuum, the air may travel through flow-path B and towards the proximal end of catheter coupler 150. The air may travel into a port 160 and into the channel 158. With reference to FIGS. 34 and 31 A-C, the cap 152 of the catheter coupler 150 can be rotated with respect to the housing 154, e.g. in the A' direction (i.e. vertically in FIG. 31B) to facilitate the pocket of air traveling through the port 160 through the channel 158 and into tube 156. The pocket of air or fluid may travel through tube 156 and evacuated from the system.

Referring to FIG. 34, the implant pusher or catheter 81 of the delivery system and the valve repair device can be extended through the lumen or passage 162 of the housing 152. Although not shown, the implant pusher or catheter 81 can be connected to a catheter coupler 150 at the proximal end of the implant pusher or catheter 81.

In various embodiments, multiple catheter couplers or rotatable fluid ports can simultaneously be coupled to the various components of the delivery system for the delivery of a valve device. The catheter couplers can flush various components of the delivery system for the delivery of a valve repair device or a valve replacement device. As described above, the distal ends of the steerable catheter, outer catheter, and pusher tube or rod can terminate in different respective areas of the heart.

Figure 35:
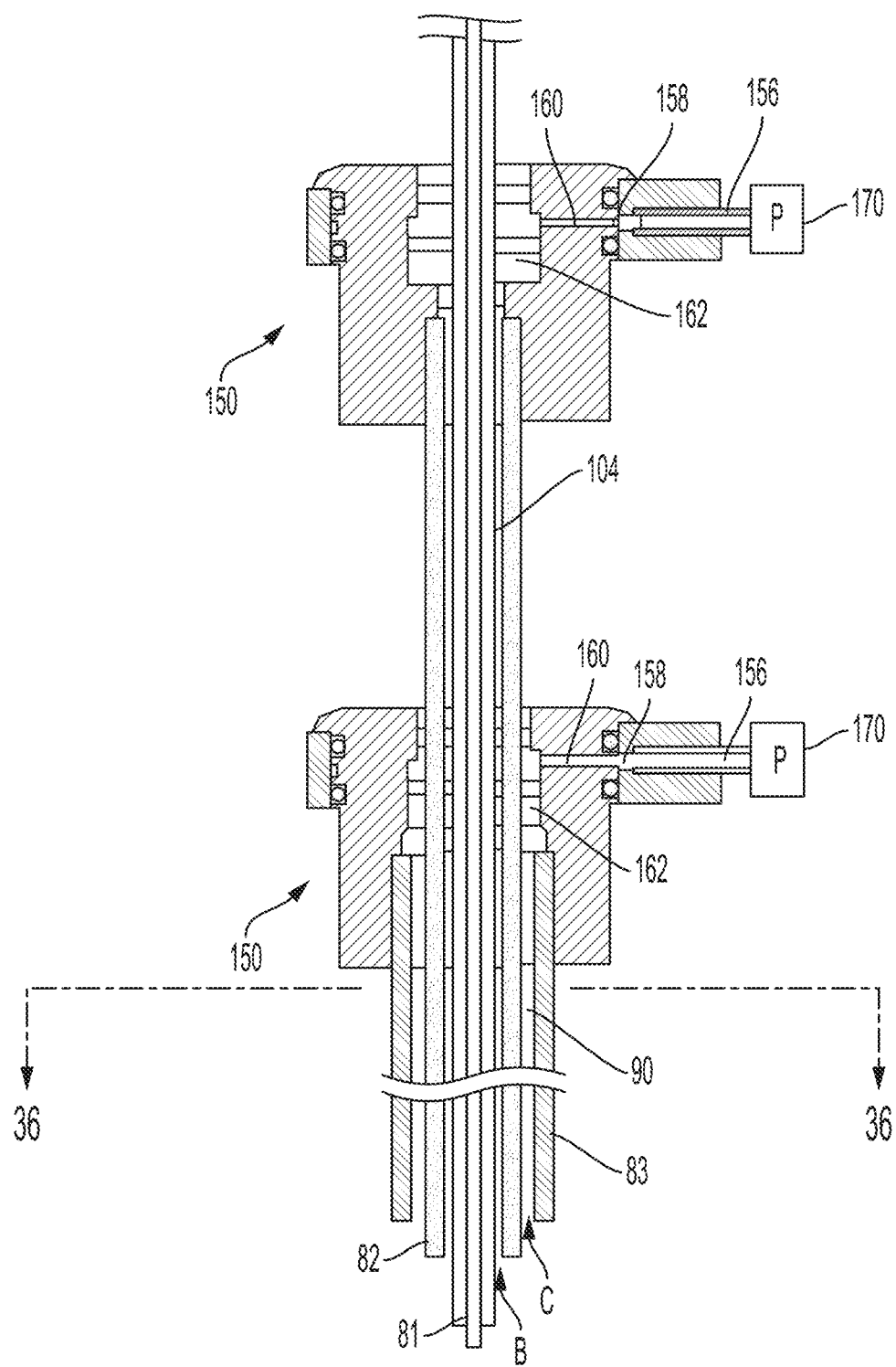
FIG. 35 illustrates a cross-sectional view of example catheter couplers attached to a guide sheath and a steerable catheter of an implantable prosthetic device.

With reference to FIG. 35, for example, the proximal end of a steerable catheter 82 and the proximal end of the outer catheter or guide sheath 83 are each attached to a catheter coupler 150. The steerable catheter 82 is disposed at least partially within the passage 162 of the housing 152. The implant pusher or catheter 81 is disposed at least partially within the lumen or passage 162 of the housing 152. The implant pusher or catheter 81 extends through the outer catheter or guide sheath 83, as well as the coupler that is connected to the outer lumen or guide sheath.

Liquid, which can be the blood and/or flush liquid, can travel through the main or central lumen 104 of the steerable catheter 82, through flow-path B and into the catheter coupler 150. This flow path B is the volume between the pusher or implant catheter 81 and the steerable catheter 82. In this example, the liquid that travels into the central lumen 104 of the steerable catheter 82 is in fluid communication with the lumen 162, the ports 160, the channel 158, the tube 156, and the pressure sensor 170.

Liquid, which can be the blood in the left atrium of the heart and/or flush liquid, can travel through the lumen 90 of the outer catheter 83, through flow-path C, and into the lumen or passage 162 of the catheter coupler 150. This flow path C is the volume between the steerable catheter 82 and the guide sheath 83. In this example, the liquid that travels into the lumen 90 of the outer catheter 83 is in fluid communication with the lumen or passage 162, the ports 160, the channel 158, and the pressure sensor 170. A catheter coupler 150 can also be provided on the proximal end of the pusher tube 81. As such, a coupler can be provided on one or more of any of the pusher tube 81, the steerable catheter 82, and the guide sheath 83.

The catheter coupler 150 connected to the outer guide sheath 83 can be used to flush liquids through the outer guide sheath 83 to ensure that there is no air in the guide sheath portion of the delivery system. When the liquid is "pulled back" or drawn out with a vacuum, the air may travel through flow-path C and towards the proximal end of catheter coupler 150. The air may travel into a port 160 and into the channel 158. With reference to FIGS. 35 and 31 A-C, the cap 152 of the catheter coupler 150 can be rotated with respect to the housing 154, e.g. in the A' direction (i.e. vertically in FIG. 31B) to facilitate the pocket of air traveling through the port 160 through the channel 158 and into tube 156. The pocket of air can travel through tube 156 and evacuated from the system. Blood can fill the lumen or passage 162, the ports 160, the channel 158, and/or tube 156 when drawn by the user. The flush fluid and blood may travel through tube 156 to a collection tube, medication can be introduced through the tube, and/or pressure inside the heart can be measured through the tube.

In various embodiments, air that is present in the outer sheath 83 can be detected and/or removed by the catheter coupler 150. Air can travel through flow-path C and towards the proximal end of the attached catheter coupler 150. The air may travel into a port 160 and towards the channel 158. With reference to FIGS. 35 and 31 A-C, the cap 152 of the catheter coupler 150 connected to the outer sheath 83 can be rotated with respect to the housing 154, e.g. in the A' direction (FIG. 31B) to facilitate the pocket of air raveling through the port 160 through the channel 158 and tube 156. The pocket of air can be evacuated through the tube 156.

Figure 36:
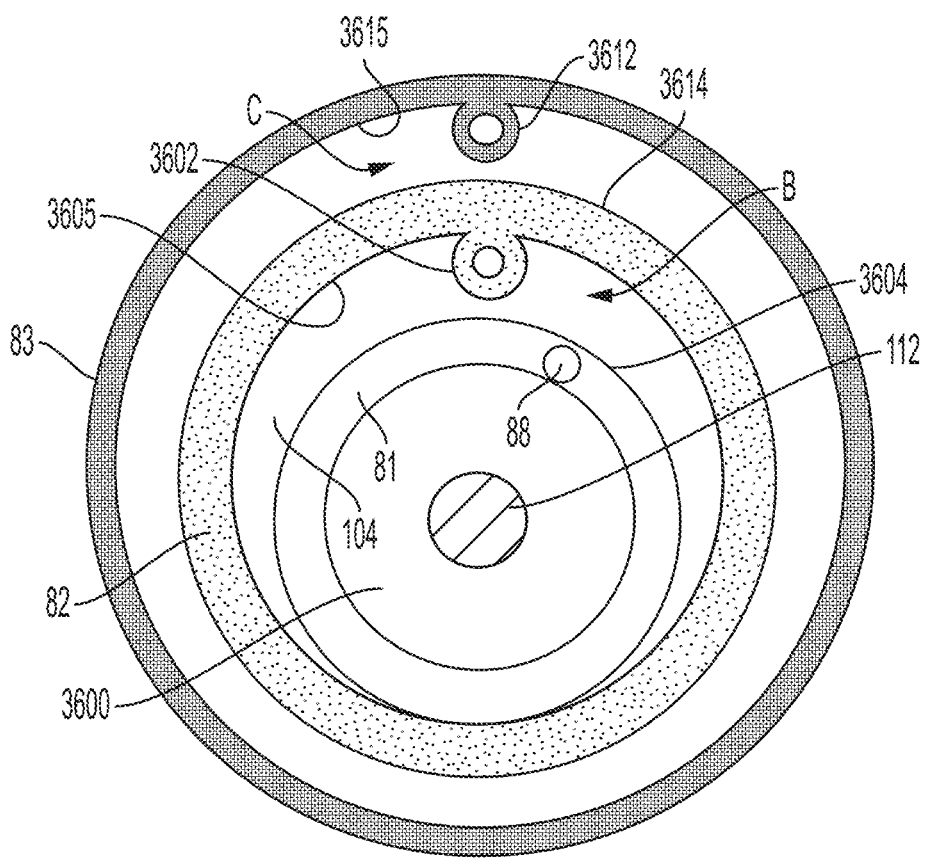
FIG. 36 is a schematic cross-sectional view of example catheters of a delivery system for an implantable prosthetic device.

FIG. 36 is a cross sectional view of the pusher rod or tube 81, the steerable catheter 82, and the outer sheath 83 taken along the plane indicated by lines 36-36 in FIG. 35. The space 3600 between the actuation rod 112 and the pusher tube 81, the space or flow path B between the pusher tube 81 and the steerable catheter 82, and/or the space or flow path C between the steerable catheter 82 and the outer sheath 83 can be filled with a flush fluid before being introduced into a patient's vasculature. These spaces can be flushed as described herein to remove any air from these spaces.

In the example illustrated by FIG. 36, the steerable catheter 82 includes a radially inwardly extending projection 3602 for a pull wire that is used to steer the steerable catheter 82. The radially inwardly extending projection 3602 maintains the space or path B between the outside surface 3604 of the pusher catheter 81 and the inside surface 3605 of the steerable catheter 82. This space or path B is maintained when the catheters are flexed and steered through the patient's vasculature to the implant location, such as the mitral valve. As a result of the clear path B, the pressure in the heart can be accurately measured at a coupler 150 that is connected to the steerable catheter 82.

Still referring to FIG. 36, the guide or outer sheath 83 includes a radially inwardly extending projection 3612 for a pull wire that is used to steer the guide or outer sheath 83. The radially inwardly extending projection 3612 maintains the space or path C between the outside surface 3614 of the steerable catheter 82 and the inside surface 3615 of the guide sheath 83. This space or path C is maintained when the catheters are flexed and steered through the patient's vasculature to the implant location, such as the mitral valve. As a result of the clear path C, the pressure in the heart can be accurately measured at a coupler 150 that is connected to the guide sheath 83.

With reference to FIGS. 37-39D, an example embodiment of a flush port or catheter coupler 450 that includes a housing 454 and an outlet extension 452 that is fixed relative to the housing. The housing 454 and the outlet extension 452 can be fixed relative to one another in a variety of different ways. For example, the flush port or coupler can be integrally formed as illustrated, such as by casting, molding, 3-D printing, etc., or from multiple pieces that are secured together. In the example embodiment illustrated by FIGS. 37-39D, the tube 156 is not rotatable relative to the housing 454, like the embodiment illustrated by 27-35.

Figure 37:
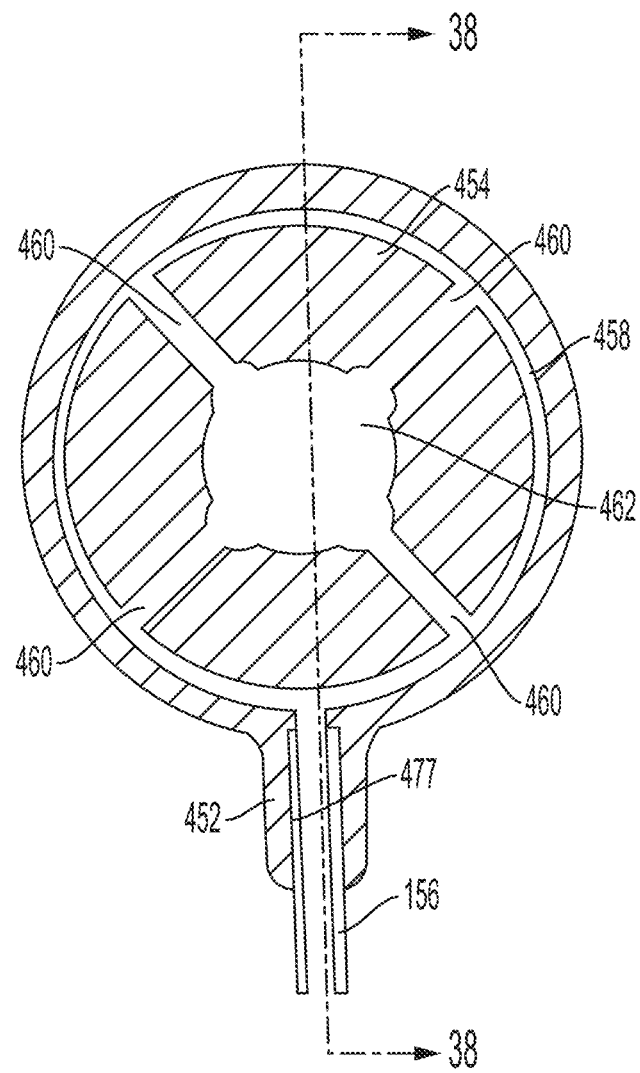
FIG. 37 illustrates a cross-sectional view of an example embodiment of a catheter coupler.
Figure 38:
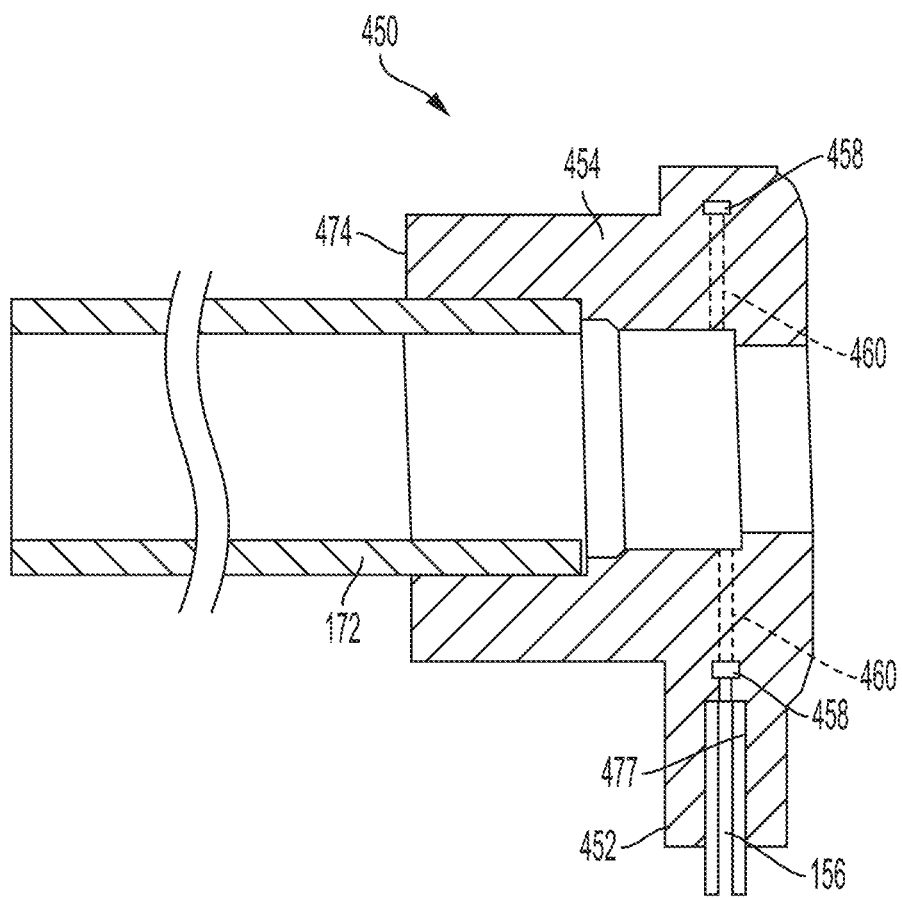
FIG. 38 is a cross-sectional view taken along the plane indicated by lines 38-38 in FIG. 37.

With reference to FIGS. 37 and 38, the catheter coupler 450 couples a catheter 172, such as the guide sheath 83, the steerable catheter 82, or the pusher tube 81 to a port tube 156. The coupler includes a lumen or passage 462 that is configured to connect to the catheter 172. The lumen or passage 462 is configured for connection to the guide sheath 83, the steerable catheter 82 or the pusher catheter 81 in the same manner as the lumen or passage 162. A channel 458 is disposed circumferentially within the catheter coupler 450. The channel 458 is connected to the lumen or passage 462 via a plurality of ports 460. The channel 458 is connected to the tube 156 via an outlet port 477.

Figure 39A:
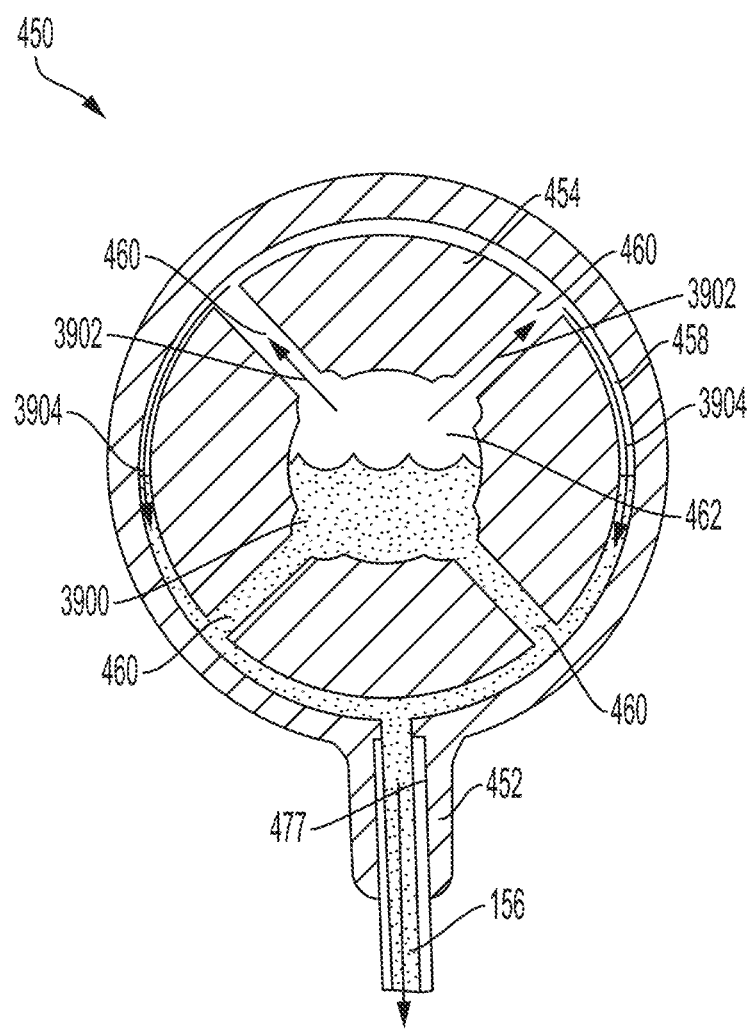
FIG. 39A-D illustrate operation of the catheter coupler of FIG. 38.
Figure 39B:
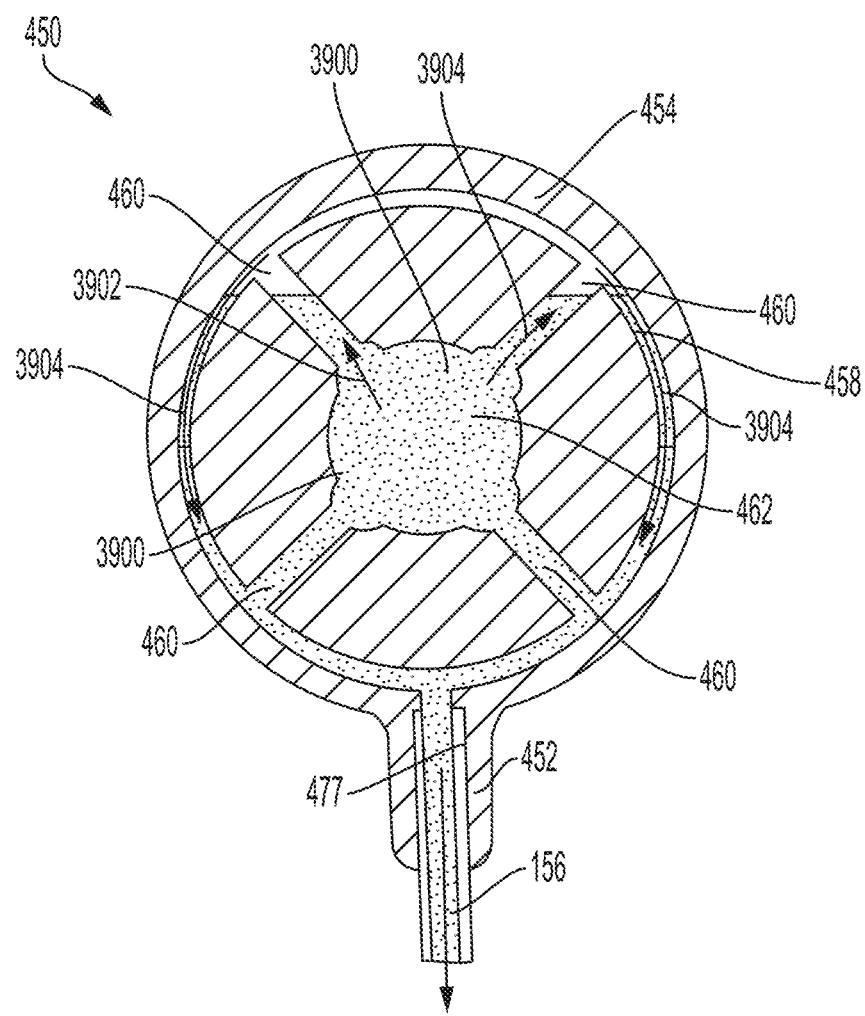
Figure 39C:
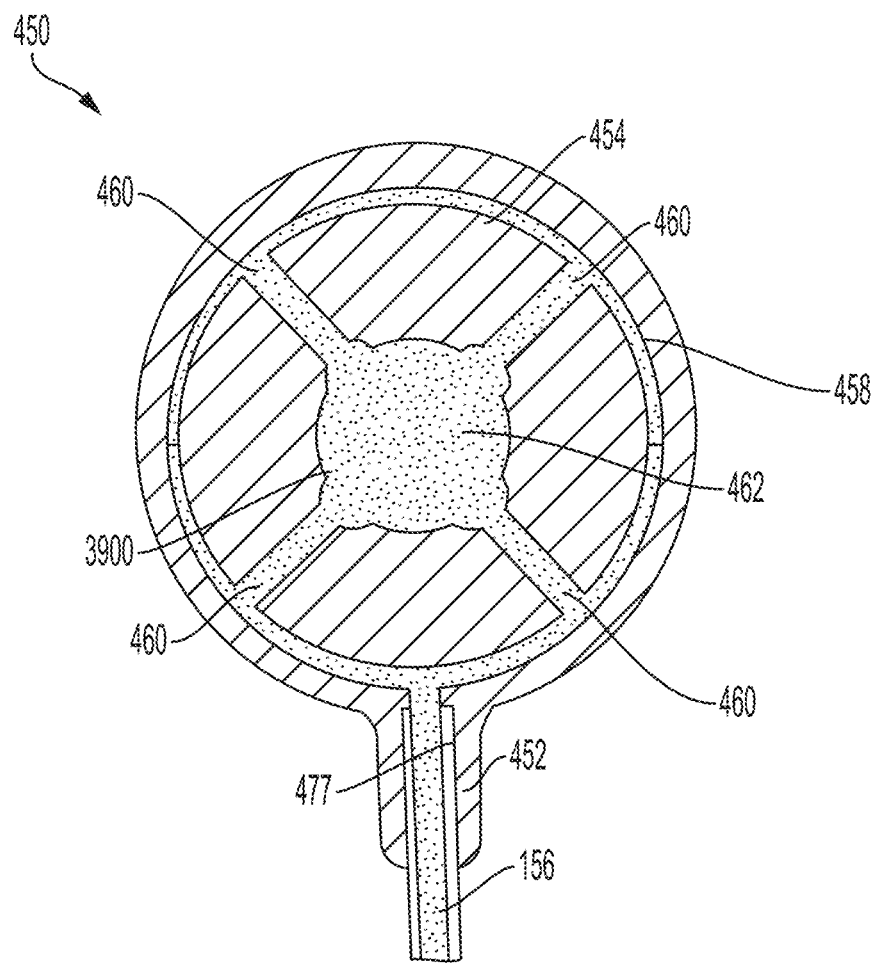

With reference to FIGS. 39A-C, the catheter coupler or flush port 450 can be used to flush air out of the connected catheter, such as the implant pusher or catheter 81, the steerable catheter 82, or the outer sheath 83, without needing to rotate the tube 156 to the upright or vertical position (See FIG. 31C). The catheter coupler 450 and attached catheter can be filled with saline or other biocompatible liquid when the catheter coupler 450 is to be used.

The viscosity of air is less than the viscosity of a liquid, such as water (i.e. saline) and/or blood. Therefore, the air has lower resistance to fluid flow. The passages with the lowest fluid flow resistance (i.e. the upper ones of the passages 460 and the upper portion of the circumferential passage 458 containing air) will see the largest total volume (air+liquid) flow through them when a vacuum is applied to the tube 156. If the potential created by the vacuum applied to the tube 156 (the "net positive suction head applied" or "NPSHA") is greater than the height potential between the top and bottom ports 460 (the "net positive suction head required" or "NPSHR"), the fluid can flow first and most rapidly through the air exposed ports, resulting in evacuation of the air from the seal housing regardless of the flush tube orientation as illustrated by FIGS. 39A-39C.

Referring to FIG. 39A, a user can draw a vacuum through the tube 156, which pulls fluid 3900 in the catheter 172 into the passage 462. The liquid 3900, such as flush fluid and/or blood in the passage 462 displaces air in the passage 462 through the upper ports or passages 460 as illustrated by arrows 3902. The circumferential passage 458 and/or the ports or passages 460 can be sized such that air or a mixture of air and liquid 3900 in the upper ones of the passages 460 and the circumferential passage 458 flows to the outlet port 477 before or faster than the liquid in the lower ports flows to the outlet port 477. This preferential flow is regardless of the orientation/direction of the coupler 450 and fixed outlet port. That is, the circumferential passage 458 and/or the ports or passages 460 are small enough or constrictive enough to allow air or a mixture of air and liquid 3900 in the upper passages and the circumferential passage 458 to flow to the outlet port 477 before or faster than the liquid in the lower ports flows to the outlet port 477, regardless of the orientation of the coupler 450 and fixed outlet port. The circumferential passage 458 and/or the ports or passages 460 can be sized for this preferential flow of air or air mixed with the liquid over liquid alone, because air or air mixed with liquid is less viscous than the liquid alone. In one example embodiment, a cross-section of the circumferential passage 458 is substantially rectangular with a cross-sectional width (i.e. left to right in FIG. 38) between 0.015 and 0.125 inches, such as between 0.030 and 0.110 inches, such as between 0.050 and 0.100 inches, such as between 0.060 and 0.080 inches, such as about 0.070 inches, such as 0.070 inches, and a height (i.e. bottom to top in FIG. 38) between 0.010 and 0.100 inches, such as between 0.020 and 0.80 inches, such as between 0.025 and 0.050 inches, such as between 0.030 and 0.040 inches, such as about 0.035 inches, such as 0.035 inches, and the ports or passages are substantially circular with a cross-sectional diameter between 0.015 and 0.125 inches, such as between 0.030 and 0.110 inches, such as between 0.050 and 0.100 inches, such as between 0.060 and 0.080 inches, such as about 0.070 inches, such as 0.070 inches to facilitate the preferential flow of air and air mixed with the liquid over the liquid alone.

Referring to FIGS. 39A and 39B, when the circumferential passage 458 and/or the ports or passages 460 are appropriately sized, the air, can more readily travel from the lumen or passage 462, out the upper passages as indicated by the arrows 3902, along the circumferential passage 458 as indicated by arrow 3904, and out through the outlet 452 and tube 156. Referring to FIG. 39B, the liquid 3900 begins to fill the upper ones of the lumens or passages 460, forcing the air into the circumferential passage 458. The air and air mixed with liquid continues to move along the circumferential passage 458 as indicated by arrow 3904, and out through the outlet 452 and tube 156. In FIG. 39C, all of the passages of the coupler have been filled with liquid and all of the air has been forced out the tube 156.

If the circumferential passage 458 and/or the ports or passages 460 were two large, there would be less restriction on the liquid flowing through the lower portion of the circumferential passage 458 and/or lower ones of the ports or passages 460. As a result, the preferential flow of the air or the air and liquid mixture over the liquid alone would not occur. In some example embodiments, a larger vacuum can be applied to the tube if the vacuum applied for given sizes of the circumferential passage 458 and the ports or passages 460 does not result in the preferential flow of the air out of the catheter. However, large sizes of the circumferential passage 458 and/or the ports or passages can prevent any reasonable vacuum force from preferentially withdrawing the air out of the catheter.

Still referring to FIGS. 39A-39D, the tube 156 can be used for a variety of different purposes. For example, the tube can be used to flush the catheter, measure pressure in the catheter, sample fluids from the catheter, deliver fluid through the catheter, etc.

Figure 39D:
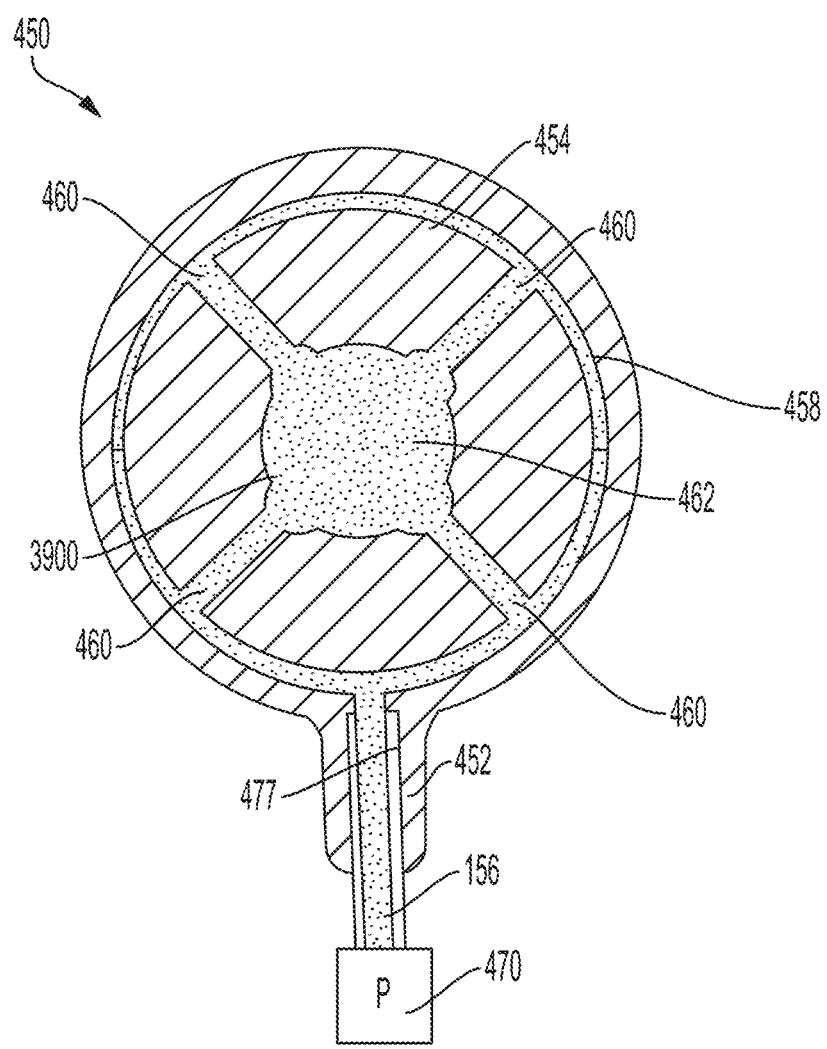

Referring to FIG. 39D, the example coupler 450 can be used to measure pressure in a connected catheter, such as the guide sheath 83, the steerable catheter 82, or the implant catheter, without requiring rotation of the tube 156. Any combination of the example embodiments described above, can be used in a method for measuring pressure in the heart, such as atrial pressure, without requiring the entry of a new catheter for the purpose of measuring the atrial pressure. For example, the coupler 450 illustrated by FIGS. 37-39D can be used to measure pressure in the same manners as described with respect to the coupler 150 shown in FIGS. 27-36.

The method of measuring pressure can begin with the entry of the delivery system delivering a valve implant or repair device. To obtain a left atrial pressure when using a trans-septal technique, an outer catheter having inner catheters as described above, can be inserted into the right femoral vein. From there the catheter is advanced up the inferior vena cava and into the right atrium. Once the distal end of the delivery system is in the right atrium, the septum is punctured and then the catheter passes into the left atrium. Once in the left atrium, any of the pressure sensing arrangements disclosed herein can be used to monitor atrial pressure. This method can be performed on a living animal or on a simulation, such as on a cadaver, cadaver heart, simulator (e.g. with the body parts, heart, tissue, etc. being simulated), etc.

While various inventive aspects, concepts and features of the disclosures may be described and illustrated herein as embodied in combination in the example embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. Further, the treatment techniques, methods, operations, steps, etc. described or suggested herein can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

What is claimed is:

1. A delivery system comprising:
   a first catheter coupler comprising:
      a first catheter connection lumen;
      an outer circumferential passage;
      a plurality of connecting passages that each connect the catheter connection lumen to the outer circumferential passage;
      an outlet port in fluid communication with the outer circumferential passage; and
      wherein the outer circumferential passage and the plurality of connecting passages are sized such that when:
         the outlet port is oriented in a direction not vertically upward;
         upper ones of the connecting passages contain air;
         lower ones of the connecting passages contain liquid; and
         a vacuum is applied to the tube;
      the air is drawn out of the outlet port;
   a second catheter coupler comprising:
      a second catheter connection lumen;
      an outer circumferential passage;
      a plurality of connecting passages that each connect the catheter connection lumen to the outer circumferential passage;
      an outlet port in fluid communication with the outer circumferential passage; and
      wherein the outer circumferential passage and the plurality of connecting passages are sized such that when:
         the outlet port is oriented in a direction not vertically upward;
         upper ones of the connecting passages contain air;
         lower ones of the connecting passages contain liquid; and
         a vacuum is applied to the tube;
      the air is drawn out of the outlet port,
   a first catheter connected to the first catheter connection lumen of the first catheter coupler;
   a second catheter connected to the second catheter connection lumen of the second catheter coupler;
   wherein the second catheter extends through the first catheter coupler and the first catheter.

2. The delivery system of claim 1 further comprising a pusher element positioned within the second catheter.

3. The delivery system of claim 2 wherein a valve implant or repair device is detachably connected to the pusher element.

4. The delivery system of claim 1 wherein the outlet port of the first catheter coupler is coupled to a pressure sensor.

5. The delivery system of claim 1 wherein the outlet port of the second catheter coupler is coupled to a pressure sensor.

6. The delivery system of claim 1 wherein the first catheter includes a radially inwardly extending projection that maintains a flow path between the first catheter and the second catheter.

7. The delivery system of claim 6 wherein the radially inwardly extending projection contains a catheter steering wire.

8. A delivery system comprising:
   a first a catheter coupler comprising:
      a first catheter connection lumen;
      an outer circumferential passage;
      a plurality of connecting passages that each connect the catheter connection lumen to the outer circumferential passage;
      an outlet port in fluid communication with the outer circumferential passage; and
      wherein the outer circumferential passage and the plurality of connecting passages are sized such that when:
         the outlet port is oriented in a direction not vertically upward;
         upper ones of the connecting passages contain air;
         lower ones of the connecting passages contain liquid; and
         a vacuum is applied to the tube;
      the air is drawn out of the outlet port;
   a second catheter coupler comprising:
      a second catheter connection lumen;
      an outer circumferential passage;
      a plurality of connecting passages that each connect the catheter connection lumen to the outer circumferential passage;
      an outlet port in fluid communication with the outer circumferential passage; and
   a first catheter connected to the first catheter connection lumen of the first catheter coupler;
   a second catheter connected to the second catheter connection lumen of the second catheter coupler;
   wherein the second catheter extends through the first catheter coupler and the first catheter or the first catheter extends through the second catheter coupler and the second catheter.

9. The delivery system of claim 8 further comprising a pusher element positioned within the second catheter.

10. The delivery system of claim 9 wherein a valve implant or repair device is detachably connected to the pusher element.

11. The delivery system of claim 8 wherein the outlet port of the first catheter coupler is coupled to a pressure sensor.

12. The delivery system of claim 8 wherein the outlet port of the second catheter coupler is coupled to a pressure sensor.

13. The delivery system of claim 8 wherein the first catheter includes a radially inwardly extending projection that maintains a flow path between the first catheter and the second catheter.

14. The delivery system of claim 13 wherein the radially inwardly extending projection contains a catheter steering wire.

15. A delivery system comprising:
a first a catheter coupler comprising:
 a first catheter connection lumen;
 an outer circumferential passage;
 a plurality of connecting passages that each connect the catheter connection lumen to the outer circumferential passage;
 an outlet port in fluid communication with the outer circumferential passage; and
 wherein the outer circumferential passage and the plurality of connecting passages are sized such that when:
  the outlet port is oriented in a direction not vertically upward;
  upper ones of the connecting passages contain air;
  lower ones of the connecting passages contain liquid; and
  a vacuum is applied to the tube;
  the air is drawn out of the outlet port;
a second catheter coupler;
a first catheter connected to the first catheter connection lumen of the first catheter coupler;
a second catheter connected to the second catheter coupler;
wherein the second catheter extends through the first catheter or the first catheter extends through the second catheter.

16. The delivery system of claim 15 further comprising a pusher element positioned within the second catheter.

17. The delivery system of claim 16 wherein a valve implant or repair device is detachably connected to the pusher element.

18. The delivery system of claim 15 wherein the outlet port of the first catheter coupler is coupled to a pressure sensor.

19. The delivery system of claim 15 wherein the outlet port of the second catheter coupler is coupled to a pressure sensor.

20. The delivery system of claim 15 wherein the first catheter includes a radially inwardly extending projection that maintains a flow path between the first catheter and the second catheter.

21. The delivery system of claim 20 wherein the radially inwardly extending projection contains a catheter steering wire.

* * * * *